US012465635B2

(12) United States Patent
Mpofu et al.

(10) Patent No.: US 12,465,635 B2
(45) **Date of Patent: *Nov. 11, 2025**

(54) METHODS OF TREATING INFLAMMATORY ARTHRITIS USING SECUKINUMAB

(71) Applicant: NOVARTIS AG, Basel (CH)

(72) Inventors: Shephard Mpofu, Oberwil (CH); Hanno Richards, Therwil (CH); Karthinathan Thangavelu, Geneva (CH); Matthias Machacek, Allschwil (CH)

(73) Assignee: NOVARTIS AG, Basel (CH)

(*) Notice: Subject to any disclaimer, the term of this patent is extended or adjusted under 35 U.S.C. 154(b) by 756 days.

This patent is subject to a terminal disclaimer.

(21) Appl. No.: 17/545,894

(22) Filed: Dec. 8, 2021

(65) Prior Publication Data

US 2022/0193234 A1 Jun. 23, 2022

Related U.S. Application Data

(62) Division of application No. 16/439,423, filed on Jun. 12, 2019, now abandoned, which is a division of application No. 15/654,854, filed on Jul. 20, 2017, now Pat. No. 10,363,307, which is a division of application No. 13/877,585, filed as application No. PCT/EP2011/069476 on Nov. 4, 2011, now Pat. No. 9,744,234.

(60) Provisional application No. 61/410,533, filed on Nov. 5, 2010.

(51) Int. Cl.

| | |
|---|---|
| ***A61K 39/395*** | (2006.01) |
| ***A61K 31/519*** | (2006.01) |
| ***A61K 45/06*** | (2006.01) |
| ***C07K 16/24*** | (2006.01) |
| *A61K 39/00* | (2006.01) |

(52) U.S. Cl.

CPC ........ *A61K 39/3955* (2013.01); *A61K 31/519* (2013.01); *A61K 45/06* (2013.01); *C07K 16/244* (2013.01); *A61K 2039/505* (2013.01); *A61K 2039/545* (2013.01); *A61K 2039/55* (2013.01); *C07K 2317/21* (2013.01); *C07K 2317/34* (2013.01); *C07K 2317/76* (2013.01); *C07K 2317/90* (2013.01)

(58) Field of Classification Search

CPC ........ A61K 2039/505; A61K 2039/545; C07K 2317/76; A61P 17/06; A61P 19/02

See application file for complete search history.

(56) References Cited

U.S. PATENT DOCUMENTS

| | | | |
|---|---|---|---|
| 5,250,442 A | 10/1993 | Orestes | |
| 6,309,636 B1 | 10/2001 | do Couto | |
| 8,119,131 B2 | 2/2012 | DiPadova | |
| 9,717,791 B2 | 8/2017 | Guettner et al. | |
| 9,744,234 B2 | 8/2017 | Mpofu et al. | |
| 11,280,479 B2 | 3/2022 | Meyer et al. | |
| 2005/0147609 A1 | 7/2005 | Filvaroff | |
| 2008/0044423 A1 | 2/2008 | Cochrane | |
| 2010/0080812 A1 | 4/2010 | Auer et al. | |
| 2010/0266608 A1 | 10/2010 | Cooreman et al. | |
| 2012/0045848 A1 | 2/2012 | Haugland et al. | |
| 2013/0202610 A1 | 8/2013 | Guettner et al. | |
| 2013/0209480 A1 | 8/2013 | Mpofu et al. | |
| 2018/0008706 A1 | 1/2018 | Mpofu et al. | |

FOREIGN PATENT DOCUMENTS

| | | | |
|---|---|---|---|
| CN | 104244979 | A | 12/2014 |
| EP | 3111954 | A1 | 1/2017 |
| JP | 2000186048 | | 7/2000 |
| JP | 2015519311 | A | 7/2015 |
| WO | 2006013107 | | 2/2006 |
| WO | 2006013107 | A1 | 2/2006 |
| WO | 2006096491 | A2 | 9/2006 |
| WO | 2007059188 | A1 | 5/2007 |
| WO | 2007117749 | A2 | 10/2007 |
| WO | 2007149032 | A1 | 12/2007 |
| WO | 2008030611 | A2 | 3/2008 |
| WO | 2008054603 | A2 | 5/2008 |
| WO | 2008121615 | A2 | 10/2008 |
| WO | 2008156865 | A2 | 12/2008 |
| WO | 2009002859 | A1 | 12/2008 |
| WO | 2009149168 | A2 | 12/2009 |
| WO | 2010006060 | A2 | 1/2010 |
| WO | 2010056804 | A1 | 5/2010 |
| WO | 2010065491 | A2 | 6/2010 |
| WO | 2010102251 | A2 | 9/2010 |
| WO | 2012059598 | A2 | 5/2012 |
| WO | 2012082573 | A1 | 6/2012 |

(Continued)

OTHER PUBLICATIONS

Eric J Yang et al: "Secukinumab in the treatment of psoriasis: patient selection and perspectives", Psoriasis: Targets and Therapy, vol. 8, Oct. 1, 2018 (Oct. 1, 2018), pp. 75-82, XP55723379, DOI: 10.2147/PTT.S146004.

P J Mease: "Psoriatic arthritis assessment tools in clinical trials", Annals of the Rheumatic Diseases, vol. 64, No. suppl_2, Mar. 1, 2005 (Mar. 1, 2005), pp. ii49-ii54, XP55723382, GB ISSN: 0003-4967, DOI: 10.1136/ard.2004.034165.

Anonymous: "Rheumatologists chose ACR50, ACR70 over ACR20 as endpoints when prescribing psoriatic arthritis drugs", Heallo Psoriatic Disease, Apr. 30, 2014 (Mar. 30, 2014), XP55723384, Retrieved from the Internet: URL:https://www.healio.com/news/dermatology/20140501/rheumatoogists-chose-acr50-70-over-acr20-as-endpoints-when-prescribing-psoriatic-arthritis-drugs [retrieved on Aug. 18, 2020].

(Continued)

*Primary Examiner* — Dong Jiang

(74) *Attorney, Agent, or Firm* — David Goetz

(57) ABSTRACT

The disclosure relates to novel regimens for treating an inflammatory arthritis, e.g., psoriatic arthritis, which employ a therapeutically effective amount of an Interleukin-17 (IL-17) antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof).

18 Claims, 13 Drawing Sheets

Specification includes a Sequence Listing.

(56) References Cited

FOREIGN PATENT DOCUMENTS

| | | | |
|---|---|---|---|
| WO | 2013077907 | A1 | 5/2013 |
| WO | 2013158821 | A2 | 10/2013 |
| WO | 2014155278 | A2 | 10/2014 |
| WO | 2017068472 | A1 | 4/2017 |

OTHER PUBLICATIONS

Letko et al., Invest Opthalmol Vis Sci, 2013, 54:E-Abstract 5929.
Porter et al., J Pharm Sci, 2000, 89:297-310.
Wang et al., Clin. Pharma. Ther., 2008, 84:548-558.
Haller et al., Pharma Tech, 2007, 10(31).
Zhao et al., Acta Pharmacologica Sinica, 2012, 33:1339-1347.
Kagan et al., Pharm. Res., 2012, 29:490-499.
Ogura et al., Immunity, 2008, 29:628-636.
Mok et al., Clin Rheumatol, 2013, 32:1429-1435.
Wolbink et al., Curr. Opin. Rheum., 2009, 21(3):211-215.
Salvana and Salata, Clin. Microbio. Reviews, 2009, 22(2):274-290.
NCT01109940, updated Jun. 22, 2010.
Wang et al., J Clin Pharmacol, 2009, 49:1012-1024.
Lalonde et al., Clin. Pharma. & Ther., 2007, 82:21-32.
Sacks et al., JAMA, 2014, 311:378-384.
Cross et al., Pharmacoepidemiology & Drug Safety, 2002, 11:439-446.
Mould and Green, Biodrugs, 2010, 24(1):23-29.
Genovese et al., Ann. Rheum. Dis., 2013, 72:863-869.
Remicade Package Insert, dated Aug. 1998.
Remicade Package Insert, dated Oct. 2015.
Keizer et al., Clin Pharmacokinet, 2010, 49(8):493-507.
Meibohm, 2006, The Role of Pharmacokinetics and Pharmacodynamics in the Development of Biotech Drugs:, Chapter 1, p. 6 in Pharmacokinetics and Pharmacodynamics of Biotech Drugs: Principles and Case Studies in Drug Development, Ed. B. Meibohn, Wiley-VCH, Weinheim.
Kiltz et al., Curr Opin Rheumatol, 2012, 24(3):252-260.
Goodman, "Secukinumab Successful in Spondylitis, Psoriatic Arthritis", Medscape Medical News, 2014, p. 1 (available at www.medscape.com).
Freeman, "Secukinumab improves Patient-Reported Outcomes in Ankylosing Spondylitis", Rheumatology News, 2016, (Available at www.mdedge.com/rheumatologynews).
Kelly, "Secukinumab Effective for Ankylosing Spondylitis in Phase 3 Trials", Medscape Medical News (2015).
Press Release (2015) "Novartis announces one-year results demonstrating sustained efficacy with investigational secukinumab in ankylosing spondylitis patients at EULAR", MarketWatch (available at www.marketwatch.com).
Chen and Liu, "Sulfasalazine for ankylosing spondylitis", Cochrane Database Syst Rev, 2005, 2:CD004800.
Declaration of Brian Porter (including exhibits) dated Feb. 21, 2017.
Declaration of Renard Didier (including exhibits) dated Mar. 2, 2017.
Clinical Trials database entry NCT01109940, dated Jun. 22, 2010.
Yang et al., "Crystalline monoclonal antibodies for subcutaneous delivery", PNAS, 2003, 100(12):6934-6939.
Dicke et al., "Secukinumab in the Treatment of Noninfectious UveitisL result of Three Randomized Controlled Clinical Trials", Ophthalmology, 2013, 120(4):777-787.
Buggage et al., "the Study of IL-17A Expression as a Biomarker for Patients with Active Noninfectious Uveitis Treated With AIN457", Assoc for Research in Vision and Ophthalmology, abstract 3799D1066, Session 383, Presented May 4, 2010.
Recker et al., "Insufficiently dosed intravenous ibandronate injections are associated with suboptimal antifracture efficacy in postmenopausal osteoporosis", Bone, 2004, 34(5):890-899.
Zhao et al., "Clinical pharmacology considerations in biologics development", Acta Pharm Sinica, 2012, 33:1339-1347.
Sacks et al., "Scientific and Regulatory Reasons for Delay and Denial of FDA Approval of Initial Applications for New Drugs, 2000-2012", JAMA, 2014, 311:378-384.
Richter et al., "Mechanistic Determinates of Biotherapeutics Absorption Following SC Adinistration", AAPS Journal, 2012, 14:559-570.
Porter et al., "Lymphatic transport of proteins after s.c. injections: implications of animal model selection", Adv. Drug Delivery Reviews, 2001, 50:157-171.
Wang et al., "Monolonal Antibody Pharmacokinetics and Pharmacodynamics", Clin Pharmacol Ther., 2008, 84 (5):548-558.
Declaration of Dr. Oliver Sander dated Oct. 19, 2015.
Clinical Trial database entry NCT00928512 (dated Jun. 29, 2015).
Clinical Trial database entry NCT 00809159 (dated Jun. 22, 2010).
Declaration of Dr. Diane Mould, dated Jan. 29, 2017, filed in U.S. Appl. No. 10/163,657.
Balague et al., "Understanding autoimmune disease: new targets for drug discovery", Drug Discovery Today, 2009, 14 (19/20):926-934.
John Collett Ed-Aulton Me (ED) 2: "Dosage Regimens", 2001, Pharmaceutics: the Science of Dosage Form Design, London, Churchill Livingstone, GB, pp. 275-288, XP003030862, ISBN: 978-0-443-05517-1.
Romao et al., "Old drugs, old problems: where do we stand in prediction of rheumatoid arthritis responsiveness to methotrexate and other synthetic DMARDs?", BMC Medicine, 2013, 11(17):1-24. [downloaded at http://www.biomedcentral.com/1741-7016/11/17].
Machold et al., "Very Recent onset rheumatoid arthritis: clinical and seological patient characteristics associated with radiographic progression over the first years of disease", Rheumatology, 2007, 46:342-349.
Potter et al., "Association of rheumatoid factor and anti-cyclic citrullinated peptide positivity, but not carriage of shared epitope or PTPN22 susceptibility variants, with anti-tumour necrosis factor response in rheumatoid arthritis", Ann Rheum Dis, 2009, 68:69-74.
Yildirim et al., "Associations between Acute Phase Reactant Levels and Disease Activity Score (DAS28) in Patients with Rheumatoid Arthritis", Annals of Clinical & Laboratory Science, 2004, 34(4):423-426.
Scott et al., "Seminar—Rheumatoid Arthritis", Lancet, 2010, 376:1094-1108.
Gladman et al., "Psoriatic arthritis: epidemiology, clinical features, course and outcome", Ann Rheum Dis, 2005, 64 (Suppl 11):ii14-ii17.
Boehncke and Menter", Burden of Disease: Psoriasis and Psoriatic Arthritis", Am J Clin Dermatol, 2013, 14:377-388.
Psoriatic Arthritis (PsA):A Distinct, Complex disease downloaded http://discoverpsa.com on Feb. 2, 2016.
Nash et al., "Secukinumab for the treatment of psoriatic arthritis: comparative effectiveness results versus adalimumab up to 48 weeks using a matching-adjusted indirect comparison", Ann Rheum Dis, 2016, 75(Suppl 2):353 (Published Abstract).
Strand et al., "Secukinumab for the Treatment of Psoriatic Arthritis: Comparative Effectiveness Versus Infliximab Using a Matching-Adjusted Indirect Comparison", Arthritis Rheumatol., 2016, 68 (Suppl 10).
Xenofen et al., "Interleukin-17A Blockade with Secukinuman Reduced Spinal Inflammation in Patients with Ankylosing Spondylitis As Early As Week 6, As Detected by Magnetic Resonance Imaing", Arthritis and Rheumatism, 75th Annual Scientific meeting of the American college of Rheumatology/46th annual Scientific meeting, Chicago, IL, USA, Nov. 4-9, 2011, Wiley Interscience, US 63(10):Suppl. S, Nov. 1, 2011 (Nov. 1, 2011) p. S972.
Baeten et al., "L7-The anti-IL-17A monoclonal antibody Secukinumab (AIN457) showed good safety and efficacy in the treatment of active ankylosing spondylitis", Late Breaking Abstracts: American College of Rheumatology 2010 Annual Scientific Meeting, Nov. 30, 2010 (Nov. 30, 2010) Retrieved from the internet: URL::http://onlinelibrary.wiley.com/doi/10.1002/art.30132/pdf [retrieved on Sep. 14, 2016].
Lubberts, "Th17 cytokines and arthritis", Seminars IN Immunopathology, Springer, Berlin, DE, 2010, 32(1):43-53 XP019800827, ISSN: 1863-2300.

(56) References Cited

OTHER PUBLICATIONS

McInnes, "Anti-Interleukin' 17A Monoclonal Antibody Secukinumab Reduces Signs and Symptoms of PSoriatic Arthritis in a 24-Week Multicenter, Double-Blind, Randomized, Placebo-Controlled Trial", Arthritis and Rheumatism, vol. 63, Nov. 2011 Abstract Supplement, Oct. 2010, retirieved from the internet; URL:http://www.blackwellpublishing.com/acrmeeting/abstract.asp?MeetingID=781&id=95525 [retrieved Sep. 14, 2016].
Novartis: "View of NCT00809614 on 2010_04_29", ClinicalTrials.gov archive, Apr. 29, 2010, Retrieved from the Internet: URL:https://clinicaltrials.gov/archive/NCT00809614/2010_04_29 [Retrieved Sep. 14, 2016}.
Novartis "View of NCT00809159 on 2010_06_22", CLinicalTrials.gov archive, Jun. 22, 2010, REtrieved from the internet, https://clinicaltrials.gov/archive/NCT00809159/2010_06_22 [Retrieved Sep. 7, 2016].
Genovese et al., "Efficacy and safety of secukinumab in patients with rheumatoid arthritis: a phase II, dose-finding, double-blind, randomized, placebo controlled study", Ann Rheum Dis, 2013, 72:863-869.
Sieper et al., "Secukinumab efficacy in anti-TNF-naive and anti-TNF-experienced subjects with active anylosing spondylitis: results from the MEASURE 2 Study", Ann Rheum, 2016, doi.10.1136/annrheumdis-2016-210023 (e-pub ahead of print).
McInnes et al., "Secukinumab, a human anti-interleikin-17A monoclonal antibody, in patients with psoriatic arthritis (FUTURE 2): a randomised, double-blind, placebo-controlled, phase 3 trial", Lancet, 2015, 386(9999):19-25.
Kavanaugh, "Efficacy of Subcutaneous Secukinumab in Patients with Active Psoriatic Arthritis Stratifies by Prior Tumor Necrosis Factor Inhibitor Use: Results from the Randomized Placebo-controlled FUTURE 2 Study", J. Rheumatol., 2016, 43(9):1713-1717.
Hueber et al., "Secukinumab, a human anti-IL-17A monoclonal antibody, for moderate to severe Crohn's disease: unexpected results of a randomised, double-blind placebo controlled trial", Gut, 2012, 61:1693-1700.
Gottlieb et al., "Guidelines of care for the management of psoriases and psoriatic arthritis", J Am Acad Dermatol, 2008, 58:851-864.
Van der Horst-Bruinsma et al., "A systematic coparison of rheumatoid arthritis and anylosing spondylitis", Clin. Exp. Rheumatol., 2009, 27(4Supple 55):S43-9.
Vandooren et al., "Absence of a Classically Activated Macrophage Cytokine Signature in Peripheral Sponylarthritis Including Psoriatic Arthritis", Arthritis Rheum, 2009, 60(4):966-975.
Meibohm, "The role of pharmacokinetics and pharmacodynamics in the development of biotech drugs", Wiley-VCH Verlag Gmbh & Co. KGaA, 2006, Chapter 1.
Keizer et al., "Clinical Pharmacokinetics of therapeutic monoclonal antibodies", CLin Pharmacokinet, 2010, 49 (8):493-507.
Wang et al., "Fixed dosing versus body size-based dosing of monoclonal antibodies in adult clinical trials", J Clin Pharmacol., 2009, 49:1012-1024.
Baeten et al., Lancet, 2013, 382(9906):1705-13.
Dougados and Baeten, Lancet, 2011, 377:2127-2137.
Vandporen et al., Arthritis Rheum, 2009, 80:966-975.
Melis et al., Ann. Rheum. Dis., 2010, 69:618-623.
Ciccia et al., Arthritis Rheum, 2009, 60:955-965.
Sieper et al, Ann Rheum Dis, 2014, 73:95-100.
Sieper et al., Abstract 536, presented ACR/ARHP Annual Meeting, Boston, Massachusetts, US, 2014.
Deodhar, Ann. Rheum, Dis, 2015, 74:1144.
Maksymnowych, Ann. Rheum. Dis., 2016, 75(Suppl 2):98.
Van der Heijde, Arthr. Rheum., 2006, 54(7):2136-2146.
Clinicaltrials.gov database entry NCT01870284, last updated Sep. 15, 2014.
Clinicaltrials.gov databse entry NCT02696785, first received Feb. 26, 2016.
Press Release, Amgen and Wyeth, dated Jul. 24, 2003.
Braun et al., Expert Op. Biological Therapy, 2016, 16(5):711-722.
Sieper et al, Ann Rheum Dis, 2016, 0:1-5 doi:1031136/annrheumdis-2016-210023.
Marzo-Ortega et al., Ann Rheum Dis, 2016, 75Suppl 2:812-813.
Sieper et al., Ann Rheum Dis, 2015, 74(6):1051-1057.
Song et al., Ann Rheum Dis, 2011, 70:1108-1110.
Haibel et al., Ann Rheum Dis, 2005, 64:296-298.
Song et al., Arthritis Rheum, 2010, 62:1290-1297.
Braun et al., Expert Opin Emerg Drugs, 2015, 20(1):1-14.
Maldonado-Ficco et al., Clin Rheumatol, 2016, 35:2151-2161.
Van der Heijde et al., Arthritis Rheum, 2005, 52:582-591.
Davis et al., Arthritis Rheum, 2003, 48:3230-3236.
Inman et al., Arthritis Rhem, 2008, 58:3402-3412.
Landewe et al., Ann Rheum Dis, 2014, 73:39-47.
Sieper et al., Ann Rheum Dis, 2011, 10.1136/annrheumdis-2011-200358.
Clinical Trial NCT01107457 (Apr. 20, 2010).
Saber et al., "Remission in psoriatic arthritis: is it possible and how can it be predicted?", Arthritis Research & Therapy, 12(3):R94. (2010).
Wang, "Instability, stabilization, and formulation of liquid protein pharmaceuticals", International Journal of Pharmaceutics, 185:129-188. (1999).
Falconer, "Advances in liquid formulations of parenteral therapeutic proteins", Biotechnology Advances, 37(7):107412. (2019).
Griffiths et al., "Psoriasis and Psoriatic Arthritis: Immunological Aspects and Therapeutic Guidelines," Clin Exp Rheumatol, Jan.-Feb. 2006, vol. 24, Suppl. 40, pp. S72-S78.
ACR Call for Late-Breaking Abstracts, Guidelines for Submission, Nov. 10-14, 2022.
Hennigan, et al., Adalimumab in ankylosing spondylitis: an evidence-based review of its place in therapy, Core Evidence, 2008, 295-305, 2(4).
Jandus, et al., Increased Numbers of Circulating Polyfunctional Th17 Memory Cells in Patients With Seronegative Spondylarthritedes, Arthritis and Rheumatism, Aug. 2008, 2307-2317, 58(8).
Newsome, et al., The clinical pharmacology of therapeutic monoclonal antibodies in the treatment of malignancy; have the magic bullets arrived?, British Journal of Clinical Pharmacology, May 22, 2008, 6-19, 66(1).
Zuidema et al., "Release and Absorption Rates of Intramuscularly and Subcutaneously Injected Pharmaceuticals," International Journal of Pharmaceuticals, 1994, vol. 105, pp. 189-207.
Falconer, "Advances in Liquid Formulations of Parenteral Therapeutic Proteins," Biotechnology Advances, 2019, vol. 37, pp. 1-9.
Haller, "Converting Intravenous Dosing to Subcutaneous Dosing," Parenteral Formulation, 2007, pp. 118-132.
Igawa et al., "Reduced Elimination of IgG Antibodies by Engineering the Variable Region," Protein Engineering Design & Selection, 2010, vol. 23, No. 5, pp. 385-392.
Boswell et al., "Effects of Charge on Antibody Tissue Distribution and Pharmacokinetics," Bioconjugate Chem., 2010, vol. 21, pp. 2153-2163.
Baraliakos, et al., Biologic Therapies for Spondyloartritis: What is new?, Current Rheumatology Reports, Aug. 2, 2012, 422-427, 14.
Baraliakos, et al., Long-term effects of secukinumab on MRI findings in relation to clinical efficacy in subjects with active ankylosing spondylitis: an observational study, Annals of Rheumatic Diseases, Aug. 6, 2015, 408-412, 75.
Baron-Faust, The IL-17 Superfamily: What Future for PsA?, Rheumatology Network, Mar. 18, 2014.
Chandran, et al., Reappraisal of the effectiveness of methotrexate in psoriatic arthritis: results from a longitudinal observational cohort, Journal of Rheumatology, 2008, 469-471, 35(3).
Clinical Trial NCT04209205, Dec. 24, 2019, available at https://www.clinicaltrials.gov/ct2/show/NCT04209205.
Cosentyx prescribing information, revised Jan. 2020.
Cosentyx Summary of Products Characteristics, Sep. 1, 2017.
Daikh, et al., Advances in managing ankylosing spondylitis, F1000 Prime Reports, Sep. 4, 2014, 6(78).
Danve, et al., IL-17 Inhibition in Axial Spondyloarthritis, Current Treatment Options in Rheumatology, Apr. 2, 2015, 221-230, 1.
Deodhar, et al., Secukinumab 150 mg significantly improved signs and symptoms of non-radiographic axial spondyloarthritis: Result

(56) References Cited

OTHER PUBLICATIONS from a phase 3 double-blind, randomized, placebo-controlled study, ACR/ARP Annual Meeting, Nov. 12, 2019, abstract No. L21.
Deodhar, et al., Secukinumab 150 mg significantly improved signs and symptoms of non-radiographic axial spondyloarthritis: Result from a phase 3 double-blind, randomized, placebo-controlled study, ACR/ARP annual meeting, Nov. 12, 2019, presentation No. L21.
Deodhar, et al., The term 'non-radiographic axial spondyloarthritis' is much more important to classify than to diagnose patients with axial spondyloarthritis, Annals of Rheumatic Diseases, 2016, 791-794, 75.
Fagerli, et al., Switching between TNF inhibitors in psoriatic arthritis: data from the NOR-DMARD study, Annals of Rheumatic Diseases, Apr. 5, 2013, 1840-1844, 72.
Gaffen, et al., The IL-23-IL-17 immune axis: from mechanisms to therapeutic testing, Nature Reviews Immunology, Sep. 2014, 585-600, 14.
Genco, FDA Approval Of The First nr-AxSpA Biologics: Projecting Regulatory & Market Dynamics, Biosimilar Development, Feb. 27, 2019.
Goh, et al., Update on biologic therapies in ankylosing spondylitis: a literature review, International Journal of Rheumatic Disease, 2012, 445-454, 15.
Gottlieb, et al., Secukinumab Reduces Hscrp Levels in Subjects with Moderate-To-Severe Plaque Psoriasis and Concomitant Psoriatic Arthritis: A Sub-Analysis from the Phase 3 Erasure Study, Annals of the Rheumatic Diseases, Jun. 2014, AB0738, 1047-1048, 73.
Gottlieb, et al., Secukinumab Shows Substantial Improvement In Both Psoriasis Symptoms and Physical Functioning In Moderate To-Severe Plaque Psoriasis Patients With Psoriatic Arthritis: A Subanalysis Of a Phase 3, Multicenter, Double-Blind, Placebo-Controlled Study, Abstract Submissions (ACR), Oct. 25-30, 2013, Abstract 319.
Goulabchand, et al., Effect of tumour necrosis factor blockers on radiographic progression of psoriatic arthritis: a systematic review and meta-analysis of randomised controlled trials, Annals of Rheumatic Diseases, 2014, 414-419, 73.
History of Changes for Study NCT00928512, Mar. 12, 2010, available at https://www.clinicaltrials.gov/ct2/show/NCT00928512.
History of Changes for Study NCT00995709, Oct. 14, 2009, available at https://www.clinicaltrials.gov/ct2/show/NCT00995709.
History of Changes for Study NCT01032915, Oct. 24, 2010, available at https://www.clinicaltrials.gov/study/NCT01032915.
History of Changes for Study NCT01071252, Feb. 18, 2010, available at https://www.clinicaltrials.gov/ct2/show/NCT01071252.
History of Changes for Study NCT01090310, Sep. 28, 2010, available at https://www.clinicaltrials.gov/ct2/show/NCT01090310.
History of Changes for Study NCT01093846, Oct. 13, 2010, available at https://www.clinicaltrials.gov/study/NCT01093846.
History of Changes for Study NCT01095250, Oct. 13, 2010, available at https://clinicaltrials.gov/ct2/history/NCT01095250?A=6&B=6&C=merged.
History of Changes for Study NCT01103024, Oct. 15, 2010, available at https://clinicaltrials.gov/study/NCT01103024?a=2&tab=history.
History of Changes for Study NCT01327664, Mar. 31, 2011, available at https://clinicaltrials.gov/study/NCT01327664?tab=history&a=1.
History of Changes for Study NCT01350804, Sep. 23, 2011, available at https://clinicaltrials.gov/study/NCT01350804?tab=history&a=3.
History of Changes for Study NCT01358578, Aug. 17, 2011, available at https://clinicaltrials.gov/study/NCT01358578?tab=history&a=6.
History of Changes for Study NCT01365455, Oct. 12, 2011, available at https://clinicaltrials.gov/study/NCT01365455?a=10&tab=history.
History of Changes for Study NCT01377012, Sep. 28, 2011, available at https://clinicaltrials.gov/study/NCT01377012?a=4&tab=history.
History of Changes for Study NCT01392326, Sep. 23, 2011, available at https://clinicaltrials.gov/study/NCT01392326?tab=history&a=2.
History of Changes for Study NCT01406938, Aug. 15, 2011, available at https://clinicaltrials.gov/study/NCT01406938?a=2&tab=history.
History of Changes for Study NCT01412944, Aug. 8, 2011, available at https://clinicaltrials.gov/study/NCT01412944?tab=history&a=1.
Humira prescribing information, revised Mar. 2020.
Kavanaugh, et al., The Infliximab Multinational Psoriatic Arthritis Controlled Trial (IMPACT): results of radiographic analyses after 1 year, Annals of Rheumatic Diseases, Jan. 26, 2006, 1038-1043, 65.
Kavanaugh, et al., Ustekinumab, an anti-IL-12/23 p40 monoclonal antibody, inhibits radiographic progression in patients with active psoriatic arthritis, Annals of Rheumatic Diseases, Feb. 19, 2014, 1000-1006, 73.
Kocijan, et al., Anti-TNFs in axial spondyloarthritis, Wiener Medizinische Wochenschrift, Jan. 9, 2015, 10-13, 165.
Kunder, Treatment of the patients with psoriatic arthritis, Medical News, 2013, 34-41, 6.
Langley, et al., Secukinumab in Plaque Psoriasis—Results of Two Phase 3 Trials, N Engl J Med., Jul. 24, 2014, 326-338, 371(4).
Machado, et al., New developments in the diagnosis and treatment of axial spondyloartritis, Clinical Investigation, 2013, 153-171, 3(2).
Madej, et al., Cytokine Profiles in Axial Spondyloarthritis, Reumatologia, 2015, 9-13, 53(1).
Mantravadi, et al., Tumor necrosis factor inhibitors in psoriatic arthritis, Expert Review of Clinical Pharmacology, May 22, 2017, 899-910, 10(8).
Mcinnes, et al., Anti-Interleukin 17A Monoclonal Antibody Secukinumab Reduces Signs And Symptoms Of Psoriatic Arthritis In A 24-Week Multicenter; Double•-blind, Randomized, Placebo-Controlled Trial, Arthritis and Rheumatism, Nov. 2011, 63.
Mckee, Novartis' Cosentyx shown to inhibit joint damage in PsA, Pharma Times, Nov. 7, 2017.
Mease, et al., Brodalumab, an Anti-IL17RA Monoclonal Antibody, in Psoriatic Arthritis, N Engl J Med., Jun. 12, 2014, 2295-2306, 370(24).
Mease, et al., Managing Patients with Psoriatic Disease: The Diagnosis and Pharmacologic Treatment of Psoriatic Arthritis in Patients with Psoriasis, Drugs, Feb. 25, 2014, 423-441, 74.
Mease, et al., Subcutaneous Secukinumab Inhibits Radiographic Progression in Psoriatic Arthritis: Primary Results from a Large Randomized, Controlled, Double-Blind Phase 3 Study, ACR/ARHP Annual Meeting, Oct. 19, 2017.
Mease, Non anti-TNF biologics on SpA and PsA, Annals of Rheumatic Diseases, Jun. 8, 2012, abstract SP0147.
Mrowietz, et al., Definition of treatment goals for moderate to severe psoriasis: a European consensus, Archives for Dermatological Research, Jan. 2011, 1-10, 303.
Novartis announces result of Prevent Study, dated Nov. 12, 2019, downloaded Dec. 11, 2019.
Patel, et al., Effect of IL-17A blockade with secukinumab in autoimmune diseases, Annals of Rheumatic Diseases, 2013, 116-123, 72.
Poddubnyy, Axial spondyloarthritis: is there a treatment of choice, Therapeutic Advances in Musculoskeletal Disease, 2013, 45-54, 5(1).
Poddubnyy, et al., Adalimumab for the treatment of ankylosing spondylitis and nonradiographic axial spondyloarthritis—a five-year update, Expert Opinion on Biological Therapy, 2013, 1599-1611, 13(11).
Poddubnyy, et al., Spontaneous, drug-induced, and drug-free remission in peripheral and axial spondyloarthritis, Best Practice & Research Clinical Rheumatology, 2014, 807-818, 28.
Rodriguez, et al., Old and new treatment targets in axial spondyloarthritis, RMD Open, Apr. 5, 2015, 1.

(56) References Cited

OTHER PUBLICATIONS

Rudwaleit, et al., The development of Assessment of Spondyloarthritis international Society classification criterai for axial spondyloarthritis (part I): classification of paper patients by expert opinion including uncertainty appraisal, Extended Report, Mar. 17, 2009.
Shostak, et al., Back pain of inflammatory genesis: seronegative spondyloarthropathy—the main approaches to diagnosis and therapy, The Clinician, Jan. 2011, 5.
Sieper, et al., Efficacy and safety of adalimumab in patients with non-radiographic axial spondyloarthritis: results of a randomised placebo-controlled trial (ABILITY-1), Clinical and epidemiological research, Jul. 7, 2012, 815-822.
Song, et al., Consistently Good Clinical Response in Patients with early Axial Spondyloartritis after 3 Years of continuous Treatment with Etanercept: Longterm Data of the ESTHER Trial, The Journal of Rheumatology, 2014, 2034-2040, 41(10).
Stelara Highlights of Prescribing Information, revised Sep. 2016.
Urano, Diagnosis of spondyloarthritis: from ankylosing spondylitis to axial spondyloarthritis, Inflammation and Immunity, 2013, 79-85, 21(1).
Van Der Heijde, et al., Effect of different imputation approaches on the evaluation of radiographic progression in patients with psoriatic arthritis: results of the RAPID-PsA 24-week phase III double-blind randomised placebo-controlled study of certolizumab pegol, Annals of Rheumatic Diseases, 2014, 233-237, 73.
Van Der Heijde, et al., Psoriatic arthritis imaging: a review of scoring methods, Annals of Rheumatic Diseases, 2005, 61-64, 64(suppl. 2).
Ward, et al., American College of Rheumatology/Spondylitis Association of America/Spondyloarthritis Research and Treatment Network 2015 Recommendations for the Treatment of Ankylosing Spondylitis and Nonradiographic Axial Spondyloarthritis, Arthritis and Rheumatology, Feb. 2016, 282-298, 68(2).
Weitz, et al., Ustekinumab: targeting the IL-17 pathway to improve outcomes in psoriatic arthritis, Expert Opinion on Biological Therapy, 2014, 515-526, 14(4).
Weselman, Psoriatic Arthritis, American College of Rheumatology, 2017.
Novartis, Clinical Trial Results, Protocol No. CAIN457F2304, study completion date Nov. 2020.
Smolen et al., "EULAR recommendations for the management of rheumatoid arthritis with synthetic and biological disease-modifying antirheumatic drugs", Ann. Rheum. Dis., 2010, 1-12, downloaded from ard.bmj.com on Oct. 27, 2010.
Aletaha et al., "2010 Rheumatoid arthritis classification criteria: an American College of Rheumatology/European League Against Rheumatism collaborative initiative", Ann Rheum. Dis., 2010, 69:1580-1588. [downloaded from ard.bmj.com on Aug. 20, 2013].
Genovese et al., "Secukinumab (AIN457), a novel monoclonal antibody targeting IL-17A demonstrates efficacy in active rheumatoid arthritis patients despite stable methotrexate treatment" Results of a Phase IIb Study, Arthritis and Rheumatism; Abstracts of the American College of Rheumatology & Association of Rheumatology Health Professionals, Annual Scientific Meeting, 62(Supple 10).
Hueber et al., "Effects of AIN457, a Fully Human Antibody to Interleukin-17A, on Psoriasis, Rheumatoid Arthritis, and Uveitis", Science Translational Medicine, American Association for the Advancement of Science, 2010, 2(52):1-9.
Genovese et al., "LY2439821, a humanized anti-leukin-17 monoclonal antobody, in the treatment of patients and rheumatoid arthritis: A Phase I randomized, d-blind, placebo-controlled, proof-of-concept study", Arthritis & Rheumatism, 2010, 62(4):929-939.
Yoshida et al., "Methotrexate suppresses inflammatory agonist induced interleukin 6 synthesis in osteoblasts", Journal of Rheumatology, 2005, 32(5):787-795.
Hou et al., "Methotrexate amellorates pristane-induced arthritis by decreasing IFN-[gamma] and IL-17A expressions", Journal of Zhejiang University—Science B, 2011, 12(1):40-46.
Clinical trial NCT00809159 (Dec. 16, 2008).
Clinical trial NCT00928512 (Jun. 25, 2009).
NCT01169844 on Jul. 23, 2010, clinicaltrials.gov archive, [online] Jul. 23, 2010. Internet <URL:https://clinicaltrials.gov/archive/NCTO_1169844/2010_07_23>.
Baeten et al., "Secukinumab, a Monocional ANtibody to Interleukin-17A, SignificantlyImproves Signs and Symptoms of Active Ankylosing Spondylitis: Results of a 52-Week Phase 3 Randomized Placebo-Controlled Trial with Intravenous Loading and Subcutaneous Maintenance Dosing", ACR/ARHP Annual Meeting, Abstract 819, 2014.
Mease and McInnes, "Secukinumab: A New Treatment Option for Psoriatic Arthritis", Rheumatol Ther, 2016, 3:5-29.
Sieper et al., "Secukinumab efficacy in anti-TNF-naive and anti-TNF-experienced subjects with active anylosing spondylitis: results from the MEASURE 2 Study", Ann Rheum Dis, 2017, 76:571-575.
Cosentyx Product Monograph, Canada, pp. 1-44, Aug. 17, 2017.
Olivieri et al., "Emerging drugs for psoriatic arthritis", Expert Opinion on Emerging Drugs, 2010, 15(3):399-414.
ACR/ARHP Call for abstracts Guidelines_Oct. 2010.
Anonymous: ""Object"—Definition & Meaning—Merriam-Webster", , Dec. 8, 2021 (Dec. 8, 2021), pp. 1-15, XP055870736, Retrieved from the Internet: URL:https://www.merriam-webster.com/dictionary/object [retrieved on Dec. 8, 2021.
Chioato, et al., Efficacy of Influenza and Meningococcal Vaccinations in Healthy Subjects Exposed to Secukinumab 150 Mg: Preliminary Study Results., Arthritis and Rheumatism, Oct. 2011, S711, 63(10).
Cosentyx prescribing information, revised Jan. 2016.
History of changes for Study NCT00669916, submitted on Apr. 9, 2015, available at https://clinicaltrials.gov/ct2/history/NCT00669916?V_5=View.
History of changes for Study NCT00669942, submitted on Mar. 27, 2015, available at https://clinicaltrials.gov/ct2/history/NCT00669942?A=5&B=5&C=merged.
History of changes for Study NCT00805480, submitted on Jan. 28, 2015, available at https://clinicaltrials.gov/ct2/history/NCT00805480?V_4=View.
History of changes for Study NCT00809614, submitted on Oct. 14, 2015, available at https://clinicaltrials.gov/ct2/history/NCT00809614?A=5&B=5&C=merged.
History of changes for Study NCT00995709, submitted on Aug. 13, 2015, available at https://clinicaltrials.gov/ct2/history/NCT00995709?V_7=View.
History of changes for Study NCT01032915, submitted on Oct. 8, 2015, available at https://clinicaltrials.gov/ct2/history/NCT01032915?V_4=View.
History of changes for Study NCT01071252, submitted on Feb. 12, 2015, available at https://clinicaltrials.gov/ct2/history/NCT01071252?V_1=View.
History of changes for Study NCT01090310, submitted on Dec. 8, 2015, available at https://clinicaltrials.gov/ct2/history/NCT01090310?V_2=View.
History of changes for Study NCT01093846 submitted on Jan. 22, 2016, available at https://clinicaltrials.gov/ct2/history/NCT01093846?V_2=View.
History of changes for Study NCT01095250, submitted on Oct. 5, 2015, available at https://clinicaltrials.gov/ct2/history/NCT01095250?A=6&B=6&C=merged.
History of changes for Study NCT01103024, submitted on May 2, 2012, available at https://clinicaltrials.gov/ct2/history/NCT01103024?A=2&B=2&C=merged.
History of changes for Study NCT01109940, submitted on Nov. 15, 2016, available at https://clinicaltrials.gov/ct2/history/NCT01109940?V_2=View.
History of changes for Study NCT01169844, submitted on Nov. 16, 2016, available at https://clinicaltrials.gov/ct2/history/NCT01169844?A=1&B=1&C=merged.
History of changes for Study NCT01327664, submitted on Dec. 5, 2013, available at https://clinicaltrials.gov/ct2/history/NCT01327664?V_1=View.
History of changes for Study NCT01350804, submitted on May 4, 2016, available at https://clinicaltrials.gov/ct2/history/NCT1350804?A=3&B=3&C=merged.

(56) References Cited

OTHER PUBLICATIONS

History of changes for Study NCT01358578, submitted on Mar. 29, 2019, available at https://clinicaltrials.gov/ct2/history/NCT01358578?A=6&B=6&C=merged.
History of changes for Study NCT01365455, submitted on Mar. 20, 2019, available at https://clinicaltrials.gov/ct2/history/NCT01365455?A=10&B=10&C=merged.
History of changes for Study NCT01377012, submitted on Feb. 9, 2017, available at https://clinicaltrials.gov/ct2/history/NCT1377012?A=4&B=4&C=merged.
History of changes for Study NCT01392326, submitted on Jan. 5, 2016, available at https://clinicaltrials.gov/ct2/history/NCT01392326?A=2&B=2&C=merged.
History of changes for Study NCT01406938, submitted on Apr. 30, 2015, available at https://clinicaltrials.gov/ct2/history/NCT01406938?A=2&B=2&C=merged.
History of changes for Study NCT01412944, submitted on Mar. 17, 2015, available at https://clinicaltrials.gov/ct2/history/NCT01412944?A=1&B=1&C=merged.
Kivitz, et al., Efficacy and Safety of Secukinumab 150 mg with and Without Loading Regimen in Ankylosing Spondylitis: 104-week Results from MEASURE 4 Study, Rheumatology and Therapy, Aug. 18, 2018, 447-462, 5.
Mayo Clinic_Apr. 30, 2020_Diagnosis and treatment of Uveitis https://www.mayoclinic.org/diseasesconditions/uveitis/diagnosis-treatment/drc-20378739?p=1.
Nash, et al., Secukinumab for psoriatic arthritis: comparative effectiveness results versus etanercept up to 24 weeks using a matching-adjusted indirect comparison, International Journal of Rheumatic Diseases, 2016, 163, 19(2).
NHSC Publication, May 2010, AIN-457 for posterior uveitis, 5 pages.
Online publication_Sep. 27, 2011_Arthritis & Rheumatism.
Online publication_Dec. 9, 2011_Arthritis & Rheumatism.
Pavelka, et al., Efficacy, safety, and tolerability of secukinumab in patients with active ankylosing spondylitis: a randomized, doubleblind phase 3 study, MEASURE 3, Arthritis Research and Therapy, Dec. 22, 2017, 27 pages, 19(285).
Proprietor's letter to the Examining Division_Feb. 15, 2018.
Reichert, Antibody-based therapeutics to watch in 2011, mAbs, Jan. 1, 2011, 76-99, 3(1).
Samson, et al., An Open-Label Proof-Of Concept Study to Assess the Efficacy of AIN457 in Patients With Noninfectious Uveitis, Invest Ophthalmol Vis Sci., Apr. 2010, 51.
Tak, et al., A1N457 Shows a Good Safety Profile and Clinical Benefit in Patients with Active Rheumatoid Arthritis (RA) Despite Methotrexate Therapy: 16-Weeks Results From a Randomized Proof-of-Concept Trial, ACR/ARHP Scientific Meeting, Oct. 20, 2009, presentation No. 1922.
Taltz prescribing information, revised Aug. 2019, 1 page.
U.S. Appl. No. 61/410,533, filed Nov. 5, 2010.
Wayback Machine_Oct. 29, 2010_www.rheumatology.org, retrieved from the Internet: URL - https://web.archive.org/web/20101029090319/http:/www.rheumatology.org/.
Wiley: "Publication Date of D2", Dec. 9, 2021 (Dec. 9, 2021), pp. 1-2, XP55871165, [retrieved on Dec. 8, 2021].
Benhamou et al_2010_Rheumatology.
Baeten et al_2010_Arthritis and Rheumatism.
ClinicalTrials.gov Archive, Jun. 22, 2010, p. 1-2, https://clinicaltrials.gov/archive/NTC01109940/2010_06_22.
Science Translational Medicine, Oct. 1, 2010, 2(52):Article 52RA72, pp. 1-9.
Expert Opinion Emerging Drugs, 15(3):399-414, Sep. 2010, CR12.
ClinicalTrials.gov; 16 Week Efficacy and 5 Year Long Term Efficacy, Safety and Tolerability of Secukinumab in Patients With Active Ankylosing Spondylitis, pp. 1-9.
Late-Breaking Abstracts: American College of Rheumatology, 2010 Annual Scientific Meeting.
Baeten et al., "The Anti-IL17A Monoclonal Antibody Secukinumab (AIN457) showed good safety and efficacy in the treatment of active ankylosing spondylitis", Arthritis & Rhematism, 2010, vol. 62:3840-3841.
Arthritis & Rheumatism, Journal of the American College of Rheumatology, vol. 63, No. 10, Abstract Supplemental.
Baeten et al., "Secukinumab, an Interleukin-17A Inhibitor, in Ankylosing Spondylitis", The New England Journal of Medicine, 2015, 2534-2548.
Methods of Treating Rheumatoid Arthritis Using IL-17 Antagonists, pp. 1-99, FF Text.
ClinicalTrials.gov Archive, History of Changes for Study: NCT00809159, Double Blind, Placebo Controlled Study to Assess Efficacy of AIN457 in Moderate to Severe Ankylosing Spondylitis, U.S. National Library of Medicine, p. 1-9.
ClinicalTrials.gov Archive, History of Changes for Study, NCT00928512, Efficacy, Safety and Tolerability of AIN457 in Patients With Rheumatoid Arthritis (RA) Taking Methotrexate (MTX), pp. 1-9.
Hueber et al., "Effects of AIN457, a Fully Human Antibody to Interleukin-17A, on Psoriasis, Rheumatoid Arthritis, and Uveitis", 2010, 2(52)52ra72:1-11.
Van der Heijde et al., "Adalimumab Effectiveness for the treatment of ankylosing spondylitis is maintained for up to 2 years: long-term results from the ATLAS trial, Extended Report", Ann Rheum Dis., 2009, pp. 922-929.
Davis et al., "Recombinant Human Tumor Necrosis Factor Receptor (etanercept) for Treating Ankylosing Spondylitis, A Randomized, Controlled Trial", Arthritis & Rheumatism, 2003, 48(11):3230-3236.
Inman et al., "Efficacy and Safety of Golimumab in Patients with Ankylosing Spondylitis, Results of a Randomized, Double-Blind, Placebo-Controlled, Phase III Trial", Arthritis & Rheumatism, 2005, 52(2):582-591.
ClinicalTrials.gov Archive, NCT00809614 Apr. 29, 2010.
ClinicalTrials.gov Archive, NCT01169844, Jul. 23, 2010.
Science Translational Medicine, Oct. 1, 2010 vol. 2, N52/Article No. 52RA72, pp. 1-9.
Press Release of Novarts dated Oct. 24, 2011, D10-Press release of Novartis.pdf, Other-evidence-4.pdf.
ClinicalTrials.gov, NCT01359943, printout of https://clinicaltrials.gov/ct2/history/NCT01359943?V2=View#StudyPageTop, Oct. 18, 2011.
ClinicalTrials.gov, NCT01649375, (MEASURE 2), printout of https://clinicaltrials.gov/ct2/show/NCT01649375(post-published).
Baeten et al., "The Anti-IL17A Monoclonal Antibody Secukinumab (AIN457) showed good safety and efficacy in the treatment of active ankylosing spondylitis", Annals of the Rheumatic Diseases, vol. 70, No. 3, Abstract #OP0174, p. 127 (oral presentation at EULAR 2011 meeting May 25-28, 2011).
Cimzia (Ref TM) (certolizumab pegol) FDA label dated Jul. 2010.
Genovese et al., "Secukinumab (AIN457), a novel monoclonal antibody targeting IL-17A demonstrates efficacy in active rheumatoid arthritis patients despite stable methotrexate treatment results of a phase IIb study", Arthritis & Rheumatism, 2010, 62(12):Abstract #L9, p. 3842.
Genovese et al., "Secukinumab (AIN457) showed a rapid decrease activity in patients with active rheumatoid arthritis patients including those with high inflammatory burden", Annals of the Rheumatic Diseases, vol. 70, No. 3 Abstract #FRI0380, p. 472 (poster presentation at EULAR 2011 meeting May 25-28, 2011).
Ness, (Sep. 12, 2011) "Surveying the pipeline of biologics to treat inflammatory conditions", Pharmacy Times, Aug. 2011; printout of https://www.pharmacytimes.com/publications/issue/2011/august2011/surveying-the-pipeline-of-biologics-to-treat-inflammatory-conditions.
ClinicalTrials.gov, NCT01358175 (MEASURE1), printout of https://clinicaltrials.gov/ct2/history/NCT01358175?V2=View#StudyPageTop, Oct. 20, 2011.
Press Release of Novartis dated Oct. 24, 2011, print out of https://www.foxnews.com/health/study-drug-helps-with-psoriasis-symptoms.

(56) References Cited

OTHER PUBLICATIONS

Inman et al., "Efficacy and Safety of Gollmumab in Patients With Ankylosing SPondylitis", Arthritis & Rheumatism, 2008, 58(11):34020-3412.
Van der Heijde et al., "Efficacy and Safety of Infliximab in Patients with Ankylosing Spondylitis", Arthritis & Rheumatism, 2005, 52(2):582-591.
Van der Heijde et al., "Efficacy and Safety of Adalimumab in Patients with Ankylosing Spondylitis", Arthritis & Rheumatism, 2006, 54(7):2136-2146.
Song et al., "Different Response to Rituximab in Tumor Necrosis Factor Blocker-Naive Patients with Active Ankylosing Spondylitis and in Patients in Whom Tumor Necrosis Factor Blockers Have Failed", Arthritis & Rheumatism, 2010, 62 (5):1290-1297.
Halibel et al., "Open label trial of anakinra in active ankylosing spondylitis over 24 weeks", Ann Rheum Dios, 2005, 64:296-298.
Song et al., "Treatment of active ankylosing spondylitis with abatacept: an open-label, 24-week pilot study", Ann Rheum Dis, 2011, 70:1108-1110.
Sieper et al., "Assessnebt if short-term symptomatic efficacy of tocilizumab in ankylosing spondylitis: results of randomised, placebo-controlled trials", Ann Rheum Dis, 2014, 73:95-100.
Sieper et al., "Sarilumab for the treatment of ankylosing spondylitis: results of a Phase II, randomised, double-blind, placebo-controlled study (ALIGN)", Ann Rheum Dis, 2015, 74:1051-1057.
Dougados and Baeten, "Spondyloarthritis", Lancet, 2011, 377:2127-2137.
Braun et al., "2010 update of the ASAS/EULAR recommendations for the management of ankylosing spondylitis", Ann Rheum Dis, 2011, 70:896-904.
Landews et al., "Efficacy of certolizumab pegol on signs and symptoms of axial spondyloarthritis including ankylosing spondylitis: 24-week results of a double-blind, randomised, placebo-controlled Phase 3 study", Ann Rheum Dis, 2014, 73:39-47.
Kagen et al., "Subcultaneous Absorption of Monoclonal Antibodies: Role of Dose, Site of Injection, and Injection Volume on Rituximab Pharmacokinetics in Rats", Pharm Res, 2012, 18:490-499.
Zhao et al., "The Antibody Drug Absorption Following Subcutaneous or Intramuscular Administration and Its Mathematical Description by Coupling Physiologically Based Absorption Process with the Conventional Compartment Pharmacokinetic Model", The Journal of Clinical Pharmacology, 2013, 53(3):314-325.
Tang et al., "Pharmacokinetic Aspects of Biotechnology Products", Journal of Pharmaceutical Sciences, 2004, 93 (9):2184-2204.
Richter et al., "Mechanistic Determinants of Biotherapeutics Absorption Following SC Administration". The AAPS Journal, 2012, 14(3).
TAMIFLU(TM)(oseltamivir phosphate) Capsules and for Oal Suspension Package insert, Rev, Jan. 2008.
MALARONE Package insert, Revised, Jun. 2013.
Maksymowych et al., "Secukinumab for the treatment of ankylosing spondylitis: comparative effectiveness results versus adalimumab using a matching-adjusted indirect comparison", Absrtact OP114 presented at the 25th European League Against Rheumatism Congress, 2016, Jun. 8-11, London, downloaded Jun. 13, 2016, available at https://www.rheuma-schweiz.ch/index.php?id=692 [(2016) Ann Rheum Dis 75(Suppl2):98].
Nash et al., Secukinumab for psoriatic arthritis: comparative effectiveness results versus etanercept up to 24 weeks using a matching-adjusted indirect comparison, International Journal of Rheumatic Diseases, 2016, 19(Suppl. 2):21-293 pp. 244-245.
Declaration of Diane Mould, dated Jan. 29, 2014, filed in U.S. Appl. No. 10/163,657, filed Feb. 7, 2014.
Menter et al., "Guidelines of care for the management of psoriasis and psoriatic arthritis", J Am Acad Dermatol 2011, pp. 137-174.
Gossec et al., "European League Against Rheumatism recommendations for the management of psoriatic arthritis with pharmacological therapies", Ann Rheum Dis, 2012, 71:4-12.

Fig. 12

<table>
<tr><td rowspan="2">Experimental</td><td>Induction<br><br>Average $C_{max}$ 401 μg/ml at end of third 10 mg/kg i.v. infusion for a 90 kg human ( 30%-40% inter-patient variation)</td></tr>
<tr><td>Maintenance (75, 150 or 300 mg s.c. monthly)<br><br>Average steady-state trough levels for a 75 kg human (30% inter-patient variation):<br>9.4 μg/ml (e.g., 75 mg dose)<br>17.3 μg/ml (e.g., 150 mg dose)<br>31 μg/ml (e.g., 300 mg dose)<br><br>AUC tau ranges at steady state:<br>314 mg*day/L (e.g., 75 mg dose)<br>628 mg*day/L (e.g., 150 mg dose)<br>1256 mg*day/L (e.g., 300 mg dose)</td></tr>
<tr><td rowspan="2">Simulated</td><td>Induction<br><br>Average $C_{max}$ 240 μg/ml after the first dose and 360 μg/ml after the third i.v. infusion for a 75 kg human. Trough levels maintained above 80 μg/ml over a 10 week period.</td></tr>
<tr><td>Maintenance (75, 150 or 300 mg s.c. monthly beginning week 8)<br><br>Average steady-state trough levels for a 75 kg human:<br>8.0 μg/ml (e.g., 75 mg dose)<br>17 μg/ml (e.g., 150 mg dose)<br>30 μg/ml (e.g., 300 mg dose)<br><br>AUC tau (mg*day/L) at steady state (The q025 and q975 give the AUC range having 95% of the patients):<br><br>
<table>
<tr><th>dose</th><th>$Auc_{mean}$</th><th>$AUC_{median}$</th><th>$AUC_{q025}$</th><th>$AUC_{q975}$</th></tr>
<tr><td>75</td><td>331</td><td>309</td><td>128</td><td>657</td></tr>
<tr><td>150</td><td>661</td><td>618</td><td>257</td><td>1315</td></tr>
<tr><td>300</td><td>1323</td><td>1237</td><td>513</td><td>2629</td></tr>
</table>
</td></tr>
</table>

SEQUENCE LISTING

<160> NUMBER OF SEQ ID NOS: 17

<210> SEQ ID NO 1
<211> LENGTH: 5
<212> TYPE: PRT
<213> ORGANISM: artificial
<220> FEATURE:
<223> OTHER INFORMATION: CDR1 = hypervariable region 1 of heavy chain of AIN457

<400> SEQUENCE: 1

```
Asn Tyr Trp Met Asn
1               5
```

<210> SEQ ID NO 2
<211> LENGTH: 17
<212> TYPE: PRT
<213> ORGANISM: ARTIFICIAL
<220> FEATURE:
<223> OTHER INFORMATION: CDR2 = hypervariable region 2 of heavy chain of AIN457

<400> SEQUENCE: 2

```
Ala Ile Asn Gln Asp Gly Ser Glu Lys Tyr Tyr Val Gly Ser Val Lys
1               5                   10                  15

Gly
```

<210> SEQ ID NO 3
<211> LENGTH: 18
<212> TYPE: PRT
<213> ORGANISM: ARTIFICIAL
<220> FEATURE:
<223> OTHER INFORMATION: CDR3 = hypervariable region 3 of heavy chain of AIN457

<400> SEQUENCE: 3

```
Asp Tyr Tyr Asp Ile Leu Thr Asp Tyr Tyr Ile His Tyr Trp Tyr Phe
1               5                   10                  15

Asp Leu
```

<210> SEQ ID NO 4
<211> LENGTH: 12
<212> TYPE: PRT
<213> ORGANISM: ARTIFICIAL
<220> FEATURE:
<223> OTHER INFORMATION: CDR1' = hypervariable region 1 of light chain of AIN457

<400> SEQUENCE: 4

```
Arg Ala Ser Gln Ser Val Ser Ser Ser Tyr Leu Ala
1               5                   10
```

<210> SEQ ID NO 5
<211> LENGTH: 7
<212> TYPE: PRT
<213> ORGANISM: ARTIFICIAL
<220> FEATURE:
<223> OTHER INFORMATION: CDR2' = hypervariable region 2 of light chain AIN457

<400> SEQUENCE: 5

```
Gly Ala Ser Ser Arg Ala Thr
1               5
```

<210> SEQ ID NO 6
<211> LENGTH: 9

```
<212> TYPE: PRT
<213> ORGANISM: ARTIFICIAL
<220> FEATURE:
<223> OTHER INFORMATION: CDR3' = hypervariable region 3 of light chain
      AIN457

<400> SEQUENCE: 6

Gln Gln Tyr Gly Ser Ser Pro Cys Thr
1               5


<210> SEQ ID NO 7
<211> LENGTH: 381
<212> TYPE: DNA
<213> ORGANISM: HOMO SAPIENS
<220> FEATURE:
<221> NAME/KEY: CDS
<222> LOCATION: (1)..(381)

<400> SEQUENCE: 7

gag gtg cag ttg gtg gag tct ggg gga ggc ttg gtc cag cct ggg ggg       48
Glu Val Gln Leu Val Glu Ser Gly Gly Gly Leu Val Gln Pro Gly Gly
1               5                   10                  15

tcc ctg aga ctc tcc tgt gca gcc tct gga ttc acc ttt agt aac tat       96
Ser Leu Arg Leu Ser Cys Ala Ala Ser Gly Phe Thr Phe Ser Asn Tyr
            20                  25                  30

tgg atg aac tgg gtc cgc cag gct cca ggg aaa ggg ctg gag tgg gtg      144
Trp Met Asn Trp Val Arg Gln Ala Pro Gly Lys Gly Leu Glu Trp Val
        35                  40                  45

gcc gcc ata aac caa gat gga agt gag aaa tac tat gtg ggc tct gtg      192
Ala Ala Ile Asn Gln Asp Gly Ser Glu Lys Tyr Tyr Val Gly Ser Val
    50                  55                  60

aag ggc cga ttc acc atc tcc aga gac aac gcc aag aac tca ctg tat      240
Lys Gly Arg Phe Thr Ile Ser Arg Asp Asn Ala Lys Asn Ser Leu Tyr
65                  70                  75                  80

ctg caa atg aac agc ctg aga gtc gag gac acg gct gtg tat tac tgt      288
Leu Gln Met Asn Ser Leu Arg Val Glu Asp Thr Ala Val Tyr Tyr Cys
                85                  90                  95

gtg agg gac tat tac gat att ttg acc gat tat tac atc cac tat tgg      336
Val Arg Asp Tyr Tyr Asp Ile Leu Thr Asp Tyr Tyr Ile His Tyr Trp
            100                 105                 110

tac ttc gat ctc tgg ggc cgt ggc acc ctg gtc act gtc tcc tca          381
Tyr Phe Asp Leu Trp Gly Arg Gly Thr Leu Val Thr Val Ser Ser
        115                 120                 125


<210> SEQ ID NO 8
<211> LENGTH: 127
<212> TYPE: PRT
<213> ORGANISM: HOMO SAPIENS

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Ala Ile Asn Gln Asp Gly Ser Glu Lys Tyr Tyr Val Gly Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Glu Asp Thr Ala Val Tyr Tyr Cys
                85                  90                  95
```

```
Val Arg Asp Tyr Tyr Asp Ile Leu Thr Asp Tyr Tyr Ile His Tyr Trp
            100                 105                 110

Tyr Phe Asp Leu Trp Gly Arg Gly Thr Leu Val Thr Val Ser Ser
        115                 120                 125


<210> SEQ ID NO 9
<211> LENGTH: 327
<212> TYPE: DNA
<213> ORGANISM: HOMO SAPIENS
<220> FEATURE:
<221> NAME/KEY: CDS
<222> LOCATION: (1)..(327)

<400> SEQUENCE: 9

gaa att gtg ttg acg cag tct cca ggc acc ctg tct ttg tct cca ggg       48
Glu Ile Val Leu Thr Gln Ser Pro Gly Thr Leu Ser Leu Ser Pro Gly
1               5                   10                  15

gaa aga gcc acc ctc tcc tgc agg gcc agt cag agt gtt agc agc agc       96
Glu Arg Ala Thr Leu Ser Cys Arg Ala Ser Gln Ser Val Ser Ser Ser
            20                  25                  30

tac tta gcc tgg tac cag cag aaa cct ggc cag gct ccc agg ctc ctc      144
Tyr Leu Ala Trp Tyr Gln Gln Lys Pro Gly Gln Ala Pro Arg Leu Leu
        35                  40                  45

atc tat ggt gca tcc agc agg gcc act ggc atc cca gac agg ttc agt      192
Ile Tyr Gly Ala Ser Ser Arg Ala Thr Gly Ile Pro Asp Arg Phe Ser
    50                  55                  60

ggc agt ggg tct ggg aca gac ttc act ctc acc atc agc aga ctg gag      240
Gly Ser Gly Ser Gly Thr Asp Phe Thr Leu Thr Ile Ser Arg Leu Glu
65                  70                  75                  80

cct gaa gat ttt gca gtg tat tac tgt cag cag tat ggt agc tca ccg      288
Pro Glu Asp Phe Ala Val Tyr Tyr Cys Gln Gln Tyr Gly Ser Ser Pro
                85                  90                  95

tgc acc ttc ggc caa ggg aca cga ctg gag att aaa cga                  327
Cys Thr Phe Gly Gln Gly Thr Arg Leu Glu Ile Lys Arg
            100                 105


<210> SEQ ID NO 10
<211> LENGTH: 109
<212> TYPE: PRT
<213> ORGANISM: HOMO SAPIENS

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Cys Thr Phe Gly Gln Gly Thr Arg Leu Glu Ile Lys Arg
            100                 105


<210> SEQ ID NO 11
<211> LENGTH: 10
<212> TYPE: PRT
```

```
<213> ORGANISM: artificial
<220> FEATURE:
<223> OTHER INFORMATION: CDR1-x = hypervariable domain x of heavy chain
      of AIN457

<400> SEQUENCE: 11

Gly Phe Thr Phe Ser Asn Tyr Trp Met Asn
1               5                   10


<210> SEQ ID NO 12
<211> LENGTH: 11
<212> TYPE: PRT
<213> ORGANISM: artificial
<220> FEATURE:
<223> OTHER INFORMATION: CDR2-x = hypervariable domain of heavy chain x
      of AIN457

<400> SEQUENCE: 12

Ala Ile Asn Gln Asp Gly Ser Glu Lys Tyr Tyr
1               5                   10


<210> SEQ ID NO 13
<211> LENGTH: 23
<212> TYPE: PRT
<213> ORGANISM: ARTIFICIAL
<220> FEATURE:
<223> OTHER INFORMATION: CDR3-x = hypervariable domain x of heavy chain
      AIN457

<400> SEQUENCE: 13

Cys Val Arg Asp Tyr Tyr Asp Ile Leu Thr Asp Tyr Tyr Ile His Tyr
1               5                   10                  15

Trp Tyr Phe Asp Leu Trp Gly
            20


<210> SEQ ID NO 14
<211> LENGTH: 711
<212> TYPE: DNA
<213> ORGANISM: homo sapiens
<220> FEATURE:
<221> NAME/KEY: CDS
<222> LOCATION: (1)..(708)

<400> SEQUENCE: 14

acc atg gaa acc cca gcg gag ctt ctc ttc ctc ctg cta ctc tgg ctc       48
Thr Met Glu Thr Pro Ala Glu Leu Leu Phe Leu Leu Leu Leu Trp Leu
1               5                   10                  15

cca gat acc acc gga gaa att gtg ttg acg cag tct cca ggc acc ctg       96
Pro Asp Thr Thr Gly Glu Ile Val Leu Thr Gln Ser Pro Gly Thr Leu
            20                  25                  30

tct ttg tct cca ggg gaa aga gcc acc ctc tcc tgc agg gcc agt cag      144
Ser Leu Ser Pro Gly Glu Arg Ala Thr Leu Ser Cys Arg Ala Ser Gln
        35                  40                  45

agt gtt agc agc agc tac tta gcc tgg tac cag cag aaa cct ggc cag      192
Ser Val Ser Ser Ser Tyr Leu Ala Trp Tyr Gln Gln Lys Pro Gly Gln
    50                  55                  60

gct ccc agg ctc ctc atc tat ggt gca tcc agc agg gcc act ggc atc      240
Ala Pro Arg Leu Leu Ile Tyr Gly Ala Ser Ser Arg Ala Thr Gly Ile
65                  70                  75                  80

cca gac agg ttc agt ggc agt ggg tct ggg aca gac ttc act ctc acc      288
Pro Asp Arg Phe Ser Gly Ser Gly Ser Gly Thr Asp Phe Thr Leu Thr
                85                  90                  95

atc agc aga ctg gag cct gaa gat ttt gca gtg tat tac tgt cag cag      336
Ile Ser Arg Leu Glu Pro Glu Asp Phe Ala Val Tyr Tyr Cys Gln Gln
            100                 105                 110
```

```
tat ggt agc tca ccg tgc acc ttc ggc caa ggg aca cga ctg gag att      384
Tyr Gly Ser Ser Pro Cys Thr Phe Gly Gln Gly Thr Arg Leu Glu Ile
        115                 120                 125

aaa cga act gtg gct gca cca tct gtc ttc atc ttc ccg cca tct gat      432
Lys Arg Thr Val Ala Ala Pro Ser Val Phe Ile Phe Pro Pro Ser Asp
    130                 135                 140

gag cag ttg aaa tct gga act gcc tct gtt gtg tgc ctg ctg aat aac      480
Glu Gln Leu Lys Ser Gly Thr Ala Ser Val Val Cys Leu Leu Asn Asn
145                 150                 155                 160

ttc tat ccc aga gag gcc aaa gta cag tgg aag gtg gat aac gcc ctc      528
Phe Tyr Pro Arg Glu Ala Lys Val Gln Trp Lys Val Asp Asn Ala Leu
                165                 170                 175

caa tcg ggt aac tcc cag gag agt gtc aca gag cag gac agc aag gac      576
Gln Ser Gly Asn Ser Gln Glu Ser Val Thr Glu Gln Asp Ser Lys Asp
            180                 185                 190

agc acc tac agc ctc agc agc acc ctg acg ctg agc aaa gca gac tac      624
Ser Thr Tyr Ser Leu Ser Ser Thr Leu Thr Leu Ser Lys Ala Asp Tyr
        195                 200                 205

gag aaa cac aaa gtc tac gcc tgc gaa gtc acc cat cag ggc ctg agc      672
Glu Lys His Lys Val Tyr Ala Cys Glu Val Thr His Gln Gly Leu Ser
    210                 215                 220

tcg ccc gtc aca aag agc ttc aac agg gga gag tgt tag                  711
Ser Pro Val Thr Lys Ser Phe Asn Arg Gly Glu Cys
225                 230                 235


<210> SEQ ID NO 15
<211> LENGTH: 236
<212> TYPE: PRT
<213> ORGANISM: homo sapiens

<400> SEQUENCE: 15

Thr Met Glu Thr Pro Ala Glu Leu Leu Phe Leu Leu Leu Leu Trp Leu
1               5                   10                  15

Pro Asp Thr Thr Gly Glu Ile Val Leu Thr Gln Ser Pro Gly Thr Leu
            20                  25                  30

Ser Leu Ser Pro Gly Glu Arg Ala Thr Leu Ser Cys Arg Ala Ser Gln
        35                  40                  45

Ser Val Ser Ser Ser Tyr Leu Ala Trp Tyr Gln Gln Lys Pro Gly Gln
    50                  55                  60

Ala Pro Arg Leu Leu Ile Tyr Gly Ala Ser Ser Arg Ala Thr Gly Ile
65                  70                  75                  80

Pro Asp Arg Phe Ser Gly Ser Gly Ser Gly Thr Asp Phe Thr Leu Thr
                85                  90                  95

Ile Ser Arg Leu Glu Pro Glu Asp Phe Ala Val Tyr Tyr Cys Gln Gln
            100                 105                 110

Tyr Gly Ser Ser Pro Cys Thr Phe Gly Gln Gly Thr Arg Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205
```

```
Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235


<210> SEQ ID NO 16
<211> LENGTH: 783
<212> TYPE: DNA
<213> ORGANISM: homo sapiens
<220> FEATURE:
<221> NAME/KEY: CDS
<222> LOCATION: (1)..(780)

<400> SEQUENCE: 16

acc atg gaa ttg ggg ctg agc tgg gtt ttc ctt gtt gct att tta gaa       48
Thr Met Glu Leu Gly Leu Ser Trp Val Phe Leu Val Ala Ile Leu Glu
1               5                   10                  15

ggt gtc cac tgt gag gtg cag ttg gtg gag tct ggg gga ggc ttg gtc       96
Gly Val His Cys Glu Val Gln Leu Val Glu Ser Gly Gly Gly Leu Val
            20                  25                  30

cag cct ggg ggg tcc ctg aga ctc tcc tgt gca gcc tct gga ttc acc      144
Gln Pro Gly Gly Ser Leu Arg Leu Ser Cys Ala Ala Ser Gly Phe Thr
        35                  40                  45

ttt agt aac tat tgg atg aac tgg gtc cgc cag gct cca ggg aaa ggg      192
Phe Ser Asn Tyr Trp Met Asn Trp Val Arg Gln Ala Pro Gly Lys Gly
    50                  55                  60

ctg gag tgg gtg gcc gcc ata aac caa gat gga agt gag aaa tac tat      240
Leu Glu Trp Val Ala Ala Ile Asn Gln Asp Gly Ser Glu Lys Tyr Tyr
65                  70                  75                  80

gtg ggc tct gtg aag ggc cga ttc acc atc tcc aga gac aac gcc aag      288
Val Gly Ser Val Lys Gly Arg Phe Thr Ile Ser Arg Asp Asn Ala Lys
                85                  90                  95

aac tca ctg tat ctg caa atg aac agc ctg aga gtc gag gac acg gct      336
Asn Ser Leu Tyr Leu Gln Met Asn Ser Leu Arg Val Glu Asp Thr Ala
            100                 105                 110

gtg tat tac tgt gtg agg gac tat tac gat att ttg acc gat tat tac      384
Val Tyr Tyr Cys Val Arg Asp Tyr Tyr Asp Ile Leu Thr Asp Tyr Tyr
        115                 120                 125

atc cac tat tgg tac ttc gat ctc tgg ggc cgt ggc acc ctg gtc act      432
Ile His Tyr Trp Tyr Phe Asp Leu Trp Gly Arg Gly Thr Leu Val Thr
    130                 135                 140

gtc tcc tca gcc tcc acc aag ggc cca tcg gtc ttc ccc ctg gca ccc      480
Val Ser Ser Ala Ser Thr Lys Gly Pro Ser Val Phe Pro Leu Ala Pro
145                 150                 155                 160

tcc tcc aag agc acc tct ggg ggc aca gcg gcc ctg ggc tgc ctg gtc      528
Ser Ser Lys Ser Thr Ser Gly Gly Thr Ala Ala Leu Gly Cys Leu Val
                165                 170                 175

aag gac tac ttc ccc gaa ccg gtg acg gtg tcg tgg aac tca ggc gcc      576
Lys Asp Tyr Phe Pro Glu Pro Val Thr Val Ser Trp Asn Ser Gly Ala
            180                 185                 190

ctg acc agc ggc gtg cac acc ttc ccg gct gtc cta cag tcc tca gga      624
Leu Thr Ser Gly Val His Thr Phe Pro Ala Val Leu Gln Ser Ser Gly
        195                 200                 205

ctc tac tcc ctc agc agc gtg gtg acc gtg ccc tcc agc agc ttg ggc      672
Leu Tyr Ser Leu Ser Ser Val Val Thr Val Pro Ser Ser Ser Leu Gly
    210                 215                 220

acc cag acc tac atc tgc aac gtg aat cac aag ccc agc aac acc aag      720
Thr Gln Thr Tyr Ile Cys Asn Val Asn His Lys Pro Ser Asn Thr Lys
225                 230                 235                 240

gtg gac aag aga gtt gag ccc aaa tct tgt gac aaa act cac aca tgc      768
```

-continued

```
Val Asp Lys Arg Val Glu Pro Lys Ser Cys Asp Lys Thr His Thr Cys
                245                 250                 255

cca ccg tgc cca taa                                               783
Pro Pro Cys Pro
            260


<210> SEQ ID NO 17
<211> LENGTH: 260
<212> TYPE: PRT
<213> ORGANISM: homo sapiens

<400> SEQUENCE: 17

Thr Met Glu Leu Gly Leu Ser Trp Val Phe Leu Val Ala Ile Leu Glu
1               5                   10                  15

Gly Val His Cys Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Asn Tyr Trp Met Asn Trp Val Arg Gln Ala Pro Gly Lys Gly
    50                  55                  60

Leu Glu Trp Val Ala Ala Ile Asn Gln Asp Gly Ser Glu Lys Tyr Tyr
65                  70                  75                  80

Val Gly Ser Val Lys Gly Arg Phe Thr Ile Ser Arg Asp Asn Ala Lys
                85                  90                  95

Asn Ser Leu Tyr Leu Gln Met Asn Ser Leu Arg Val Glu Asp Thr Ala
            100                 105                 110

Val Tyr Tyr Cys Val Arg Asp Tyr Tyr Asp Ile Leu Thr Asp Tyr Tyr
        115                 120                 125

Ile His Tyr Trp Tyr Phe Asp Leu Trp Gly Arg Gly Thr Leu Val Thr
    130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
    210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Asp Lys Thr His Thr Cys
                245                 250                 255

Pro Pro Cys Pro
            260
```

METHODS OF TREATING INFLAMMATORY ARTHRITIS USING SECUKINUMAB

TECHNICAL FIELD

The disclosure relates to novel methods for treating arthritis, which employ a therapeutically effective amount of an IL-17 binding molecule, e.g., an IL-17 antibody, such as the AIN457 antibody (which is also known as "secukinumab").

BACKGROUND OF THE DISCLOSURE

Rheumatoid arthritis (RA) is a chronic, inflammatory, systemic autoimmune disease of unknown etiology. It is characterized by symmetric synovitis leading to cartilage damage and joint destruction and can be complicated by numerous extra-articular manifestations. Given the presence of autoantibodies, such as rheumatoid factor (RF) and anti-citrullinated protein antibody (ACPA), RA is considered an autoimmune disease. RA is generally a progressive disease with functional status decline, significant morbidity and premature mortality seen in established RA. The disease can occur at any age, with a peak incidence between the fourth and sixth decades. The goal of long-term RA treatment is disease remission.

Disease-modifying antirheumatic drugs (DMARDs), a heterogenous collection of agents grouped by use and convention, are the first line of treatment for RA patients. DMARDs are used to reduce joint swelling and pain, decrease acute-phase markers, limit the progression of joint damage and to improve joint function. DMARDs, most often methotrexate (MTX), are prescribed upon disease diagnosis (i.e., early RA), usually before the development of erosive disease and the deformities seen in established RA. MTX therapy is initiated if pain and synovitis persist (especially if function is compromised), and additional DMARDs (with or without steroids) may be added to achieve disease control. Unfortunately, only about ⅔ of patients respond to DMARDS, and DMARDs only partially control established RA disease. Radiological progression continues even in the 5-20% of DMARD-treated RA patients that achieve remission or clinical improvement that approaches remission. DMARDS also have many adverse effects (e.g., liver damage, bone marrow suppression and severe lung infection) that limit their prolonged use.

Due to the inadequate responses and dangers associated with prolonged DMARD treatment, biologics have been introduced as second line RA treatments. In general, anti-TNF agents (Cimzia®, Enbrel®, Humira®, Remicade®, Simponi®) are the first biologics used in DMARD-failure and DMARD-inadequate responder patients, and a TNF inhibitor is often combined with MTX (or another DMARD) to aggressively treat established RA. Unfortunately, 30-40% of patients with established RA fail to respond to TNF-α antagonists and the majority of those that respond initially do not achieve complete remission or lose response over time. Concerns have also been raised about the short and long-term tolerability and safety of chronic biologic treatment, most notably the reactivation of serious infections (e.g., tuberculosis infections), liver toxicity, increased cardiovascular disease, induction (or exacerbation of) demyelinating conditions, and increased incidence of malignancy due to TNF-alpha antagonism. M. Khraishi (2009) J. Rheumatol Suppl. 82:25-32; Salliot et al. (2009) Ann. Rheum. Dis. 68:25-32. However, a TNF inhibitor is usually continued unless it becomes ineffective or an adverse event arises, at which point a clinician may switch to either a different TNF inhibitor or a biological with a different mechanism of action (e.g., Kineret® [IL-1R antagonist], MabThera® [CD20 antagonist], Orencia® [CTLA4 fusion protein] or Actemra® [IL-6 receptor antagonist]). Scott et al. (2010) The Lancet 376:1095-1108.

Given the aforementioned problems with current RA therapy, there is a need to develop new treatments for RA patients.

SUMMARY OF THE DISCLOSURE

Secukinumab, a new biological in clinical development for RA, is a high-affinity fully human monoclonal anti-human antibody that inhibits Interleukin-17A activity. In an RA proof-of-concept (PoC) study, patients with active RA who were on a stable dose of MTX were dosed in rising single and then 2 doses (21 days apart) with secukinumab at 1 mg/kg, 3 mg/kg and 10 mg/kg intravenously. Hueber et al. (2010) Sci. Transl. Med. 2(52):52-72. Treatment with secukinumab resulted in rapid improvement of the clinical manifestations of RA in many patients compared to placebo. These data provide evidence that neutralization of IL-17A is likely to be efficacious in RA patients with active RA. However, since patient response to biological treatment is variable and it is desirable to avoid providing drug to patients who will be resistant thereto, we have sought methods of treating RA that first identity those patients most likely to respond favorably to antagonism of IL-17. We have identified an RA subgroup having patients that display an improved likelihood of responding to IL-17 antagonism, whom we have named "high risk RA patients".

Thus, it is one object of the disclosure to provide methods of identifying and treating "high risk RA patients" using a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof).

It is another object of the disclosure to provide methods of determining the likelihood that an RA patient will respond to treatment with an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof), by determining whether that patient is a high risk RA patient.

It is another object of the disclosure to provide methods of treating an inflammatory arthritis, e.g., AS, RA and PsA, using a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof), by delivering such IL-7 antagonist as part of a therapeutic regimen, e.g., during an induction regimen and a maintenance regimen.

Accordingly, disclosed herein are methods of treating rheumatoid arthritis (RA), comprising administering a therapeutically effective amount of an IL-17 antagonist to a high risk RA patient.

Disclosed herein are also methods of treating rheumatoid arthritis (RA), comprising: a) selecting a patient for treatment on the basis of the patient being a high risk RA patient; and b) administering a therapeutically effective amount of an IL-17 antagonist to the patient.

Disclosed herein are methods of treating rheumatoid arthritis (RA), comprising: a) assaying a sample from a patient for: i. rheumatoid factor (RF), anti-citrullinated protein antibody (ACPA), or RF and ACPA; and ii. C-reactive protein (CRP), an erythrocyte sedimentation rate (ESR), or both CRP and an ESR; and b) thereafter, administering the patient an IL-17 antagonist to the patient if the patient is RF+, ACPA+, or RF+ and ACPA+ and the patient has a high level of CRP, a high ESR, or a high level of CRP and a high ESR.

Disclosed herein are methods of treating rheumatoid arthritis (RA), comprising administering a therapeutically effective amount of an IL-17 antagonist to a patient, provided that the patient is selected for treatment on the basis of: a) being RF+, ACPA+, or both RF+ and ACPA+; and b) having a high level of CRP, a high ESR, or both a high level of CRP and a high ESR. In some embodiments, the step of administering comprises: a) administering the IL-17 antagonist to the patient during an induction regimen; and b) thereafter administering the IL-17 antagonist to the patient during a maintenance regimen.

Disclosed herein are methods of treating rheumatoid arthritis (RA), comprising: a) administering a high risk RA patient three doses of about 10 mg/kg of an IL-17 antagonist, each of the three doses being delivered every other week; and b) thereafter administering about 75 mg-about 150 mg of the IL-17 antagonist to the patient every month, beginning one month from delivery of the third intravenous dose.

Disclosed herein are therapeutic regimens for treating rheumatoid arthritis (RA), comprising: a) selecting a patient having RA based on the following criteria; i. the patient is RF+, ACPA+, or both RF+ and ACPA+; and ii. the patient has a high level of CRP, a high ESR, or both a high level of CRP and a high ESR; and b) administering the patient three doses of about 10 mg/kg of an IL-17 antagonist, the first dose being delivered during week zero, the second dose being delivered during week two, and the third dose being delivered during week four; and c) thereafter administering the patient about 75 mg-about 150 mg of the IL-17 antagonist twice a month, monthly, every two months or every three months, beginning during week eight.

Disclosed herein are methods of determining the likelihood that an RA patient will respond to treatment with an IL-17 antagonist, comprising assaying a sample from the patient for: a) rheumatoid factor (RF), anti-citrullinated protein antibody (ACPA), or RF and ACPA; and b) C-reactive protein (CRP), an erythrocyte sedimentation rate (ESR), or both CRP and an ESR, wherein the patient is likely to respond to treatment of RA with the IL-17 antagonist if the patient is RF+, ACPA+, or RF+ and ACPA+; and the patient has a high level of CRP, a high ESR, or a high level of CRP and a high ESR.

Disclosed herein are IL-17 antagonists for use in treating rheumatoid arthritis (RA), characterized in that the IL-17 antagonist is to be administered to a high risk RA patient. Disclosed herein are IL-17 antagonists for use in treating rheumatoid arthritis (RA), characterized in that the IL-17 antagonist is to be administered to a patient selected for treatment on the basis of the patient being a high risk RA patient.

Disclosed herein are IL-17 antagonists for use in treating a high risk RA patient. In some embodiments, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR. In some embodiments, a high level of CRP is ≥10 mg/L, as measured by hsCRP. In some embodiments, a high ESR is ≥28 mm/h.

Disclosed herein are IL-17 antagonists for use in treating rheumatoid arthritis (RA), characterized in that the IL-17 antagonist is to be administered to a patient, provided that the patient is selected for treatment on the basis of: a) being RF+, ACPA+, or both RF+ and ACPA+; and b) having a high level of CRP, a high ESR, or both a high level of CRP and a high ESR.

Disclosed herein are IL-17 antagonists for use in treating rheumatoid arthritis (RA), characterized in that the IL-17 antagonist is to be: a) administered to a high risk RA patient as three doses of about 10 mg/kg, each of the three doses being delivered every other week; and b) thereafter administered to the patient as a dose of about 75 mg-about 150 mg every month, beginning one month from delivery of the third intravenous dose.

Disclosed herein are IL-17 antagonists for use in treating rheumatoid arthritis (RA), characterized in that: a) a sample from a patient is assayed for: i. rheumatoid factor (RF), anti-citrullinated protein antibody (ACPA), or RF and ACPA; and ii. C-reactive protein (CRP), an erythrocyte sedimentation rate (ESR), or both CRP and an ESR; and b) the IL-17 antagonist is administered to the patient if the patient is RF+, ACPA+, or RF+ and ACPA+ and the patient has a high level of CRP, a high ESR, or a high level of CRP and a high ESR.

Disclosed herein are uses of an IL-17 antagonist for the manufacture of a medicament for treating RA, characterized in that the IL-17 antagonist is to be administered to high risk RA patient.

Disclosed herein are uses of an IL-17 antagonist for the manufacture of a medicament for treating RA, characterized in that the IL-17 antagonist is to be administered to high risk RA patient during an induction regimen followed by a maintenance regimen.

Disclosed herein are pharmaceutical composition for treating RA, comprising as an active ingredient an IL-17 antagonist, wherein the IL-17 antagonist is to be administered to a high risk RA patient.

Disclosed herein are pharmaceutical composition for treating RA, comprising as an active ingredient an IL-17 antagonist, wherein the IL-17 antagonist is to be administered to a high risk RA patient during an induction regimen followed by a maintenance regimen.

Disclosed herein are therapeutic regimens for treating RA, comprising: a) selecting a high risk RA patient; b) administering about 10 mg/kg of an IL-17 antagonist to the patient during weeks 0, 2 and 4; and c) thereafter administering about 75 mg-about 150 mg of the IL-17 antagonist to the patient monthly, beginning week 8.

Disclosed herein are methods of treating a RA patient or a high risk RA patient, comprising: a) administering an IL-17 binding molecule to a patient in need thereof during an induction regimen that provides a mean maximum plasma concentration ($C_{max}$) of the IL-17 binding molecule of about 360 μg/ml; and b) thereafter administering the IL-17 binding molecule to the patient during a maintenance regimen that provides: i) an average steady-state trough level of the IL-17 binding molecule between about 8 μg/ml-about 30 μg/ml; and/or ii) a mean AUC tau at steady state of about 331 mg*day/L-about 1323 mg*day/L.

Disclosed herein are IL-17 binding molecules for use in treating a RA patient or a high risk RA patient, characterized in that the IL-17 binding molecule: a) is to be administered to the patient during an induction regimen that provides a mean maximum plasma concentration ($C_{max}$) of the IL-17 binding molecule of about 360 μg/ml; and b) thereafter, is to be administered to the patient during a maintenance regimen that provides: i) an average steady-state trough level of the IL-17 binding molecule between about 8 μg/ml-about 30 μg/ml; and/or ii) a mean AUC tau at steady state of about 331 mg*day/L-about 1323 mg*day/L.

Disclosed herein are methods of treating a high risk RA patient, comprising: a) administering an IL-17 binding molecule to a patient in need thereof during an induction regimen that provides a mean maximum plasma concentration ($C_{max}$) of the IL-17 binding molecule of about 401 μg/ml; and b) thereafter administering the IL-17 binding molecule to the patient during a maintenance regimen that provides: i) an average steady-state trough level of the IL-17 binding molecule of about 9.4 μg/ml-about 31 μg/ml; and/or ii) a mean AUC tau at steady state of about 314 mg*day/L-about 1256 mg*day/L.

Disclosed herein are IL-17 binding molecule for use in treating psoriasis, characterized in that the IL-17 binding molecule: a) is to be administered to the patient during an induction regimen that provides a mean maximum plasma concentration ($C_{max}$) of the IL-17 binding molecule of about 401 μg/ml; and b) thereafter, is to be administered to the patient during a maintenance regimen that provides: i) an average steady-state trough level of the IL-17 binding molecule of about 9.4 μg/ml-about 31 μg/ml; and/or ii) a mean AUC tau at steady state of about 314 mg*day/L-about 1256 mg*day/L.

In some embodiments, the maintenance regimen provides an average steady-state trough level of the IL-17 binding molecule of about 9.4 μg/ml-about 17.3 μg/ml. In some embodiments, the maintenance provides an average steady-state trough level of the IL-17 binding molecule of about 9.4 μg/ml or about 17.3 μg/ml. In some embodiments, the induction regimen comprises intravenous administration of the IL-17 binding molecule every other week. In some embodiments, the maintenance regimen comprises monthly subcutaneous administration of the IL-17 binding molecule.

Disclosed herein are kits comprising: a) a pharmaceutical composition comprising an IL-17 antagonist for use in the treatment of rheumatoid arthritis (RA) in a patient; and b) instructions describing how to administer said pharmaceutical composition to the patient, wherein the patient is characterized as: i) being RF+, ACPA+, or both RF+ and ACPA+; and ii) having a high level of CRP, a high ESR, or both a high level of CRP and a high ESR.

Disclosed herein are IL-17 antagonists in preparation of a medicament for the treatment of RA, provided that the patient is selected for the treatment on the basis of: a) being RF+, ACPA+, or both RF+ and ACPA+; and b) having a high level of CRP, a high ESR, or both a high level of CRP and a high ESR.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated to comprise containers, each container having a sufficient amount of the IL-17 antagonist to allow delivery of at least about 75 mg-about 150 mg IL-17 antagonist per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated to comprise containers, each container having a sufficient amount of the IL-17 antagonist to allow delivery of at least about 10 mg/kg per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated at a dosage to allow intravenous delivery of about 10 mg/kg per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated at a dosage to allow subcutaneous delivery of about 75 mg-about 150 mg IL-17 antagonist per unit dose.

Disclosed herein are in vitro test methods for selecting a patient for treatment of RA, comprising determining if: i. the patient is RF+, ACPA+, or both RF+ and ACPA+; and ii. the patient has a high level of CRP, a high ESR, or both a high level of CRP and a high ESR. In some embodiments of the disclosed in vitro test methods, the patient has an improved therapeutic response to the following regimen: a) administering the patient three doses of about 10 mg/kg of an IL-17 antagonist, the first dose being delivered during week zero, the second dose being delivered during week two, and the third dose being delivered during week four; and a) thereafter administering the patient about 75 mg-about 150 mg of the IL-17 antagonist twice a month, monthly, every two months or every three months, beginning during week eight.

Disclosed herein are methods for producing a transmittable form of information on a patient having RA, comprising: a) assaying a sample from the patient for: i) rheumatoid factor (RF), anti-citrullinated protein antibody (ACPA), or RF and ACPA; and ii) C-reactive protein (CRP), an erythrocyte sedimentation rate (ESR), or both CRP and an ESR; and b) embodying the result of step a) in a transmittable form of information.

Herein are also provided methods of treating an inflammatory arthritis, comprising administering three induction doses (e.g., i.v., induction doses) of about 10 mg/kg or several (e.g., 1, 2, 3, 4, or 5) induction doses of about 150 mg (e.g., s.c. induction doses) of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to a patient having an inflammatory arthritis selected from the group consisting of rheumatoid arthritis (RA), spondyloarthropathy, ankylosing spondylitis (spondylarthritis), and psoriatic arthritis. In some embodiments, the induction doses are delivered every other week, and thereafter the patient is administered monthly maintenance doses (e.g., s.c. maintenance doses) of about 75 mg-about 300 mg (e.g., about 75 mg-about 150 mg, e.g., about 75 mg or about 150 mg) of the IL-17 antagonist (e.g., secukinumab), e.g., beginning one month from delivery of the final induction dose.

Herein are also provided methods of treating RA, comprising selecting a RA patient (e.g., a high risk RA patient) or a patient having elevated baseline CRP levels, administering the patient about 10 mg/kg (e.g., by an i.v. route) of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) every other week (e.g., during week 0, 2 and 4), and thereafter administering the patient about 75 mg-about 300 mg (e.g., about 75 mg-about 150 mg, e.g., about 75 mg or about 150 mg) (e.g., by an s.c. route) of the IL-17 antagonist on a monthly basis (e.g., beginning week 8).

In some embodiments of the disclosed methods, kits, uses, pharmaceutical compositions, and regimens, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR.

In some embodiments of the disclosed methods, kits, uses, pharmaceutical compositions, and regimens, the IL-17 antagonist is an IL-17 binding molecule or an IL-17 receptor binding molecule. In some embodiments, the IL-17 binding molecule or an IL-17 receptor binding molecule is an IL-17 binding molecule (e.g., IL-17 antibody) selected from the group consisting of: a) secukinumab; b) an IL-17 antibody that binds to an epitope of IL-17 comprising Leu74, Tyr85, His86, Met87, Asn88, Val124, Thr125, Pro126, Ile127, Val128, His129; c) an IL-17 antibody that binds to an epitope of IL-17 comprising Tyr43, Tyr44, Arg46, Ala79, Asp80; d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; e) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 pM, and wherein the IL-17 binding molecule has an in vivo half-life of about 4 weeks; and f) an IL-17 antibody that comprises an antibody selected from the group consisting of; i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; and viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

In preferred embodiments of the disclosed methods, kits, uses, pharmaceutical compositions, and regimens, the IL-17 binding molecule is a human antibody. In even more preferred embodiments of the disclosed methods, kits, uses, pharmaceutical compositions, and regimens, the IL-17 binding molecule is secukinumab.

BRIEF DESCRIPTION OF THE DRAWINGS

FIG. 12: Illustrates experimental and simulated pharmokinetic values for secukinumab.

DETAILED DESCRIPTION OF THE DISCLOSURE

Figure 1:
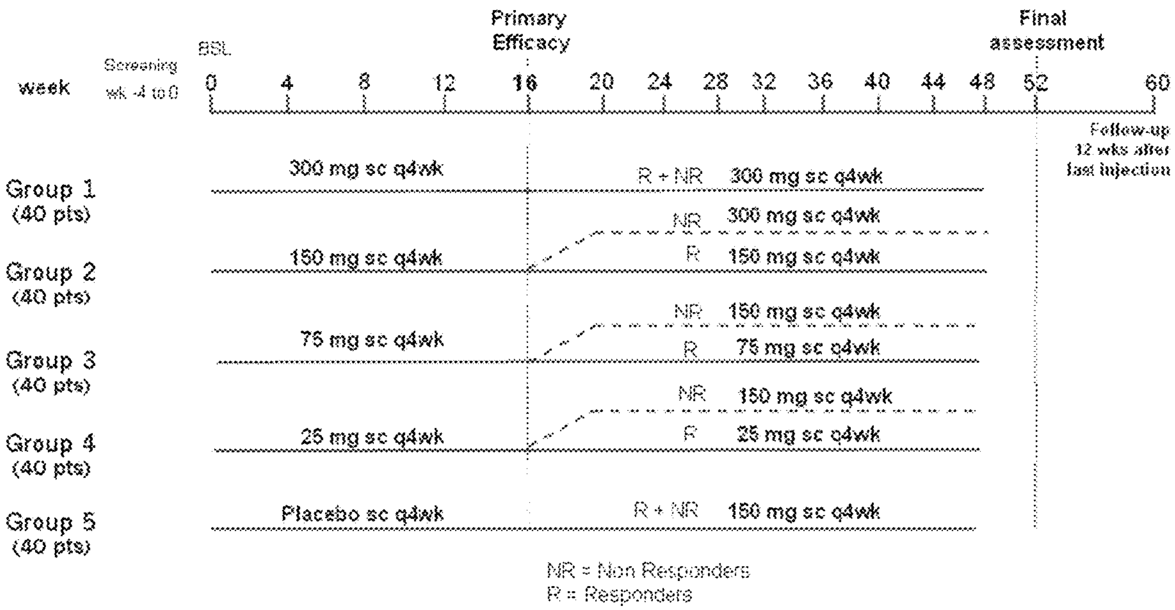
FIG. 1 shows the study design of the CAIN457F2201 study.

The 1987 American College of Rheumatology (ACR) classification criteria for RA discriminates patients with established RA from individuals with a combination of other definite rheumatological diagnoses. These criteria were not helpful in identifying patients with early RA disease who might benefit from early intervention. In 2010 ACR provided a new classification system that focuses on RA features at earlier stages of disease that are associated with persistent and/or erosive disease (hereinafter "2010 ACR/EULAR" criteria). Aletaha et al. (2010) Ann. Rheum. Dis. 69:1580-1588. The 2010 ACR/EULAR classification system focuses on six criteria; the first two criteria define who should be tested for RA, while the remaining four criteria are scored (Table 1). A score of six or greater is indicative of definite RA.

TABLE 1

The 2010 American College of Rheumatology/European League Against Rheumatism classification Criteria for Rheumatoid Arthritis (RA)

| | Score |
|---|---|
| Target population (Who should be tested?): Patients who | |
| 1) have at least 1 joint with definite clinical synovitis (swelling)* | |
| 2) with the synovitis not better explained by another disease† | |
| Classification criteria for RA (score-based algorithm: add score of categories A-D; a score of ≥6/10 is needed for classification of a patient as having definite RA)‡ | |
| A. Joint involvement§ | |
| 1 large joint¶ | 0 |
| 2-10 large joints | 1 |
| 1-3 small joints (with or without involvement of large joints)# | 2 |
| 4-10 small joints (with or without involvement of large joints) | 3 |
| >10 joints (at least 1 small joint)** | 5 |
| B. Serology (at least 1 test result is needed for classification)†† | |
| Negative RF and negative ACPA | 0 |
| Low-positive RF or low-positive ACPA | 2 |
| High-positive RF or high-positive ACPA | 3 |
| C. Acute-phase reactants (at least 1 test result is needed for classification)‡‡ | |
| Normal CRP and normal ESR | 0 |
| Abnormal CRP or abnormal ESR | 1 |
| D. Duration of symptoms§§ | |
| <6 weeks | 0 |
| ≥6 weeks | 1 |

*The criteria are aimed at classification of newly presenting patients. In addition, patients with erosive disease typical of rheumatoid arthritis (RA) with a history compatible with prior fulfillment of the 2010 criteria should be classified as having RA. Patients with longstanding disease, including those whose disease is inactive (with or without treatment) who, based on retrospectively available data, have previously fulfilled the 2010 criteria should be classified as having RA.

†Differential diagnoses vary among patients with different presentations, but may include conditions such as systemic lupus erythematosus, psoriatic arthritis, and gout. If it is unclear about the relevant differential diagnoses to consider, an expert rheumatologist should be consulted.

‡Although patients with a score of <6/10 are not classifiable as having RA, their status can be reassessed and the criteria might be fulfilled cumulatively over time.

§Joint involvement refers to any swollen or tender joint on examination, which may be confirmed by imaging evidence of synovitis. Distal interphalangeal joints, first carpometacarpal joints, and first metatarsophalangeal joints are excluded from assessment. Categories of joint distribution are classified according to the location and number of involved joints, with placement into the highest category possible based on the pattern of joint involvement.

¶"Large joints" refers to shoulders, elbows, hips, knees, and ankles.

#"Small joints" refers to the metacarpophalangeal joints, proximal interphalangeal joints, second through fifth metatarsophalangeal joints, thumb interphalangeal joints, and wrists.

**In this category, at least 1 of the involved joints must be a small joint; the other joints can include any combination of large and additional small joints, as well as other joints not specifically listed elsewhere (e.g., temporomandibular, acromioclavicular, sternoclavicular, etc.).

††Negative refers to IU values that are less than or equal to the upper limit of normal (ULN) for the laboratory and assay; low-positive refers to IU values that are higher than the ULN but </=3 times the ULN for the laboratory and assay; high-positive refers to IU values that are >3 times the ULN for the laboratory and assay. Where rheumatoid factor (RF) information is only available as positive or negative, a positive result should be scored as low-positive for RF. ACPA = anti-citrullinated protein antibody.

‡‡Normal/ab normal is determined by local laboratory standards. CRP = C-reactive protein; ESR =erythrocyte sedimentation rate.

§§Duration of symptoms refers to patient self-report of the duration of signs or symptoms of synovitis (e.g., pain, swelling, tenderness) of joints that are clinically involved at the time of assessment, regardless of treatment status.

In searching for indicators predictive of an RA patient's response to treatment with an IL-17 binding molecule, e.g., an IL-17 antibody, such as secukinumab, we have analyzed two of the four 2010 ACR/EULAR scoreable criteria to determine whether these criteria influence response to treatment with an IL-17 binding molecule, such as secukinumab. First, we analyzed patient serology to determine whether the patient is RF+ and/or ACPA+. Second, we analyzed the presence of acute-phase reactants to determine whether the patient has a high level of C-reactive protein (CRP) and/or a high erythrocyte sedimentation rate (ESR). In the process, we discovered that patients: 1) that are RF+ or ACPA+(or both); and 2) who have a high level of CRP or ESR (or both) are more likely to have a good response to treatment with an IL-17 binding molecule, e.g., an IL-17 antibody, such as secukinumab. Such patients (termed herein "high risk RA patients") are those with the most salient features of RA. (See, e.g., Yildirim et al. (2004) Annals Clin. Lab. Sci 34:423). Accordingly, disclosed herein are methods of treating rheumatoid arthritis (RA), comprising administering a therapeutically effective amount of an IL-17 binding molecule to a high risk RA patient.

We have additionally determined that elevated baseline CRP levels (e.g., >about 10 mg/L) are also associated with responsiveness to secukinumab. Accordingly, disclosed herein are methods of treating rheumatoid arthritis (RA), comprising administering a therapeutically effective amount of an IL-17 binding molecule to a RA patient displaying elevated baseline CRP levels (e.g., greater than about 10 mg/L, greater than about 20 mg/L, greater than about 30 mg/L).

We have further discovered that the treatment regimens useful in treating high risk RA patients are additionally useful in treating RA in non-high risk patients and patients having other inflammatory arthritis, e.g., ankylosing spondylitis (AS) or psoriatic arthritis (PsA). Accordingly, disclosed herein are dosing and treatment regimens for addressing inflammatory arthridities (e.g., RA, AS, PsA), comprising administering a therapeutically effective amount of an IL-17 binding molecule to a patient having an inflammatory arthridities.

The term "comprising" encompasses "including" as well as "consisting," e.g. a composition "comprising" X may consist exclusively of X or may include something additional, e.g., X+Y.

The term "about" in relation to a numerical value x means+/−10% unless the cotext dictates otherwise. The term "about," when used in reference to a pharmacokinetic (PK) parameter (e.g., AUC, $C_{max}$, $t_{max}$, trough levels, etc.), indicates a treatment (e.g., dosage and/or dosing regimen) that a skilled artisan would consider bioequivalent to a reference treatment. For bioequivalence, the standard method to show bioequivalence is to prove statistically that the ratio of a given PK parameter (e.g., AUC, $C_{max}$) between two treatments (i.e., a reference treatment and a test treatment) is between 0.8-1.25, which is shown by means of a 90% confidence interval (CI) around the ratio (the lower limit of this CI being above 0.8, and the upper limit of this CI being below 1.25). Thus, e.g., if during a trial comparing the PK profiles of a reference treatment and a test treatment, a reference $C_{max}$ of 10 μg/ml is obtained, then the test treatment will be considered "about 10 μg/ml" if a skilled artisan would consider the test treatment to be bioequivalent. As used herein, pharmacokinetic terms, e.g., $t_{max}$, $t_{1/2}$, AUC, $AUC_{(0\text{-}tau)}$ (AUC to the end of a given dosing period, hereinafter "AUC tau"), $C_{max}$, have their art-accepted meanings.

The term "administering" in relation to a compound, e.g., an IL-17 binding molecule or an anti-rheumatic agent, is used to refer to delivery of that compound by any route.

The phrase "active rheumatoid arthritis" or "active RA" is used to mean RA with visible signs and symptoms (e.g., swelling, difficulty in flexion, etc.).

The term "assaying" is used to refer to the act of detecting, identifying, screening, or determining, which act may be performed by any conventional means. For example, a sample may be assayed for the presence of a particular marker by using an ELISA assay, a Northern blot, imaging, etc. to detect whether that marker is present in the sample.

The word "substantially" does not exclude "completely," e.g., a composition which is "substantially free" from Y may be completely free from Y. Where necessary, the word "substantially" may be omitted from the definition of the disclosure.

As used herein, "mg/kg" refers to mg of drug per kg body weight of the patient being administered the drug.

"IL-17 antagonist" as used herein refers to a molecule capable of antagonizing (e.g., reducing, inhibiting, decreasing, blocking, delaying) IL-17 function, expression and/or signalling (e.g., by blocking the binding of IL-17 to the IL-17 receptor). Non-limiting examples of IL-17 antagonists include IL-17 binding molecules and IL-17 receptor binding molecules. In some embodiments of the disclosed methods, regimens, kits, processes, uses and compositions, an IL-17 antagonist is employed.

By "IL-17 binding molecule" is meant any molecule capable of binding to the human IL-17 antigen either alone or as it is associated with other molecules. The binding reaction may be shown by standard methods (qualitative assays) including, for example, a binding assay, competition assay or a bioassay for determining the inhibition of IL-17 binding to its receptor or any kind of binding assays, with reference to a negative control test in which an antibody of unrelated specificity but of the same isotype, e.g. an anti-CD25 antibody, is used. Non-limiting examples of IL-17 binding molecules include small molecules, IL-17 receptor decoys, and antibodies as produced by B-cells or hybridomas and chimeric, CDR-grafted or human antibodies or any fragment thereof, e.g., $F(ab')_2$ and Fab fragments, as well as single chain or single domain antibodies. Preferably the IL-17 binding molecule antagonizes (e.g., reduces, inhibits, decreases, delays) IL-17 function, expression and/or signalling. In some embodiments of the disclosed methods, regimens, kits, processes, uses and compositions, an IL-17 binding molecule is employed.

By "IL-17 receptor binding molecule" is meant any molecule capable of binding to the human IL-17 receptor either alone or associated with other molecules. The binding reaction may be shown by standard methods (qualitative assays) including, for example, a binding assay, competition assay or a bioassay for determining the inhibition of IL-17 receptor binding to IL-17 or any kind of binding assays, with reference to a negative control test in which an antibody of unrelated specificity but of the same isotype, e.g. an anti-CD25 antibody, is used. Non-limiting examples of IL-17 receptor binding molecules include small molecules, IL-17 decoys, and antibodies to the IL-17 receptor as produced by B-cells or hybridomas and chimeric, CDR-grafted or human antibodies or any fragment thereof, e.g., $F(ab')_2$ and Fab fragments, as well as single chain or single domain antibodies. Preferably the IL-17 receptor binding molecule antagonizes (e.g., reduces, inhibits, decreases, delays) IL-17 function, expression and/or signalling. In some embodiments of the disclosed methods, regimens, kits, processes, uses and compositions, an IL-17 receptor binding molecule is employed.

The term "antibody" as referred to herein includes whole antibodies and any antigen-binding portion or single chains thereof. A naturally occurring antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In some embodiments of the disclosed methods, regimens, kits, processes, uses and compositions, an antibody to IL-17 or the IL-17 receptor is employed.

The term "antigen-binding portion" of an antibody as used herein, refers to fragments of an antibody that retain the ability to specifically bind to an antigen (e.g., IL-17). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, CL and CH1 domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR). Exemplary antigen binding sites include the CDRs of secukinumab as set forth in SEQ ID NOs:1-6 and 11-13 (Table 4), preferably the heavy chain CDR3. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies are also intended to be encompassed within the term "antibody". Single chain antibodies and antigen-binding portions are obtained using conventional techniques known to those of skill in the art. In some embodiments of the disclosed methods, regimens, kits, processes, uses and compositions, a single chain antibody or an antigen-binding portion of an antibody against IL-17 (e.g., secukinumab) or the IL-17 receptor is employed.

The term "pharmaceutically acceptable" means a non-toxic material that does not interfere with the effectiveness of the biological activity of the active ingredient(s).

An "isolated antibody", as used herein, refers to an antibody that is substantially free of other antibodies having different antigenic specificities (e.g., an isolated antibody that specifically binds IL-17 is substantially free of antibodies that specifically bind antigens other than IL-17). An isolated antibody may be substantially free of other cellular material and/or chemicals. An isolated antibody that "specifically binds" IL-17 may, however, be cross-reactive with other antigens, such as IL-17 molecules from other species. In some embodiments of the disclosed methods, regimens, kits, processes, uses and compositions, the IL-17 antagonist is an isolated antibody.

The terms "monoclonal antibody" or "monoclonal antibody composition" as used herein refer to a preparation of antibody molecules of single molecular composition. A monoclonal antibody composition displays a single binding specificity and affinity for a particular epitope. In some embodiments of the disclosed methods, regimens, kits, processes, uses and compositions, the IL-17 antagonist is a monoclonal antibody.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. (2000. J Mol Biol 296, 57-86). A "human antibody" need not be produced by a human, human tissue or human cell. The human antibodies of the disclosure may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. In some embodiments of the disclosed methods, regimens, kits, processes, uses and compositions, the IL-17 antagonist is a human antibody.

The term "IL-17" refers to IL-17A, formerly known as CTLA8, and includes wild-type IL-17A from various species (e.g., human, mouse, and monkey), polymorphic variants of IL-17A, and functional equivalents of IL-17A. Functional equivalents of IL-17A according to the present disclosure preferably have at least about 65%, 75%, 85%, 95%, 96%, 97%, 98%, or even 99% overall sequence identity with a wild-type IL-17A (e.g., human IL-17A), and substantially retain the ability to induce IL-6 production by human dermal fibroblasts.

The term "$K_D$" is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system. In some embodiments of the invention the IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) binds human IL-17 with a $K_D$ of about 100-250 pM.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity. Standard assays to evaluate the binding affinity of the antibodies toward IL-17 of various species are known in the art, including for example, ELISAs, western blots and RIAs. The binding kinetics (e.g., binding affinity) of the antibodies also can be assessed by standard assays known in the art, such as by Biacore analysis. Assays to evaluate the effects of the antibodies on functional properties of IL-17 (e.g., receptor binding, preventing or ameliorating osteolysis) are described in further detail in the Examples.

As used herein, the term "subject" and "patient" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc.

An antibody that "inhibits" one or more of IL-17 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (or when a control antibody of irrelevant specificity is present). An antibody that inhibits IL-17 activity affects a statistically significant decrease, e.g., by at least 10% of the measured parameter, by at least 50%, 80% or 90%, and in certain embodiments an antibody of the disclosure may inhibit greater than 95%, 98% or 99% of IL-17 functional activity.

The term "derivative", unless otherwise indicated, is used to define amino acid sequence variants, and covalent modifications of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) according to the present disclosure, e.g., of a specified sequence. A "functional derivative" includes a molecule having a qualitative biological activity in common with the disclosed IL-17 antagonista, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof). A functional derivative includes fragments and peptide analogs of an IL-17 antagonist as disclosed herein. Fragments comprise regions within the sequence of a polypeptide according to the present disclosure, e.g., of a specified sequence. Functional derivatives of the IL-17 antagonists disclosed herein preferably comprise $V_H$ and/or $V_L$ domains that have at least about 65%, 75%, 85%, 95%, 96%, 97%, 98%, or even 99% overall sequence identity with the $V_H$ and/or $V_L$ sequences of the IL-17 binding molecules disclosed herein (e.g., the $V_H$ and/or $V_L$ sequences of Table 4), or comprise CDRs that have at least about 65%, 75%, 85%, 95%, 96%, 97%, 98%, or even 99% overall sequence identity with the CDRs of the IL-17 antagonists (e.g., secukinumab) disclosed herein (e.g., have 1, 2, or 3 amino acid differences from the CDRs set forth in Table 4), and substantially retain the ability to bind the human IL-17 or, e.g., inhibit IL-6 production of IL-17 induced human dermal fibroblasts.

"Inhibit IL-16" as used herein refers to the ability of an IL-17 antagonist (e.g., secukinumab) to decrease IL-6 production from primary human dermal fibroblasts. The production of IL-6 in primary human (dermal) fibroblast is dependent on IL-17 (Hwang S Y et al., (2004) Arthritis Res Ther; 6:R120-128. In short, human dermal fibroblasts are stimulated with recombinant IL-17 in the presence of various concentrations of an IL-17 binding molecule or human IL-17 receptor with Fc part. The chimeric anti-CD25 antibody Simulect® (basiliximab) may be conveniently used as a negative control. Supernatant is taken after 16 h stimulation and assayed for IL-6 by ELISA. An IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) as disclosed herein typically has an $IC_{50}$ for inhibition of IL-6 production (in the presence 1 nM human IL-17) of about 50 nM or less (e.g., from about 0.01 to about 50 nM) when tested as above, i.e., said inhibitory activity being measured on IL-6 production induced by hu-IL-17 in human dermal fibroblasts. In some embodiments of the disclosed methods, regimens, kits, processes, uses and compositions, IL-17 antagonists, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof) and functional derivatives thereof have an $IC_{50}$ for inhibition of IL-6 production as defined above of about 20 nM or less, more preferably of about 10 nM or less, more preferably of about 5 nM or less, more preferably of about 2 nM or less, more preferably of about 1 nM or less.

The term "covalent modification" includes modifications of a polypeptide according to the present disclosure, e.g., of a specified sequence; or a fragment thereof with an organic proteinaceous or non-proteinaceous derivatizing agent, fusions to heterologous polypeptide sequences, and post-translational modifications. Covalent modified polypeptides, e.g., of a specified sequence, still have the ability to bind the human IL-17 or, e.g., inhibit IL-6 production of IL-17 induced human dermal fibroblasts by crosslinking. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deaminated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains, see, e.g., T. E. Creighton, Proteins: Structure and Molecular Properties, W. H. Freeman & Co., San Francisco, pp. 79-86 (1983). Covalent modifications, e.g., include fusion proteins comprising a polypeptide according to the present disclosure, e.g., of a specified sequence and their amino acid sequence variants, such as immunoadhesins, and N-terminal fusions to heterologous signal sequences.

The phrase "substantially identical" means that the relevant amino acid or nucleotide sequence (e.g., CDR(s), $V_H$, or $V_L$ domain) will be identical to or have insubstantial differences (e.g., through conserved amino acid substitutions) in comparison to a particular reference sequence. Insubstantial differences include minor amino acid changes, such as 1 or 2 substitutions in a 5 amino acid sequence of a specified region. In the case of antibodies, the substituted antibody has the same specificity and has at least 50% of the affinity of the same. Sequences substantially identical (e.g., at least about 85% sequence identity) to the sequences disclosed herein are also part of this application. In some embodiments, the sequence identity can be about 90% or greater, e.g., 90%, 91%, 92%, 93%, 94%, 95%, 96%, 97%, 98%, 99% or higher.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring L-α-amino acids, e.g., and include D-amino acids. The amino acids are identified by either the well known single-letter or three-letter designations.

The term "amino acid sequence variant" refers to molecules with some differences in their amino acid sequences as compared to the sequences according to the present disclosure. Amino acid sequence variants of a polypeptide according to the present disclosure, e.g., of a specified sequence, still have the ability to bind the human IL-17 or, e.g., inhibit IL-6 production of IL-17 induced human dermal fibroblasts. Substitutional variants are those that have at least one amino acid residue removed and a different amino acid inserted in its place at the same position in a polypeptide according to the present disclosure, e.g., of a specified sequence. These substitutions may be single, where only one amino acid in the molecule has been substituted, or they may be multiple, where two or more amino acids have been substituted in the same molecule. Insertional variants are those with one or more amino acids inserted immediately adjacent to an amino acid at a particular position in a polypeptide according to the present disclosure, e.g., of a specified sequence. Immediately adjacent to an amino acid means connected to either the α-carboxy or α-amino functional group of the amino acid. Deletional variants are those with one or more amino acids in a polypeptide according to the present disclosure, e.g., of a specified sequence, removed. Ordinarily, deletional variants will have one or two amino acids deleted in a particular region of the molecule.

As used herein, a "therapeutically effective amount" refers to an amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) that is effective, upon single or multiple dose administration to a subject (such as a human patient) at treating, preventing, preventing the onset of, curing, delaying, reducing the severity of, ameliorating at least one symptom of a disorder or recurring disorder, or prolonging the survival of the subject beyond that expected in the absence of such treatment. When applied to an individual active ingredient (e.g., an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof)) administered alone, the term refers to that ingredient alone. When applied to a combination, the term refers to combined amounts of the active ingredients that result in the therapeutic effect, whether administered in combination, serially or simultaneously.

The terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment.

As used herein, the phrase "inflammatory arthritis" refers to a variety of conditions of the joints that involve the immune system and inflammation, and includes autoimmune disorders, e.g., rhuematoid arthritis. Non-limiting examples include seronegative spondyloarthropathies such as AS, Reiter's syndrome, PsA, enteropathic arthritis, and other arthropathies such as RA, juvenile rheumatoid arthritis and systemic onset rheumatoid arthritis, crystaline arthritis (gout pseudogout, apatite gout), polymyalgia rheumatica, amyloid arthritis, pigment villonodular synovitis, synovial chondromatosis, hemophilic arthritis, and reactive synovitis. In some embodiments of the disclosed methods, regimens, uses, kits, and pharmaceutical compositions, the patient has an inflammatory arthridities.

As used herein, the phrases "ankylosing spondylitis", "AS', and "spodyloarthropathy" refer to inflammatory arthridities characterized by chronic inflammation of joints, which can include the spine and the sacroilium in the pelvis, and which can cause eventual fusion of the spine. The modified New York criteria for AS or the ASAS axial SPA criteria (2009) may be used to diagnose a patient as having AS. In some embodiments of the disclosed methods, regimens, uses, kits, and pharmaceutical compositions, the patient has AS.

As used herein, the phrase "psoriatic arthritis" and "PsA" refer to an inflammatory arthridities that is often associated with psoriasis of the skin. A variety of criteria, e.g. Moll and Wright criteria, Modified ESSG criteria, McGonagle criteria, the Classification Criteria for Psoriatic Arthritis (CASPAR) criteria, etc. may be used to diagnose a patient as having PsA. In some embodiments of the disclosed methods, regimens, uses, kits, and pharmaceutical compositions, the patient has PsA.

As used herein, "rheumatoid arthritis" or "RA" refers to a chronic, systemic inflammatory arthridities that may affect many tissues and organs, but principally attacks synovial joints. The 2010 ACR/EULAR criteria may be used to diagnose a patient as having RA. In some embodiments of the disclosed methods, regimens, uses, kits, and pharmaceutical compositions, the patient has RA.

As used herein, the phrase "2010 ACR/EULAR criteria" refers to the 2010 American College of Rheumatology/European League Against Rheumatism classification criteria for RA found in Aletaha et al. (2010) Ann. Rheum. Dis. 69:1580-1588. That criteria, which is used to classify a patient as having rheumatoid arthritis, is set forth in Table 1.

As used herein, "C-reactive protein" and "CRP" refers to serum C-reactive protein, a plasma protein commonly used as an indicator of the acute phase response to inflammation. The level of CRP in plasma may be given in any concentration, e.g., mg/dl, nmol/L. Levels of CRP may be measured by a variety of well known methods, e.g., radial immunodiffusion, electroimmunoassay, immunoturbidimetry, ELISA, turbidimetric methods, fluorescence polarization immunoassay, and laser nephelometry. Testing for CRP may employ a standard CRP test or a high sensitivity CRP (hs-CRP) test (i.e., a high sensitivity test that is capable of measuring low levels of CRP in a sample using laser nephelometry). Kits for detecting levels of CRP may be purchased from various companies, e.g., Calbiotech, Inc, Cayman Chemical, Roche Diagnostics Corporation, Abazyme, DADE Behring, Abnova Corporation, Aniara Corporation, Bio-Quant Inc., Siemens Healthcare Diagnostics, etc.

As used herein "high level of CRP" refers to an above normal CRP level as defined in the 2010 ACR/EULAR criteria (Aletaha et al. (2010) Ann. Rheum. Dis. 69:1580-88). According to the 2010 ACR/EULAR criteria, normal/abnormal CRP is based on local laboratory standards. Each local laboratory will employ a cutoff value for abnormal (high) CRP based on that laboratory's rule for calculating normal maximum CRP. A physician generally orders a CRP test from a local laboratory, and the local laboratory reports normal or abnormal (low or high) CRP using the rule that particular laboratory employs to calculate normal CRP. Thus, unless the context dictates otherwise, as used herein "high level of CRP" is not meant to denote a particular numerical value, as what is considered a normal CRP value will differ between laboratories and assays. In some embodiments of the disclosure, a "high level of CRP" is >about 10 mg/L (e.g., 10 mg/L), >about 20 mg/L (e.g., 20 mg/L) or >about 30 mg/L (e.g., 30 mg/L). The CRP level, when assessed at baseline, is referred to as "baseline CRP". A high level of CRP at baseline may be referred to as "elevated baseline CRP" or "high baseline CRP". In some embodiments of the disclosed methods, regimens, uses, kits, and pharmaceutical compositions, the patient has a high baseline CRP (or hsCRP) or a high level of CRP (or hsCRP). The term "hsCRP" refers to the level of CRP in the blood as measured by high sensitivity CRP testing.

As used herein, "erythrocyte sedimentation rate", "ESR", "sedimentation rate", and "sedrate" refer to the rate of sedimentation of erythrocytes in a patient sample (e.g., plasma sample). An ESR reflects plasma viscosity and the presence of acute phase proteins, and is normally reported in "mm/hr". ESR is performed by measuring the distance that red blood cells precipitate in a tube over time. Typical ESR testing methods utilize the Westergren test, the Zeta Sedimentation Rate (ZSR) test and the Wintrobe test. (See, Moseley and Bull (1982) Clin. Lab Haematol. 4:169-78; Miller et al. (1983) Br Med J (Clin Res Ed) 286 (6361):266, Wetteland Pet al. (1996) J. Intern. Med. 240 (3): 125-310, all of which are incorporated by reference herein in their entirety). Commercial kits for measuring ESR are available from, e.g., ARKRAY USA, BD Diagnostic Systems, and Polymedco Inc. ESR instruments may be found, e.g., in U.S. Pat. No. 6,974,701, and from various companies, such as Steellex Scientific, Nicesound Electronics Co., Globe Scientific Inc., Alifax, AnalysisInstrument AB, Streck Laboratories, PolyMed Co, Inc., and Quantimetrix.

As used herein "high ESR" refers to an above normal ESR as defined in the 2010 ACR/EULAR criteria (Aletaha et al. (2010) Ann. Rheum. Dis. 69:1580-88). According to the 2010 ACR/EULAR criteria, normal/abnormal ESR is based on local laboratory standards. Each local laboratory will employ a cutoff value for abnormal (high) ESR based on that laboratory's rule for calculating normal maximum ESR. A physician generally orders an ESR test from a local laboratory, and the local laboratory will report normal or high ESR using the rule that laboratory employs to calculate normal ESR. Thus, unless the context dictates otherwise, as used herein "high ESR" is not meant to denote a particular numerical value, as what is considered a normal ESR value will differ between laboratories and assays. In some embodiments of the disclosed methods, regimens, uses, kits, and pharmaceutical compositions, the patient has a high ESR.

As used herein, "rheumatoid factor" or "RF" refers to autoantibodies against the Fc portion of IgG antibodies, which are often present in RA patients. As used herein "RF" includes any RF isotype, e.g., IgG, IgE, IgM and IgA. RF can be assayed using a variety of well-known techniques that are available to determine the presence or absence of a particular antibody, e.g., an ELISA assay, an agglutination test, a nephelometry test, etc. RF levels may be reported by laboratories in a variety of ways, e.g., IU/ml, units/ml, and titer (using a dilution test to measure how much a blood sample from a patient may be diluted before RF can no longer be detected, e.g., a titer of 1:80 indicates more detectable RF than a titer of 1:20). RF kits are commercially available, e.g., from IBL—America (Immuno-Biological Laboratories).

A patient that is seropositive for RF is referred to herein as "RF+". Similarly, if a sample from a patient has RF, then that sample is "RF+". Each local laboratory will employ a cutoff value for normal RF levels based on that laboratory's rule for calculating normal maximum RF. As suggested by Aletaha et al. (2010) Ann. Rheum. Dis. 69:1580-1588, a patient will be considered RF+ based on the upper limit of normal [ULN] for the respective laboratory test and assay; a patient is RF+ if a value greater than the ULN for the respective laboratory test and assay is determined. Accordingly, unless the context dictates otherwise, as used herein "RF+" is not meant to denote a particular numerical value, as the ULN will differ between laboratories and assays. As a non-limiting example, at the time of testing, Laboratory X gives the normal range of RF in the blood as 14-60 units/mL. At the time of testing, Laboratory Y gives the normal range of RF in the blood as ≤40 IU/ml. At the time of testing, Laboratory Z gives the normal range of RF in the blood as 1:20 to 1:80 titer. Thus, a patient would be RF+ if Laboratory X returned an RF level of greater than 60 units/ml, if Laboratory Y returned an RF value of greater than 40 IU/ml, or if Laboratory Z returned an RF titer greater than 1:80. In some embodiments of the disclosed methods, regimens, uses, kits, and pharmaceutical compositions, the patient is RF+.

The term "seropositive" used to mean the presence of a specific substance (e.g., RF) in a patient's blood serum.

As used herein, "anti-citrullinated protein antibody", "ACPA", "anti-cyclic citrullinated peptide antibody" and "anti-CCP" refers to autoantibodies that bind citrullinated amino acid residues on proteins, which are found in the joints of in RA patients. Cyclic citrullinated peptides are used in in vitro tests (e.g., ELISA assays) to determine the presence of ACPA in a patient's blood; as a result, an ACPA is also referred to as an "anti-CCP" antibody. ACPA levels can be assayed using a variety of well-known techniques that are available to determine the presence or absence of a particular antibody, e.g., agglutination, ELISA assay, etc. ACPA kits are commercially available, e.g., the DIASTAT® anti-CCP test from Axis-Shield Diagnostics, Ltd. (UK) and AxSYM Anti-CCP® kit from Abbot Diagnostics (Germany).

A patient that is seropositive for ACPA is referred to herein as "ACPA+". Similarly, if a sample from a patient has ACPA, then that sample is "ACPA+". Each local laboratory will employ a cutoff value for normal ACPA levels based on that laboratory's rule for calculating normal maximum ACPA. As suggested by Aletaha et al. (2010) Ann. Rheum. Dis. 69:1580-1588, a patient will be considered ACPA+ based on the upper limit of normal [ULN] for the respective laboratory test and assay; a patient is ACPA+ if a value greater than the ULN for the respective laboratory test and assay is determined. Accordingly, unless the context dictates otherwise, as used herein "ACPA+" is not meant to denote a particular numerical value, as the ULN will differ between laboratories and assays. As a non-limiting, at the time of testing, Laboratory A gives the reference range of ACPA in the blood as <20 EU (arbitrary ELISA units). At the time of testing, Laboratory B gives the reference range of ACPA in the blood as <5 U/ml. Thus, a patient would be ACPA+ if Laboratory A returned an ACPA value greater than 20 EU or if Laboratory B returned an ACPA value of greater than 5

U/ml. In some embodiments of the disclosed methods, regimens, uses, kits, and pharmaceutical compositions, the patient is ACPA+.

Select normal/abnormal and reference ranges for ACPA, ESR, RF and CRP may be found, e.g., in Fischbach and Dunning (2009) "A Manual of Laboratory and Diagnostic Tests" ($8^{th}$ Edition) Wolters Kluwer/Lippincott Williams and Williams, which is incorporated by reference herein in its entirety.

As used herein, the phrase "high risk RA patient" is used to define a patient that: a) is RF+, ACPA+ or both RF+ and ACPA+; and b) has a high level of CRP (or hsCRP), a high ESR, or both a high level of CRP and a high ESR. In some embodiments of the disclosed methods, regimens, uses, kits, and pharmaceutical compositions, the patient is a high risk RA patient. In some embodiments, the patient presents with involvement of at least one, two, three four, five, six, seven, eight, nine or ten small joints. In some embodiments, the patient presents with involvement of at least one, two, three four, five, six, seven, eight, nine or ten large joints. In some embodiments, the patient presents with involvement of greater than ten joints, with at least one of the joints being a small joint. In some embodiments, the patient has duration of symptoms of at least six weeks.

"Joint involvement" refers to any swollen or tender joint on examination, which may be confirmed by imaging evidence of synovitis. Categories of joint distribution are classified according to the location and number of involved joints, with placement into the highest category possible based on the pattern of joint involvement. "Large joints" refers to shoulders, elbows, hips, knees, and ankles. "Small joints" refers to the metacarpophalangeal joints, proximal interphalangeal joints, second through fifth metatarsophalangeal joints, thumb interphalangeal joints, and wrists. In some embodiments of the disclosed methods, regimens, uses, kits and compositions, a patient has ≥6 out of 28 tender joints and ≥6 out of 28 swollen joints and hsCRP>10 mg/L.

"Duration of symptoms" refers to patient self-report of the duration of signs or symptoms of synovitis (e.g., pain, swelling, tenderness) of joints that are clinically involved at the time of assessment, regardless of treatment status.

As used herein, "selecting a high risk RA patient for treatment" and "selecting a patient for treatment on the basis of the patient being a high risk RA patient" and "selected for treatment" is used to mean that a particular RA patient is chosen from a larger group or RA patients based on that particular patient fulfilling the high risk RA criteria (i.e., the patient is RF+, ACPA+, or both RF+ and ACPA+; and the patient has a high level of CRP, a high ESR, or both a high level of CRP and a high ESR).

As used herein, the phrase "has been previously treated for RA" is used to mean a patient that has previously undergone RA treatment using an anti-rheumatic agent, e.g., the patient is a failure, an inadequate responder, or intolerant to a previous RA therapy, anti-rheumatic agent or treatment regimen. Such patients include those previously treated with MTX, DMARDs, and/or biologics, such as TNF alpha antagonists, etc. In some embodiments of the disclosed methods, regimens, uses, kits, and pharmaceutical compositions, the patient has been previously treated for RA.

As used herein, the phrase "has not been previously treated for RA" is used to mean a patient that has not previously undergone RA treatment using an anti-rheumatic agent, i.e., the patient is "naïve". In some embodiments of the disclosed methods, regimens, uses, kits, and pharmaceutical compositions, the patient has not been previously treated for RA.

As used herein, a "failure" to a previous RA therapy refers to: (1) a patient who has no meaningful clinical benefit (primary lack of efficacy); (2) a patient who has a measurable and meaningful response, but for whom response could be better, e.g., low RA disease activity or RA remission was not achieved (also termed "inadequate response"); (3) a patient who, after an initial good response, worsens (secondary loss of efficacy); and (4) a patient who has a good response but discontinues because of a side effect (also termed "intolerance"). Patients who show TNF inadequate response (TNF-IR) or intolerance to TNF would be considered TNF failures. Patients who show methotrexate inadequate response (MTX-IR) or intolerance to MTX would be considered MTX failures. Patients who show DMARD inadequate response (DMARD-IR) or intolerance to DMARDs would be considered DMARD failures. In some embodiments of the disclosed methods, regimens, uses, kits, and pharmaceutical compositions, the patient is a TNF failure, a MTX failure, or a DMARD failure.

By "therapeutic regimen" is meant the pattern of treatment of an illness, e.g., the pattern of dosing used during the treatment of RA. A therapeutic regimen may include an induction regimen and a maintenance regimen. Examples of therapeutic regimens for treatment of RA are given in Table 2, none of which provide for treatment of a high risk RA patient.

TABLE 2

Examples of therapeutic regimens for biological treatment of rheumatoid arthritis (RA)

| Standard | Route | Induction Regimen | Maintenance Regimen |
|---|---|---|---|
| ADALIMUMAB Humira ® | s.c. | NA | 40 mg every other week. Some patients with RA not receiving methotrexate may benefit from increasing the frequency to 40 mg every week. |
| ETANERCEPT Enbrel ® | s.c. | NA | 50 mg once weekly with or without methotrexate (MTX). |
| INFLIXIMAB Remicade ® | i.v. | 3 mg/kg at 0, 2, and 6 weeks | 3 mg/kg every 8 weeks thereafter. For patients who have an incomplete response, consideration may be given to adjusting the dose up to 10 mg/kg or treating as often as every 4 weeks. |
| CERTOLIZUMAB PEGOL Cimzia ® | s.c. | 400 mg (given as two s.c. doses of 200 mg) initially and at weeks 2 and 4. | 200 mg every other week; for maintenance dosing, 400 mg every 4 weeks can be considered. |
| GOLIMUMAB Simponi ® | s.c. | NA | 50 mg administered once a month. |

TABLE 2-continued

| Examples of therapeutic regimens for biological treatment of rheumatoid arthritis (RA) | | | |
|---|---|---|---|
| Standard | Route | Induction Regimen | Maintenance Regimen |
| ANAKINRA Kineret ® | s.c. | NA | 100 mg/day administered daily. |
| RITUXIMAB Rituxan ® | i.v. | two 1000 mg IV infusions separated by 2 weeks (one course). | Subsequent courses should be administered every 24 weeks or based on clinical evaluation, but not sooner than every 16 weeks. |
| ABATACEPT Orencia ® | i.v. | <60 kg = 500 mg; 60 to 100 kg = 750 mg; >100 kg = 1000 mg initially, then 2 and 4 weeks after initial infuion | Every 4 weeks thereafter. |
| TOCILIZUMAB Actemra ® | i.v. | NA | 4 mg/kg once every 4 weeks followed by an increase to 8 mg/kg based on clinical response. |

The phrase "induction regimen" or "induction period" refers to a treatment regimen (or the portion of a treatment regimen) that is used for the initial treatment of a disease. In some embodiments, the disclosed methods, uses, kits, processes and regimens (e.g., methods of treating an inflammatory arthridities, e.g., RA, such as a high risk RA patient) employ an induction regimen. The general goal of an induction regimen is to provide a high level of drug to a patient during the initial period of a treatment regimen. An induction regimen may employ (in part or in whole) administration of a greater dose of the drug than a physician would employ during a maintenance regimen, administering a drug more frequently than a physician would administer the drug during a maintenance regimen, or both. In some embodiments of the disclosed methods, uses, kits, processes and regimens the induction dose may be delivered during an induction regimen as a single high dose infusion (e.g., about 30 mg/kg). Alternatively, an induction dose may be delivered as several (e.g., two or three) infusions (e.g., about 10 mg/kg). Alternatively, an induction dose may be delivered as several (e.g., 1, 2, 3, 4, 5, 6 or more) subcutaneous injections (e.g., about 75-300 mg). Delivery of drug during an induction regimen may be via a subcutaneous (s.c.) route, e.g., delivery of dosages of about 75 mg-about 300 mg s.c. (e.g., about 75 mg s.c., about 150 mg s.c., about 300 mg s.c.), or via an intravenous (i.v.) route, e.g., delivery of dosages of about 1 mg/kg-about 30 mg/kg i.v. (e.g., about 1 mg/kg, about 3 mg/kg, about 10 mg/kg, about 30 mg/kg) or any other route of administration (e.g, intramuscular, i.m.). In some embodiments of the disclosed methods, compositions, kits, uses and regimens the IL-17 antagonist (e.g., secukinumab) is delivered by i.v. administration during at least a portion of the induction regimen. In some embodiments, the induction regimen comprises administering a dose of about 1 mg/kg-about 30 mg/kg, about 1 mg/kg-about 10 mg/kg, preferably about 10 mg/kg of the IL-17 antagonist (e.g., secukinumab). In further embodiments, the induction doses are delivered weekly, bi-weekly, every other week, or monthly, preferably every other week. In further embodiments, the induction regimen employs 1-10 doses of the IL-17 antagonist (e.g., secukinumab), preferably three doses of the IL-17 antagonist (e.g., secukinumab).

An induction regimen for delivery of an IL-17 antagonist, e.g., an IL-17 binding molecule (e.g., an IL-17 antibody, such as secukinumab) or an IL-17 receptor binding molecule (e.g., an IL-17 receptor antibody) may also be designed using PK information (see Table 10), rather than specific dosages. For the disclosed uses, regimens and methods (e.g., methods of treating an inflammatory arthridities, e.g., RA, such as a high risk RA patient), an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide an average $C_{max}$ of about 360 μg/mL-about 401 μg/mL. Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide an average $C_{max}$ of about 401 μg/mL, with up to about a 30%-40% [+ or −] inter-patient variation for an average 90 kg human. Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide an average $C_{max}$ of about 360 μg/mL for an average 75 kg human. Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during an induction regimen to provide trough levels over 80 μg/mL over a 10 week period for an average 75 kg human. In some embodiments, the IL-17 antagonist is delivered week 0, 2 and 4 i.v. during an induction regimen to provide an average average $C_{max}$ of about 401 μg/mL, with up to about a 30%-40% [+ or −] inter-patient variation for an average 90 kg human. In some embodiments, the IL-17 antagonist is delivered week 0, 2 and 4 i.v. during an induction regimen to provide an average $C_{max}$ of about 360 μg/mL for an average 75 kg human. In other embodiments, the IL-17 antagonist is delivered week 0, 2 and 4 i.v. during an induction regimen to provide trough levels over 80 μg/mL over a 10 week period for an average 75 kg human.

The phrase "maintenance regimen" or "maintenance period" refers to a treatment regimen (or the portion of a treatment regimen) that is used for the maintenance of a patient during treatment of an illness, e.g., to keep the patient in remission for long periods of time (months or years). In some embodiments, the disclosed methods, uses and regimens (e.g., methods of treating an inflammatory arthridities, e.g., RA, such as a high risk RA patient) employ a maintenance regimen. A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]). Delivery of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) during a maintenance regimen may be via a subcutaneous route, e.g., delivery of dosages of about 75 mg-about 300 mg s.c. (e.g., about 75 mg s.c., about 150 mg s.c., about 300 mg s.c.), or via an intravenous route, e.g., delivery of dosages of about 1 mg/kg-about 30 mg/kg i.v. (e.g., about 1 mg/kg, about 3 mg/kg, about 10 mg/kg, about 30 mg/kg), or any other route of administration (e.g, intramuscular, i.m.). In some embodiments of the disclosed methods, uses and regimens, the IL-17 antagonist (e.g., secukinumab) is delivered by s.c. administration during the maintenance regimen. In some embodiments, the maintenance regimen comprises administering a dose of about 75 mg-about 300 mg, about 75 mg-about 150 mg, preferably about 75 mg or about 150 mg of the IL-17 antagonist (e.g., secukinumab). In some embodiments, the maintenance regimen comprises administering a dose of the IL-17 antagonist (e.g., secukinumab) on a monthly basis.

A maintenance regimen for delivery of an IL-17 antagonist, e.g., an IL-17 binding molecule (e.g., an IL-17 antibody, such as secukinumab) or an IL-17 receptor binding molecule (e.g., an IL-17 receptor antibody) may also be designed using PK information (see Table 9), rather than specific dosages. For the disclosed uses, regimens and methods (e.g., methods of treating an inflammatory arthridities, e.g., RA, such as a high risk RA patient), an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during a maintenance regimen to provide an average steady-state trough level of about 9.4 μg/mL-about 31 μg/mL (e.g., about 9.4 μg/mL, about 17.3 μg/mL, about 31 μg/mL), with up to about a 30% [+ or −] inter-patient variation for an average 75 kg (e.g., 71-79 kg) human. Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during a maintenance regimen to provide an average steady-state trough level of about 8.0 μg/mL-about 30.0 μg/mL (e.g., about 8.0 μg/mL, about 17 μg/mL, about 30 μg/mL) for an average 75 kg human. In some embodiments, the IL-17 antagonist is delivered monthly during a maintenance regimen to provide an average steady-state trough level of about 9.4 μg/mL-about 31 μg/mL (e.g., about 9.4 μg/mL, about 17.3 μg/mL, about 31 μg/mL), with up to about a 30% [+ or −] inter-patient variation for an average 70 kg human. In other embodiments, the IL-17 antagonist is delivered monthly during a maintenance regimen to provide an average steady-state trough level of about 8.0 μg/mL-about 30.0 μg/mL (e.g., about 8.0 μg/mL, about 17 μg/mL, about 30 μg/mL) for an average 75 kg human. Alternatively, an artisan may deliver an IL-17 antagonist, e.g., an IL-17 binding molecule (e.g., an IL-17 antibody, such as secukinumab) or an IL-17 receptor binding molecule (e.g., an IL-17 receptor antibody) during a maintenance regimen to provide a mean AUC tau at steady state of about 314 mg*day/L-about 1323 mg*day/L (e.g., about 314 mg*day/L to about 1256 mg*day/L, e.g., about 331 mg*day/L to about 1323 mg*day/L).

The timing of dosing is generally measured from the day of the first dose of secukinumab (which is also known as "baseline"). However, different health care providers use different naming conventions, as shown in Table 3, below.

TABLE 3

Common naming conventions for dosing regimens. Bolded items refer to the naming convention used herein.

| Week | 0/1 | 1/2 | 2/3 | 3/4 | 4/5 | 5/6 | 6/7 | 7/8 | 8/9 | 9/10 | 10/11 | etc |
|---|---|---|---|---|---|---|---|---|---|---|---|---|
| 1$^{st}$ day | 0/1 | 7/8 | 14/15 | 21/22 | 28/29 | 35/36 | 42/43 | 49/50 | 56/57 | 63/64 | 70/71 | etc. |

Notably, week zero may be referred to as week one in some naming conventions, while day zero may be referred to as day one in some naming conventions. Thus, it is possible that different physicians will designate, e.g., a dose as being given during week 3/on day 21, during week 3/on day 22, during week 4/on day 21, during week 4/on day 22, while referring to the same dosing schedule. For consistency, as used herein, the first week of dosing will be referred to as week zero, while the first day of dosing will be referred to as day 1. Thus, as an example, four induction doses of secukinumab administered weekly during an induction regimen would be provided during week 0 (e.g., on about day 1), during week 1 (e.g., on about day 8), during week 2 (e.g., on about day 15), and during week 3 (e.g., on about day 22). Induction doses may be administered every two weeks (i.e., every other week), e.g., during week 0, during week 2, during week 4, etc. Induction doses may be administered every three weeks, e.g., during week 0, during week 3, during week 6, etc. Induction doses may be administered daily for one week, e.g., on day 1-7. It must be noted, however, that this naming convention is only used for clarity, and should not be construed as limiting.

As used herein, the phrase "means for administering" is used to indicate any available implement for systemically administering a biologic, including, but not limited to, a pre-filled syringe, a vial and syringe, an injection pen, an autoinjector, an i.v. drip and bag, a pump, etc. With such items, a patient may self-administer the drug (i.e., administer the drug on their own behalf) or a physician may administer the drug.

Various aspects of the disclosure are described in further detail in the following subsections. All patents, patent applications, references and other publications are incorporated by reference herein in their entirety.

IL-17 Antagonists

The various disclosed pharmaceutical compositions, regimens, processes, uses, methods and kits utilize an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof).

In one embodiment, the IL-17 antagonist, e.g., IL-17 binding molecule (e.g., IL-17 antibody or antigen binding fragment thereof, e.g., secukinumab), comprises at least one immunoglobulin heavy chain variable domain ($V_H$) comprising in sequence hypervariable regions CDR1, CDR2 and CDR3, said CDR1 having the amino acid sequence SEQ ID NO:1 (N-Y-W-M-N), said CDR2 having the amino acid sequence SEQ ID NO:2 (A-I-N-Q-D-G-S-E-K-Y-Y-V-G-S-V-K-G), and said CDR3 having the amino acid sequence SEQ ID NO:3 (D-Y-Y-D-I-L-T-D-Y-Y-I-H-Y-W-Y-F-D-L).

In one embodiment, the IL-17 antagonist, e.g., IL-17 binding molecule (e.g., IL-17 antibody or antigen binding fragment thereof, e.g., secukinumab), comprises at least one immunoglobulin light chain variable domain ($V_L$) comprising in sequence hypervariable regions CDR1', CDR2' and CDR3', said CDR1' having the amino acid sequence SEQ ID NO:4 (R-A-S-Q-S-V-S-S-S-Y-L-A), said CDR2' having the amino acid sequence SEQ ID NO:5 (G-A-S-S-R-A-T) and said CDR3' having the amino acid sequence SEQ ID NO:6 (Q-Q-Y-G-S-S-P-C-T).

In one embodiment, the IL-17 antagonist, e.g., IL-17 binding molecule (e.g., IL-17 antibody or antigen binding fragment thereof, e.g., secukinumab), comprises at least one immunoglobulin heavy chain variable domain ($V_H$) comprising in sequence hypervariable regions CDR1-x, CDR2-x and CDR3-x, said CDR1-x having the amino acid sequence SEQ ID NO:11 (G-F-T-F-S-N-Y-W-M-N), said CDR2-x having the amino acid sequence SEQ ID NO:12 (A-I-N-Q-D-G-S-E-K-Y-Y), and said CDR3-x having the amino acid sequence SEQ ID NO:13 (C-V-R-D-Y-Y-D-I-L-T-D-Y-Y-I-H-Y-W-Y-F-D-L-W-G).

In one embodiment, the IL-17 antagonist, e.g., IL-17 binding molecule (e.g., IL-17 antibody or antigen binding fragment thereof, e.g., secukinumab), comprises at least one immunoglobulin $V_H$ domain and at least one immunoglobulin $V_L$ domain, wherein: a) the immunoglobulin $V_H$ domain comprises: i) hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; or ii) hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the immunoglobulin $V_L$ domain comprises hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6 or.

In one embodiment, the IL-17 antagonist, e.g., IL-17 binding molecule (e.g., IL-17 antibody or antigen binding fragment thereof, e.g., secukinumab), comprises at least one immunoglobulin $V_H$ domain and at least one immunoglobulin $V_L$ domain, wherein: a) the at least one immunoglobulin $V_H$ domain comprises in sequence hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) the at least one immunoglobulin $V_L$ domain comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, t the IL-17 antagonist, e.g., IL-17 binding molecule (e.g., IL-17 antibody or antigen binding fragment thereof, e.g., secukinumab), comprises at least one immunoglobulin $V_H$ domain and at least one immunoglobulin $V_L$ domain, wherein: a) the at least one immunoglobulin $V_H$ domain comprises in sequence hypervariable regions CDR1-x, CDR2-x and CDR3-x, said CDR1-x having the amino acid sequence SEQ ID NO:11, said CDR2-x having the amino acid sequence SEQ ID NO:12, and said CDR3-x having the amino acid sequence SEQ ID NO:13; and b) the at least one immunoglobulin $V_L$ domain comprises in sequence hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6.

In one embodiment, the IL-17 antagonist, e.g., IL-17 binding molecule (e.g., IL-17 antibody or antigen binding fragment thereof, e.g., secukinumab), comprises: a) an immunoglobulin heavy chain variable domain ($V_H$) comprising the amino acid sequence set forth as SEQ ID NO:8; b) an immunoglobulin light chain variable domain ($V_L$) comprising the amino acid sequence set forth as SEQ ID NO:10; c) an immunoglobulin $V_H$ domain comprising the amino acid sequence set forth as SEQ ID NO:8 and an immunoglobulin $V_L$ domain comprising the amino acid sequence set forth as SEQ ID NO:10; d) an immunoglobulin $V_H$ domain comprising the hypervariable regions set forth as SEQ ID NO:1, SEQ ID NO:2, and SEQ ID NO:3 e) an immunoglobulin $V_L$ domain comprising the hypervariable regions set forth as SEQ ID NO:4, SEQ ID NO:5 and SEQ ID NO:6; f) an immunoglobulin $V_H$ domain comprising the hypervariable regions set forth as SEQ ID NO:11, SEQ ID NO:12 and SEQ ID NO:13; g) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; or h) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

For ease of reference the amino acid sequences of the hypervariable regions of the secukinumab monoclonal antibodies, based on the Kabat definition and as determined by the X-ray analysis and using the approach of Chothia and coworkers, is provided in Table 4, below.

TABLE 4

Amino acid sequences of the hypervariable regions of the secukinumab monoclonal antibodies. Amino acid highlighted in bold are part of the CDR loops, while those shown in plain style are part of the antibody framework.

| Light-chain | | |
|---|---|---|
| CDR1' | Kabat | R-A-S-Q-S-V-S-S-S-Y-L-A (SEQ ID NO: 4) |
| | Chothia/X-ray | R-A-**S-Q-S-V-S-S-S-Y**-L-A (SEQ ID NO: 4) |
| CDR2' | Kabat | G-A-S-S-R-A-T (SEQ ID NO: 5) |
| | Chothia/X-ray | **G-A-S**-S-R-A-T (SEQ ID NO: 5) |
| CDR3' | Kabat | Q-Q-Y-G-S-S-P-C-T (SEQ ID NO: 6) |
| | Chothia/X-ray | Q-Q-**Y-G-S-S**-P-C-T (SEQ ID NO: 6) |

TABLE 4-continued

Amino acid sequences of the hypervariable regions of the secukinumab monoclonal antibodies. Amino acid highlighted in bold are part of the CDR loops, while those shown in plain style are part of the antibody framework.

| Heavy-chain | | |
|---|---|---|
| CDR1 | Kabat | N-Y-W-M-N (SEQ ID NO: 1) |
| CDR1-x | Chothia/X-ray | **G-F-T-F-S-N**-Y-W-M-N (SEQ ID NO: 11) |
| CDR2 | Kabat | A-I-N-Q-D-G-S-E-K-Y-Y-V-G-S-V-K-G (SEQ ID NO: 2) |
| CDR2-x | Chothia/X-ray | A-I-**N-Q-D-G-S**-E-K-Y-Y (SEQ ID NO: 12) |
| CDR3 | Kabat | D-Y-Y-D-I-L-T-D-Y-Y-I-H-Y-W-Y-F-D-L (SEQ ID NO: 3) |
| CDR3-x | Chothia/X-ray | C-V-R-**D-Y-Y-D-I-L-T-D-Y-Y-I-H-Y-W-Y-F**-D-L-W-G (SEQ ID NO: 13) |

In preferred embodiments, the variable domains of both heavy and light chains are of human origin, for instance those of the secukinumab antibody which are shown in SEQ ID NO:10 (=variable domain of light chain, i.e., amino acid 1 to 109 of SEQ ID NO:10) and SEQ ID NO:8 (=variable domain of heavy chain, i.e., amino acid 1 to 127 of SEQ ID NO:8). The constant region domains preferably also comprise suitable human constant region domains, for instance as described in "Sequences of Proteins of Immunological Interest", Kabat E. A. et al, US Department of Health and Human Services, Public Health Service, National Institute of Health.

In some embodiments, the IL-17 antagonist, e.g., IL-17 binding molecule (e.g., IL-17 antibody or antigen binding fragment thereof, e.g., secukinumab), comprises the variable light domain of SEQ ID NO:10. In other embodiments, the IL-17 antagonist, e.g., IL-17 binding molecule (e.g., IL-17 antibody or antigen binding fragment thereof, e.g., secukinumab), comprises the variable heavy domain of SEQ ID NO:8. In other embodiments, the IL-17 antagonist, e.g., IL-17 binding molecule (e.g., IL-17 antibody or antigen binding fragment thereof, e.g., secukinumab), comprises the variable light domain of SEQ ID NO:10 and the variable heavy domain of SEQ ID NO:8. In some embodiments, the IL-17 antagonist, e.g., IL-17 binding molecule (e.g., IL-17 antibody or antigen binding fragment thereof, e.g., secukinumab), comprises the three CDRs of SEQ ID NO:10. In other embodiments, the IL-17 antagonist, e.g., IL-17 binding molecule (e.g., IL-17 antibody or antigen binding fragment thereof, e.g., secukinumab), comprises the three CDRs of SEQ ID NO:8. In other embodiments, an the IL-17 antagonist, e.g., IL-17 binding molecule (e.g., IL-17 antibody or antigen binding fragment thereof, e.g., secukinumab), comprises the three CDRs of SEQ ID NO:10 and the three CDRs of SEQ ID NO:8. CDRs of SEQ ID NO:8 and SEQ ID NO:10, according to both the Chothia and Kabat definition, may be found in Table 4.

In some embodiments, the IL-17 antagonist, e.g., IL-17 binding molecule (e.g., IL-17 antibody or antigen binding fragment thereof, e.g., secukinumab), comprises the light domain of SEQ ID NO:15. In other embodiments, the IL-17 antagonist, e.g., IL-17 binding molecule (e.g., IL-17 antibody or antigen binding fragment thereof, e.g., secukinumab), comprises the heavy domain of SEQ ID NO:17. In other embodiments, the IL-17 antagonist, e.g., IL-17 binding molecule (e.g., IL-17 antibody or antigen binding fragment thereof, e.g., secukinumab), comprises the light domain of SEQ ID NO:15 and the heavy domain of SEQ ID NO:17. In some embodiments, the IL-17 antagonist, e.g., IL-17 binding molecule (e.g., IL-17 antibody or antigen binding fragment thereof, e.g., secukinumab), comprises the three CDRs of SEQ ID NO:15. In other embodiments, the IL-17 antagonist, e.g., IL-17 binding molecule (e.g., IL-17 antibody or antigen binding fragment thereof, e.g., secukinumab), comprises the three CDRs of SEQ ID NO:17. In other embodiments, the IL-17 antagonist, e.g., IL-17 binding molecule (e.g., IL-17 antibody or antigen binding fragment thereof, e.g., secukinumab), comprises the three CDRs of SEQ ID NO: 15 and the three CDRs of SEQ ID NO:17. CDRs of SEQ ID NO:15 and SEQ ID NO:17, according to both the Chothia and Kabat definition, may be found in Table 4.

Hypervariable regions may be associated with any kind of framework regions, though preferably are of human origin. Suitable framework regions are described in Kabat E. A. et al, ibid. The preferred heavy chain framework is a human heavy chain framework, for instance that of the secukinumab antibody. It consists in sequence, e.g., of FR1 (amino acid 1 to 30 of SEQ ID NO:8), FR2 (amino acid 36 to 49 of SEQ ID NO:8), FR3 (amino acid 67 to 98 of SEQ ID NO:8) and FR4 (amino acid 117 to 127 of SEQ ID NO:8) regions. Taking into consideration the determined hypervariable regions of secukinumab by X-ray analysis, another preferred heavy chain framework consists in sequence of FR1-x (amino acid 1 to 25 of SEQ ID NO:8), FR2-x (amino acid 36 to 49 of SEQ ID NO:8), FR3-x (amino acid 61 to 95 of SEQ ID NO:8) and FR4 (amino acid 119 to 127 of SEQ ID NO:8) regions. In a similar manner, the light chain framework consists, in sequence, of FR1' (amino acid 1 to 23 of SEQ ID NO:10), FR2' (amino acid 36 to 50 of SEQ ID NO:10), FR3' (amino acid 58 to 89 of SEQ ID NO:10) and FR4' (amino acid 99 to 109 of SEQ ID NO:10) regions.

In one embodiment, the IL-17 antagonist, e.g., IL-17 binding molecule (e.g., IL-17 antibody or antigen binding fragment thereof, e.g., secukinumab) is selected from a human anti-IL-17 antibody, which comprises at least: a) an immunoglobulin heavy chain or fragment thereof which comprises a variable domain comprising in sequence the hypervariable regions CDR1, CDR2 and CDR3 and the constant part or fragment thereof of a human heavy chain; said CDR1 having the amino acid sequence SEQ ID NO:1, said CDR2 having the amino acid sequence SEQ ID NO:2, and said CDR3 having the amino acid sequence SEQ ID NO:3; and b) an immunoglobulin light chain or fragment thereof, which comprises a variable domain comprising in sequence the hypervariable regions CDR1', CDR2', and CDR3' and the constant part or fragment thereof of a human light chain, said CDR1' having the amino acid sequence SEQ ID NO: 4, said CDR2' having the amino acid sequence SEQ ID NO:5, and said CDR3' having the amino acid sequence SEQ ID NO:6.

In one embodiment, the IL-17 antagonist, e.g., IL-17 binding molecule (e.g., IL-17 antibody or antigen binding fragment thereof, e.g., secukinumab) is selected from a single chain binding molecule, which comprises an antigen binding site comprising: a) a first domain comprising in sequence the hypervariable regions CDR1, CDR2 and CDR3, said CDR1 having the amino acid sequence SEQ ID NO:1, said CDR2 having the amino acid sequence SEQ ID NO:2, and said CDR3 having the amino acid sequence SEQ ID NO:3; and b) a second domain comprising the hypervariable regions CDR1', CDR2' and CDR3', said CDR1' having the amino acid sequence SEQ ID NO:4, said CDR2' having the amino acid sequence SEQ ID NO:5, and said CDR3' having the amino acid sequence SEQ ID NO:6; and c) a peptide linker which is bound either to the N-terminal extremity of the first domain and to the C-terminal extremity of the second domain or to the C-terminal extremity of the first domain and to the N-terminal extremity of the second domain.

Alternatively, the IL-17 antagonist, e.g., IL-17 binding molecule (e.g., IL-17 antibody or antigen binding fragment thereof, e.g., secukinumab) may comprise at least one antigen binding site comprising at least one immunoglobulin heavy chain variable domain ($V_H$) which comprises in sequence: a) hypervariable regions CDR1 (SEQ ID NO:1), CDR2 (SEQ ID NO:2) and CDR3 (SEQ ID NO:3); or b) hypervariable regions $CDR1_i$, $CDR2_i$, $CDR3_i$, said hypervariable region $CDR1_i$ differs by 3, preferably 2, more preferably 1 amino acid(s) from the hypervariable region of CDR1 as shown in SEQ ID NO:1, said hypervariable region $CDR2_i$ differs by 3, preferably 2, more preferably 1 amino acid(s) from the hypervariable region of CDR2 as shown in SEQ ID NO:2; and said hypervariable region CDR3; differs by 3, preferably 2, more preferably 1 amino acid(s) from the hypervariable region of CDR3 as shown in SEQ ID NO:3; and said binding IL-17 molecule is capable of inhibiting the activity of about 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Similarly, the IL-17 antagonist, e.g., IL-17 binding molecule (e.g., IL-17 antibody or antigen binding fragment thereof, e.g., secukinumab) may comprise at least one antigen binding site comprising at least one immunoglobulin heavy chain variable domain ($V_H$) which comprises in sequence: a) hypervariable regions CDR1-x (SEQ ID NO: 11), CDR2-x (SEQ ID NO:12) and CDR3-x (SEQ ID NO:13); or b) hypervariable regions $CDR1_i$-x, $CDR2_i$-x, $CDR3_i$-x, said hypervariable region $CDR1_i$-x differs by 3, preferably 2, more preferably 1 amino acid(s) from the hypervariable region of CDR1-x as shown in SEQ ID NO: 11, said hypervariable region $CDR2_i$-x differs by 3, preferably 2, more preferably 1 amino acid(s) from the hypervariable region of CDR2-x as shown in SEQ ID NO:12; and said hypervariable region $CDR3_i$-x differs by 3, preferably 2, more preferably 1 amino acid(s) from the hypervariable region of CDR3-x as shown in SEQ ID NO:13; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Similarly, the IL-17 antagonist, e.g., IL-17 binding molecule (e.g., IL-17 antibody or antigen binding fragment thereof, e.g., secukinumab) may comprise at least one antigen binding site comprising at least one immunoglobulin light chain variable domain ($V_L$) which comprises in sequence: a) hypervariable regions CDR'1 (SEQ ID NO:4), CDR'2 (SEQ ID NO:5) and CDR'3 (SEQ ID NO:6); or b) hypervariable regions $CDR1'_i$, $CDR2'_i$, $CDR3'_i$, said hypervariable region $CDR'1_i$ differs by 3, preferably 2, more preferably 1 amino acid(s) from the hypervariable region of CDR'1 as shown in SEQ ID NO:4, said hypervariable region CDR'2; differs by 3, preferably 2, more preferably 1 amino acid(s) from the hypervariable region of CDR'2 as shown in SEQ ID NO:5; and said hypervariable region $CDR'3_i$ differs by 3, preferably 2, more preferably 1 amino acid(s) from the hypervariable region of CDR'3 as shown in SEQ ID NO:6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Alternatively, the IL-17 antagonist, e.g., IL-17 binding molecule (e.g., IL-17 antibody or antigen binding fragment thereof, e.g., secukinumab) may comprise both heavy ($V_H$) and light chain ($V_L$) variable domains and said IL-17 binding molecule having at least one antigen binding site comprising: a) an immunoglobulin heavy chain variable domain ($V_H$) which comprises in sequence hypervariable regions CDR1 (SEQ ID NO:1), CDR2 (SEQ ID NO:2) and CDR3 (SEQ ID NO:); and an immunoglobulin light chain variable domain ($V_L$) which comprises in sequence hypervariable regions CDR1' (SEQ ID NO:4), CDR2' (SEQ ID NO:5) and CDR3' (SEQ ID NO:6); or b) an immunoglobulin heavy chain variable domain ($V_H$) which comprises in sequence hypervariable regions $CDR1_i$, $CDR2_i$, and $CDR3_i$, said hypervariable region $CDR1_i$ differs by 3, preferably 2, more preferably 1 amino acid(s) from the hypervariable region of CDR1 as shown in SEQ ID NO:1, said hypervariable region $CDR2_i$ differs by 3, preferably 2, more preferably 1 amino acid(s) from the hypervariable region of CDR2 as shown in SEQ ID NO:2; and said hypervariable region $CDR3_i$ differs by 3, preferably 2, more preferably 1 amino acid(s) from the hypervariable region of CDR3 as shown in SEQ ID NO:3; and an immunoglobulin light chain variable domain ($V_L$) which comprises in sequence hypervariable regions $CDR1'_i$, $CDR2'_i$, $CDR3'_i$, said hypervariable region $CDR'1_i$ differs by 3, preferably 2, more preferably 1 amino acid(s) from the hypervariable region of CDR'1 as shown in SEQ ID NO:4, said hypervariable region $CDR'2_i$ differs by 3, preferably 2, more preferably 1 amino acid(s) from the hypervariable region of CDR'2 as shown in SEQ ID NO:5; and said hypervariable region $CDR'3_i$ differs by 3, preferably 2, more preferably 1 amino acid(s) from the hypervariable region of CDR'3 as shown in SEQ ID NO:6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

Alternatively, the IL-17 antagonist, e.g., IL-17 binding molecule (e.g., IL-17 antibody or antigen binding fragment thereof, e.g., secukinumab) may comprise both heavy ($V_H$) and light chain ($V_L$) variable domains and said IL-17 binding molecule comprises at least one antigen binding site comprising: a) an immunoglobulin heavy chain variable domain ($V_H$) which comprises in sequence hypervariable regions CDR1-x (SEQ ID NO:11), CDR2-x (SEQ ID NO:12) and CDR3-x (SEQ ID NO:13); and an immunoglobulin light chain variable domain ($V_L$) which comprises in sequence hypervariable regions CDR1' (SEQ ID NO:4), CDR2' (SEQ ID NO: 5) and CDR3' (SEQ ID NO:6); or b) an immunoglobulin heavy chain variable domain ($V_H$) which comprises in sequence hypervariable regions $CDR1_i$-x, $CDR2_i$-x, and $CDR3_i$-x, said hypervariable region hypervariable regions $CDR1_i$-x, $CDR2_i$-x, $CDR3_i$-x, said hypervariable region $CDR1_i$-x differs by 3, preferably 2, more preferably 1 amino acid(s) from the hypervariable region of CDR1-x as shown in SEQ ID NO: 11, said hypervariable region $CDR2_i$-x differs by 3, preferably 2, more preferably 1 amino acid(s) from the hypervariable region of CDR2-x as shown in SEQ ID NO:12; and said hypervariable region $CDR3_i$-x differs by 3, preferably 2, more preferably 1 amino acid(s) from the hypervariable region of CDR3-x as shown in SEQ ID NO: 13; and an immunoglobulin light chain variable domain ($V_L$) which comprises in sequence hypervariable regions $CDR1'_i$, $CDR2'_i$, $CDR3'_i$, said hypervariable region $CDR'1_i$ differs by 3, preferably 2, more preferably 1 amino acid(s) from the hypervariable region of CDR'1 as shown in SEQ ID NO: 4, said hypervariable region $CDR'2_i$ differs by 3, preferably 2, more preferably 1 amino acid(s) from the hypervariable region of CDR'2 as shown in SEQ ID NO:5; and said hypervariable region $CDR'3_i$ differs by 3, preferably 2, more preferably 1 amino acid(s) from the hypervariable region of CDR'3 as shown in SEQ ID NO:6; and said binding IL-17 molecule is capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50%, said inhibitory activity being measured on IL-6 production induced by hu-IL-17 in human dermal fibroblasts.

A human IL-17 antibody disclosed herein may comprise a heavy chain that is substantially identical to that set forth as SEQ ID NO:17 and a light chain that is substantially identical to that set forth as SEQ ID NO:15. A human IL-17 antibody disclosed herein may comprise a heavy chain that comprises SEQ ID NO:17 and a light chain that comprises SEQ ID NO:15.

A human IL-17 antibody disclosed herein may comprise: a) one heavy chain which comprises a variable domain having an amino acid sequence substantially identical to that shown in SEQ ID NO:8 and the constant part of a human heavy chain; and b) one light chain which comprises a variable domain having an amino acid sequence substantially identical to that shown in SEQ ID NO:10 and the constant part of a human light chain.

The inhibition of the binding of IL-17 to its receptor may be conveniently tested in various assays including such assays as described in WO 2006/013107. By the term "to the same extent" is meant that the reference and the derivative molecules exhibit, on a statistical basis, essentially identical IL-17 inhibitory activity in one of the assays referred to herein (see Example 1 of WO 2006/013107). For example, the IL-17 binding molecules disclosed herein typically have $IC_{50s}$ for the inhibition of human IL-17 on IL-6 production induced by human IL-17 in human dermal fibroblasts which are below about 10 nM, more preferably about 9, 8, 7, 6, 5, 4, 3, 2, or about 1 nM of that of, preferably substantially the same as, the $IC_{50}$ of the corresponding reference molecule when assayed as described in Example 1 of WO 2006/013107. Alternatively, the assay used may be an assay of competitive inhibition of binding of IL-17 by soluble IL-17 receptors (e.g. the human IL-17 R/Fc constructs of Example 1 of WO 2006/013107) and the IL-17 binding molecules of the disclosure.

The disclosure also includes IL-17 antagonists, e.g., IL-17 binding molecules (e.g., IL-17 antibody or antigen binding fragment thereof, e.g., secukinumab) in which one or more of the amino acid residues of CDR1, CDR2, CDR3, CDR1-x, CDR2-x, CDR3-x, CDR1', CDR2' or CDR3' or the frameworks, typically only a few (e.g., 1-4), are changed; for instance by mutation, e.g., site directed mutagenesis of the corresponding DNA sequences. The disclosure includes the DNA sequences coding for such changed IL-17 binding molecules. In particular the disclosure includes IL-17 binding molecules in which one or more residues of CDR1' or CDR2' have been changed from the residues shown in SEQ ID NO:4 (for CDR1') and SEQ ID NO:5 (for CDR2').

The disclosure also includes IL-17 antagonists, e.g., IL-17 binding molecules (e.g., IL-17 antibody or antigen binding fragment thereof, e.g., secukinumab) that have binding specificity for human IL-17, in particular IL-17 antibodies capable of inhibiting the binding of IL-17 to its receptor and IL-17 antibodies capable of inhibiting the activity of 1 nM (=30 ng/ml) human IL-17 at a concentration of about 50 nM or less, about 20 nM or less, about 10 nM or less, about 5 nM or less, about 2 nM or less, or more preferably of about 1 nM or less of said molecule by 50% (said inhibitory activity being measured on IL-6 production induced by hu-IL-17 in human dermal fibroblasts).

The disclosure provides methods for treating RA, comprising administering a therapeutically effective amount of an IL-17 antagonist, e.g., IL-17 binding molecule (e.g., IL-17 antibody or antigen binding fragment thereof, e.g., secukinumab) to a subject suffering from RA, e.g., a high risk RA patient. In some embodiments, the IL-17 antibody, e.g., secukinumab, binds to an epitope of mature human IL-17 comprising Leu74, Tyr85, His86, Met87, Asn88, Val124, Thr125, Pro126, Ile127, Val128, His129. In some embodiments, the IL-17 antibody, e.g., secukinumab, binds to an epitope of mature human IL-17 comprising Tyr43, Tyr44, Arg46, Ala79, Asp80. In some embodiments, the IL-17 antibody, e.g., secukinumab, binds to an epitope of an IL-17 homodimer having two mature human IL-17 chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain. The residue numbering scheme used to define these epitopes is based on residue one being the first amino acid of the mature protein (ie., IL-17A lacking the 23 amino acid N-terminal signal peptide and beginning with Glycine). The sequence for immature IL-17A is set forth in the Swiss-Prot entry Q16552.

In some embodiments, the IL-17 antibody has a $K_D$ of about 100-200 μM. In some embodiments, the IL-17 antibody has an $IC_{50}$ of about 0.4 nM for in vitro neutralization of the biological activity of about 0.67 nM human IL-17A. In some embodiments, the absolute bioavailability of subcutaneously (s.c.) administered IL-17 antibody has a range of about 60-about 80%, e.g., about 76%. In some embodiments, the IL-17 antagonist, e.g., an IL-17 binding molecule (e.g., an IL-17 antibody, such as secukinumab) or an IL-17 receptor binding molecule (e.g., an IL-17 receptor antibody) has an elimination half-life of about 4 weeks (e.g., about 23 to about 30 days, e.g., about 30 days). In some embodiments, the IL-17 antagonist, e.g., an IL-17 binding molecule (e.g., an IL-17 antibody, such as secukinumab) or an IL-17 receptor binding molecule (e.g., an IL-17 receptor antibody) has a $T_{max}$ of about 7-8 days.

In some embodiments of the disclosed methods, uses, pharmaceutical compositions, kits, assays, and treatment regimens, the IL-17 antagonist is selected from the group consisting of: a) an IL-17 binding molecule or an IL-17 receptor binding molecule; b) secukinumab; c) an IL-17 antibody that binds to an epitope of IL-17 comprising Leu74, Tyr85, His86, Met87, Asn88, Val124, Thr125, Pro126, Ile127, Val128, His129; d) an IL-17 antibody that binds to an epitope of IL-17 comprising Tyr43, Tyr44, Arg46, Ala79, Asp80; e) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; f) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 pM, and wherein the IL-17 binding molecule has an in vivo half-life of about 4 weeks; and g) an IL-17 antibody that comprises an antibody selected from the group consisting of: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; and viii) an immunoglobulin $V_H$ domain comprising the hypervariable regions set forth as SEQ ID NO:11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

Particularly preferred IL-17 antagonists, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof) for use in the disclosed methods, uses, kits, etc. are human antibodies, especially secukinumab as described in Examples 1 and 2 of WO 2006/013107. Secukinumab (AIN457) is a recombinant high-affinity, fully human monoclonal anti-human interleukin-17A (IL-17A, IL-17) antibody of the IgG1/kappa isotype. Secukinumab (see, e.g., WO2006/013107 and WO2007/117749) has a very high affinity for IL-17, i.e., a $K_D$ of about 100-200 pM and an $IC_{50}$ for in vitro neutralization of the biological activity of about 0.67 nM human IL-17A of about 0.4 nM. Thus, secukinumab inhibits antigen at a molar ratio of about 1:1. This high binding affinity makes the secukinumab antibody particularly suitable for therapeutic applications. Furthermore, it has been determined that secukinumab has a very long half life, i.e., about 4 weeks, which allows for prolonged periods between administration, an exceptional property when treating chronic life-long disorders, such as rheumatoid arthritis (RA).

Treatment Regimens, Methods of Treatment, Pharmaceutical Compositions and Uses

The disclosed IL-17 antagonists, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof) are useful for the treatment, prevention, or amelioration of inflammatory arthritis (e.g., rheumatoid arthritis (RA), spondyloarthropathy, ankylosing spondylitis, and psoriatic arthritis). Thus, such molecules are useful in inducing changes in the signs and symptoms of arthritis & structural changes, preventing further joint erosion, improving joint structure, etc. In some embodiments, the patient having inflammatory arthritis is an RA patient, e.g., a high risk RA patient.

The IL-17 antagonists, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof) may be used in vitro, ex vivo, or incorporated into pharmaceutical compositions and administered to individuals (e.g., human subjects) in vivo to treat, ameliorate, or prevent RA, e.g., in high risk RA patients. A pharmaceutical composition will be formulated to be compatible with its intended route of administration (e.g., oral compositions generally include an inert diluent or an edible carrier). Other nonlimiting examples of routes of administration include parenteral (e.g., intravenous), intradermal, subcutaneous, oral (e.g., inhalation), transdermal (topical), transmucosal, and rectal administration. The pharmaceutical compositions compatible with each intended route are well known in the art.

The IL-17 antagonists, e.g., IL-17 binding molecules (e.g., IL-17 antibody or antigen binding fragment thereof, e.g., secukinumab) or IL-17 receptor binding molecules (e.g., IL-17 antibody or antigen binding fragment thereof) may be used as a pharmaceutical composition when combined with a pharmaceutically acceptable carrier. Such a composition may contain, in addition to an IL-17 antagonist (e.g., secukinumab) carriers, various diluents, fillers, salts, buffers, stabilizers, solubilizers, and other materials well known in the art. The characteristics of the carrier will depend on the route of administration.

The pharmaceutical compositions for use in the disclosed methods may also contain additional therapeutic agents for treatment of the particular targeted disorder. For example, a pharmaceutical composition may also include anti-inflammatory agents. Such additional factors and/or agents may be included in the pharmaceutical composition to produce a synergistic effect with the IL-17 antagonist (e.g., secukinumab), or to minimize side effects caused by the IL-17 binding molecules.

The pharmaceutical composition of the disclosure may be in the form of a liposome in which the IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is combined, in addition to other pharmaceutically acceptable carriers, with amphipathic agents such as lipids that exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, etc.

In practicing the methods of treatment, regimena, uses, etc. of the present disclosure, a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is administered to a subject, e.g., a mammal (e.g., a human). An IL-17 antagonist (e.g., secukinumab) may be administered in accordance with the method of the disclosure either alone or in combination with other therapies, such as, e.g., in combination with additional therapies for inflammation. When coadministered with one or more agents, an IL-17 antagonist (e.g., secukinumab) may be administered either simultaneously with the other agent, or sequentially. If administered sequentially, the attending physician will decide on the appropriate sequence of administering the IL-17 antagonist (e.g., secukinumab) in combination with other agents.

When a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is administered orally, the binding agent will be in the form of a tablet, capsule, powder, solution or elixir. When administered in tablet form, the pharmaceutical composition of the disclosure may additionally contain a solid carrier such as a gelatin or an adjuvant. When administered in liquid form, a liquid carrier such as water, petroleum, oils of animal or plant origin such as peanut oil (exercising caution in relation to peanut allergies), mineral oil, soybean oil, or sesame oil, or synthetic oils may be added. The liquid form of the pharmaceutical composition may further contain components such as physiological saline solution, dextrose or other saccharide solution, or glycols such as ethylene glycol, propylene glycol, or polyethylene glycol.

When a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is administered by intravenous, cutaneous or subcutaneous injection, the IL-17 binding molecule will be in the form of a pyrogen-free, parenterally acceptable solution. A pharmaceutical composition for intravenous, cutaneous, or subcutaneous injection may contain, in addition to the IL-17 antagonist (e.g., secukinumab), an isotonic vehicle such as sodium chloride, Ringer's, dextrose, dextrose and sodium chloride, lactated Ringer's, or other vehicle as known in the art.

Pharmaceutical compositions for use in the disclosed methods may be manufactured in conventional manner. In one embodiment, the pharmaceutical composition is preferably provided in lyophilized form. For immediate administration it is dissolved in a suitable aqueous carrier, for example sterile water for injection or sterile buffered physiological saline. If it is considered desirable to make up a solution of larger volume for administration by infusion rather than a bolus injection, may be advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution. Other formulations comprise liquid or lyophilized formulation.

The appropriate dosage will, of course, vary depending upon, for example, the particular IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to be employed, the host, the mode of administration and the nature and severity of the condition being treated, and on the nature of prior treatments that the patient has undergone. Ultimately, the attending health care provider will decide the amount of the IL-17 antagonist (e.g., secukinumab) with which to treat each individual subject. In some embodiments, the attending health care provider may administer low doses of the IL-17 binding molecule and observe the subject's response. In other embodiments, the initial dose(s) of IL-17 antagonist (e.g., secukinumab) administered to a subject are high, and then are titrated downward until signs of relapse occur. Larger doses of the IL-17 antagonist (e.g., secukinumab) may be administered until the optimal therapeutic effect is obtained for the subject, and at that point the dosage is not generally increased further.

An IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is conveniently administered parenterally, intravenously, e.g. into the antecubital or other peripheral vein, intramuscularly, or subcutaneously. The duration of intravenous (i.v.) therapy using a pharmaceutical composition of the present disclosure will vary, depending on the severity of the disease being treated and the condition and personal response of each individual patient. Also contemplated is subcutaneous (s.c.) therapy using a pharmaceutical composition of the present disclosure. The health care provider will decide on the appropriate duration of i.v. or s.c. therapy and the timing of administration of the therapy, using the pharmaceutical composition of the present disclosure.

Satisfactory results (treatment, prophylaxis, delay of onset of symptoms) are generally indicated to be obtained at dosages from about 0.05 mg to about 30 mg per kilogram body weight, more usually from about 0.1 mg to about 20 mg per kilogram body weight. The frequency of dosing may be in the range from about once per day up to about once every three months, e.g., in the range from about once every 2 weeks up to about once every 12 weeks, e.g., once every four to eight weeks. The dosing frequency will depend on, inter alia, the phase of the treatment regimen.

The use of antibodies as the active ingredient of pharmaceuticals is now widespread, including the products HERCEPTIN™ (trastuzumab), RITUXAN™ (rituximab), SYNAGIS™ (palivizumab), etc. Techniques for purification of antibodies to a pharmaceutical grade are well known in the art. Antibodies, e.g., antibodies to IL-17, are typically formulated either in aqueous form ready for parenteral administration or as lyophilisates for reconstitution with a suitable diluent prior to administration. In some embodiments of the disclosed methods and uses, the IL-17 antagonist, e.g., IL-17 antibody, e.g., secukinumab, is formulated as a lyophilisate. Suitable lyophilisate formulations can be reconstituted in a small liquid volume (e.g., 2 ml or less) to allow subcutaneous administration and can provide solutions with low levels of antibody aggregation. The composition will usually be sterile, at least at the time of its formation. The composition will usually be non pyrogenic e.g. containing <1 EU (endotoxin unit, a standard measure) per dose, and preferably <0.1 EU per dose. The composition is preferably gluten free. Within formulations disclosed herein, antibodies preferably makes up at least 80% by weight (e.g. at least 90%, 95%, 97%, 98%, 99% or more) of the total protein in the formulation. The antibody is thus in purified form.

Lyophilisates

Techniques for lyophilisation of antibodies are well known in the art, e.g., see Rey & May (2004) Freeze-Drying/Lyophilization Of Pharmaceutical & Biological Products ISBN 0824748689, WO92/15331, US patent application 2008/0286280, WO03/041637, WO2008/116103, WO2008/029908, WO2007/074880, WO03/009817, and WO98/022136. For example, antibody products SYNAGIS™, REMICADE™, RAPTIVA™, SIMULECT™, XOLAIR™ and HERCEPTIN™ are supplied as lyophilisates. These antibodies are reconstituted to various final concentrations, e.g. SIMULECT™, is reconstituted to a concentration of 4 mg/ml antibody, REMICADE™ is reconstituted to a concentration of 10 mg/ml, HERCEPTIN™ to 21 mg/ml, SYNAGIS™ and RAPTIVA™ to 100 mg/ml, and XOLAIR™ to 125 mg/ml.

Lyophilisates of the disclosure can be reconstituted to give aqueous compositions with an anti-IL-17 antibody concentration of at least about 15 mg/ml. The antibody concentration can be much higher than about 15 mg/ml, e.g., >about 15 mg/ml, >about 20 mg/ml, >about 25 mg/ml, >about 50 mg/ml, >about 75 mg/ml, >about 100 mg/ml, >about 125 mg/ml, >about 150 mg/ml, >about 300 mg/ml or higher.

The lyophilisate may include, in addition to the anti-IL-17 antibody, further components such as one or more of the following: (i) a sugar; (ii) a buffering agent; (iii) a surfactant; and (iv) a stabilizing agent. Inclusion of each of such additional components (i), (ii) and (iii) is typical, and can give compositions with low aggregation of the anti-IL-17 antibody. Inclusion of component (iv) is advantageous because it has been shown to further reduce aggregation after storage.

When present, components (i) to (iv) will be at a pre-lyophilisation concentration sufficient to maintain the anti-IL-17 antibody in a form which is active and soluble after storage (under normal conditions) and reconstitution. The components will also be present after reconstitution.

Suitable sugars for use with the invention include, but are not limited to, monosaccharides, disaccharides and trisaccharides. For example, the sugar may be sucrose, trehalose, raffinose, maltose, sorbitol or mannitol. The sugar may be a sugar alcohol or an amino sugar. Sucrose and trehalose (e.g., at a concentration of about 175 mM to about 300 mM, e.g., about 175 mM, about 180 mM, about 185 mM, about 190 mM, about 195 mM, about 200 mM, about 225 mM, about 250 mM, about 275 mM, about 300 mM) are particularly useful.

Suitable buffering agents for use with the invention include, but are not limited to, a histidine buffer, a citrate buffer, a phosphate buffer, a succinate buffer, an acetate buffer, or a Tris buffer. A histidine buffer (e.g., at a concentration of about 5 mM to about 50 mM, e.g., about 5 mM, about 10 mM, about 15 mM, about 20 mM, about 25 mM, about 30 mM, about 35 mM, about 40 mM, about 45 mM, about 50 mM) is particularly useful.

Suitable surfactants for use with the invention include, but are not limited to, non ionic surfactants, ionic surfactants and zwitterionic surfactants. Typical surfactants for use with the invention include, but are not limited to, sorbitan fatty acid esters (e.g., sorbitan monocaprylate, sorbitan monolaurate, sorbitan monopalmitate), sorbitan trioleate, glycerine fatty acid esters (e.g., glycerine monocaprylate, glycerine monomyristate, glycerine monostearate), polyglycerine fatty acid esters (e.g., decaglyceryl monostearate, decaglyceryl distearate, decaglyceryl monolinoleate), polyoxyethylene sorbitan fatty acid esters (e.g., polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate), polyoxyethylene sorbitol fatty acid esters (e.g., polyoxyethylene sorbitol tetrastearate, polyoxyethylene sorbitol tetraoleate), polyoxyethylene glycerine fatty acid esters (e.g., polyoxyethylene glyceryl monostearate), polyethylene glycol fatty acid esters (e.g., polyethylene glycol distearate), polyoxyethylene alkyl ethers (e.g., polyoxyethylene lauryl ether), polyoxyethylene polyoxypropylene alkyl ethers (e.g., polyoxyethylene polyoxypropylene glycol, polyoxyethylene polyoxypropylene propyl ether, polyoxyethylene polyoxypropylene cetyl ether), polyoxyethylene alkylphenyl ethers (e.g., polyoxyethylene nonylphenyl ether), polyoxyethylene hydrogenated castor oils (e.g. polyoxyethylene castor oil, polyoxyethylene hydrogenated castor oil), polyoxyethylene beeswax derivatives (e.g., polyoxyethylene sorbitol beeswax), polyoxyethylene lanolin derivatives (e.g., polyoxyethylene lanolin), and polyoxyethylene fatty acid amides (e.g., polyoxyethylene stearic acid amide); C10-C18 alkyl sulfates (e.g., sodium cetyl sulfate, sodium lauryl sulfate, sodium oleyl sulfate), polyoxyethylene C10-C18 alkyl ether sulfate with an average of 2 to 4 moles of ethylene oxide units added (e.g., sodium polyoxyethylene lauryl sulfate), and C1-C18 alkyl sulfosuccinate ester salts (e.g., sodium lauryl sulfosuccinate ester); and natural surfactants such as lecithin, glycerophospholipid, sphingophospholipids (e.g., sphingomyelin), and sucrose esters of C12-C18 fatty acids. A composition may include one or more of these surfactants. Preferred surfactants are polyoxyethylene sorbitan fatty acid esters e.g. polysorbate 20, 40, 60 or 80. Polysorbate 80 (Tween 80) (e.g., at a concentration of about 0.01%-about 0.1%, e.g., about 0.02%, about 0.04%, about 0.06%, about 0.08%, about 0.1%) is particularly useful.

A lyophilisate may include active ingredients in addition to the antibody. For instance, further pharmacological agents may be included, such as chemotherapeutic compounds. For instance, methotrexate may be included, and it is known to include methotrexate sodium in lyophilisates.

The pH of an aqueous antibody formulation prior to lyophilisation may be in the range 4.0-8.0, which a pH in the range about 5.5-about 7.4 being typical, e.g., about 5.5, about 5.6, about 5.7, about 5.8, about 5.9, about 6, about 6.2, about 6.4, about 6.6, about 6.7, about 6.8, about 6.9, about 7.0, about 7.1, about 7.2, about 7.3, about 7.4.

Disclosed are antibody lyophilisates comprising about 25 mg, 50 mg, 75 mg, 150 mg, or 300 mg of an anti-IL-17 antibody—preferably 75 mg-150 mg (e.g., 75 mg or 150 mg) of an anti-IL-17 antibody. Disclosed are also lyophilisates comprising: an IL-17 antibody, e.g., secukinumab; a sugar; a buffering agent; and a surfactant. The composition may also include a stabilizing agent.

Disclosed are also processes for preparing a lyophilisate, comprising steps of: (i) preparing an aqueous solution comprising an IL-17 antibody, e.g., secukinumab, a sugar, a buffering agent, a surfactant, and optionally a stabilizing agent; and (ii) lyophilising the aqueous solution.

Reconstitutes

Before a lyophilisate can be administered to a patient it should be reconstituted with a liquid reconstituent (e.g., an aqueous liquid) to provide a liquid composition (hereinafter a "reconstitute").

Lyophilisates may be reconstituted with various volumes (e.g., 0.25 ml, 0.5 ml, 1.0 ml, 1.5 ml, etc.) of a reconstituent (e.g., an aqueous reconstituent, e.g., water). This step permits antibody and other components in the lyophilisate to re-dissolve to give a solution which is suitable for injection to a patient. The volume of aqueous material used for reconstitution dictates the concentration of antibody in a resulting pharmaceutical composition, and may also determine the route of administration. Reconstitution with a smaller volume of reconstituent than the pre-lyophilisation volume provides a composition which is more concentrated than before lyophilisation. As mentioned above, lyophilisates of the invention can be reconstituted to give aqueous compositions with an anti-IL-17 antibody concentration of at least about 75 mg/ml (or higher), and the volume of reconstituent will be selected accordingly.

Disclosed herein are reconstitutes comprising an anti-IL-17 antibody, wherein the reconstitute has an antibody concentration of at least about 25 mg/ml, 50 mg/ml, 75 mg/ml, 150 mg/ml, or 300 mg/ml-preferably 75 mg/ml-150 mg/ml (e.g., 75 mg/ml or 150 mg/ml). Ideally the volume of the reconstitute is small, e.g., 0.25-2.0 ml, in order to facilitate subcutaneous administration of the IL-17 antagonist.

Typical reconstitutes for lyophilised antibodies include sterile water or buffer, optionally containing a preservative. If the lyophilisate includes a buffering agent, then the reconstituent may include further buffering agent (which may be the same as or different from the lyophilisate's buffering agent) or it may instead include no buffering agent (e.g. WFI, physiological saline). A reconstitute may include pharmacological agents, such as chemotherapeutic compounds, facilitating co delivery together with the antibody.

When present, components (i) to (iv) mentioned above will be at a concentration sufficient to maintain the anti-IL-17 antibody in active soluble form, after reconstitution, under normal storage conditions while retaining pharmaceutical acceptability at the point of use.

In addition to antibody and water, reconstitutes may include further components, derived from the lyophilisate and/or the reconstituent. Such components include, but are not limited to, buffers, salts, stabilizing agents, glycerol, alcohols, preservatives, surfactants, etc. A thorough discussion of such pharmaceutical ingredients is available in Gennaro (2000) Remington: The Science and Practice of Pharmacy. 20th edition, ISBN: 0683306472.

Disclosed are reconstitute pharmaceutical compositions comprising: an IL-17 antibody, e.g., secukinumab; a sugar; a buffering agent; and a surfactant. The composition may also include a stabilizing agent. Disclosed are also processes for preparing a reconstitute, comprising mixing a lyophilisate with an aqueous reconstituent, wherein the lyophilisate comprises an IL-17 antibody, e.g., secukinumab, a sugar, a buffering agent, a surfactant, and optionally a stabilizing agent.

Disclosed herein are methods of treating rheumatoid arthritis (RA), comprising administering a therapeutically effective amount of an IL-17 antagonist to a high risk RA patient.

Disclosed herein are also methods of treating rheumatoid arthritis (RA), comprising: a) selecting a patient for treatment on the basis of the patient being a high risk RA patient; and b) administering a therapeutically effective amount of an IL-17 antagonist to the patient.

Disclosed herein are methods of treating rheumatoid arthritis (RA), comprising: a) assaying a sample from a patient for: i. rheumatoid factor (RF), anti-citrullinated protein antibody (ACPA), or RF and ACPA; and ii. C-reactive protein (CRP), an erythrocyte sedimentation rate (ESR), or both CRP and an ESR; and b) thereafter, administering the patient an IL-17 antagonist to the patient if the patient is RF+, ACPA+, or RF+ and ACPA+ and the patient has a high level of CRP, a high ESR, or a high level of CRP and a high ESR.

Disclosed herein are methods of treating rheumatoid arthritis (RA), comprising administering a therapeutically effective amount of an IL-17 antagonist to a patient, provided that the patient is selected for treatment on the basis of: a) being RF+, ACPA+, or both RF+ and ACPA+; and b) having a high level of CRP, a high ESR, or both a high level of CRP and a high ESR. In some embodiments, the step of administering comprises: a) administering the IL-17 antagonist to the patient during an induction regimen; and b) thereafter administering the IL-17 antagonist to the patient during a maintenance regimen.

Disclosed herein are methods of treating rheumatoid arthritis (RA), comprising: a) administering a high risk RA patient three doses of about 10 mg/kg of an IL-17 antagonist, each of the three doses being delivered every other week; and b) thereafter administering about 75 mg-about 150 mg of the IL-17 antagonist to the patient every month, beginning one month from delivery of the third intravenous dose.

Disclosed herein are therapeutic regimens for treating rheumatoid arthritis (RA), comprising: a) selecting a patient having RA based on the following criteria; i. the patient is RF+, ACPA+, or both RF+ and ACPA+; and ii. the patient has a high level of CRP, a high ESR, or both a high level of CRP and a high ESR; and b) administering the patient three doses of about 10 mg/kg of an IL-17 antagonist, the first dose being delivered during week zero, the second dose being delivered during week two, and the third dose being delivered during week four; and c) thereafter administering the patient about 75 mg-about 150 mg of the IL-17 antagonist twice a month, monthly, every two months or every three months, beginning during week eight.

Disclosed herein are IL-17 antagonists for use in treating rheumatoid arthritis (RA), characterized in that the IL-17 antagonist is to be administered to a high risk RA patient. Disclosed herein are IL-17 antagonists for use in treating rheumatoid arthritis (RA), characterized in that the IL-17 antagonist is to be administered to a patient selected for treatment on the basis of the patient being a high risk RA patient.

Disclosed herein are IL-17 antagonists for use in treating a high risk RA patient. In some embodiments, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR. In some embodiments, a high level of CRP is ≥10 mg/L, as measured by hsCRP. In some embodiments, a high ESR is ≥28 mm/h.

Disclosed herein are IL-17 antagonists for use in treating rheumatoid arthritis (RA), characterized in that the IL-17 antagonist is to be administered to a patient, provided that the patient is selected for treatment on the basis of: a) being RF+, ACPA+, or both RF+ and ACPA+; and b) having a high level of CRP, a high ESR, or both a high level of CRP and a high ESR.

Disclosed herein are IL-17 antagonists for use in treating rheumatoid arthritis (RA), characterized in that the IL-17 antagonist is to be: a) administered to a high risk RA patient as three doses of about 10 mg/kg, each of the three doses being delivered every other week; and b) thereafter administered to the patient as a dose of about 75 mg-about 150 mg every month, beginning one month from delivery of the third intravenous dose.

Disclosed herein are IL-17 antagonists for use in treating rheumatoid arthritis (RA), characterized in that: a) a sample from a patient is assayed for: i. rheumatoid factor (RF), anti-citrullinated protein antibody (ACPA), or RF and ACPA; and ii. C-reactive protein (CRP), an erythrocyte sedimentation rate (ESR), or both CRP and an ESR; and b) the IL-17 antagonist is administered to the patient if the patient is RF+, ACPA+, or RF+ and ACPA+ and the patient has a high level of CRP, a high ESR, or a high level of CRP and a high ESR.

Disclosed herein are uses of an IL-17 antagonist for the manufacture of a medicament for treating RA, characterized in that the IL-17 antagonist is to be administered to high risk RA patient.

Disclosed herein are uses of an IL-17 antagonist for the manufacture of a medicament for treating RA, characterized in that the IL-17 antagonist is to be administered to high risk RA patient during an induction regimen followed by a maintenance regimen.

Disclosed herein are pharmaceutical composition for treating RA, comprising as an active ingredient an IL-17 antagonist, wherein the IL-17 antagonist is to be administered to a high risk RA patient.

Disclosed herein are pharmaceutical composition for treating RA, comprising as an active ingredient an IL-17 antagonist, wherein the IL-17 antagonist is to be administered to a high risk RA patient during an induction regimen followed by a maintenance regimen.

Disclosed herein are therapeutic regimens for treating RA, comprising: a) selecting a high risk RA patient; b) administering about 10 mg/kg of an IL-17 antagonist to the patient during weeks 0, 2 and 4; and c) thereafter administering about 75 mg-about 150 mg of the IL-17 antagonist to the patient monthly, beginning week 8.

Disclosed herein are methods of treating a RA patient or a high risk RA patient, comprising: a) administering an IL-17 binding molecule to a patient in need thereof during an induction regimen that provides a mean maximum plasma concentration ($C_{max}$) of the IL-17 binding molecule of about 360 μg/ml; and b) thereafter administering the IL-17 binding molecule to the patient during a maintenance regimen that provides: i) an average steady-state trough level of the IL-17 binding molecule between about 8 μg/ml-about 30 μg/ml; and/or ii) a mean AUC tau at steady state of about 331 mg*day/L-about 1323 mg*day/L.

Disclosed herein are IL-17 binding molecules for use in treating a RA patient or a high risk RA patient, characterized in that the IL-17 binding molecule: a) is to be administered to the patient during an induction regimen that provides a mean maximum plasma concentration ($C_{max}$) of the IL-17 binding molecule of about 360 μg/ml; and b) thereafter, is to be administered to the patient during a maintenance regimen that provides: i) an average steady-state trough level of the IL-17 binding molecule between about 8 μg/ml-about 30 μg/ml; and/or ii) a mean AUC tau at steady state of about 331 mg*day/L-about 1323 mg*day/L.

Disclosed herein are methods of treating a high risk RA patient, comprising: a) administering an IL-17 binding molecule to a patient in need thereof during an induction regimen that provides a mean maximum plasma concentration ($C_{max}$) of the IL-17 binding molecule of about 401 μg/ml; and b) thereafter administering the IL-17 binding molecule to the patient during a maintenance regimen that provides: i) an average steady-state trough level of the IL-17 binding molecule of about 9.4 μg/ml-about 31 μg/ml; and/or ii) a mean AUC tau at steady state of about 314 mg*day/L-about 1256 mg*day/L.

Disclosed herein are IL-17 binding molecule for use in treating psoriasis, characterized in that the IL-17 binding molecule: a) is to be administered to the patient during an induction regimen that provides a mean maximum plasma concentration ($C_{max}$) of the IL-17 binding molecule of about 401 μg/ml; and b) thereafter, is to be administered to the patient during a maintenance regimen that provides: i) an average steady-state trough level of the IL-17 binding molecule of about 9.4 μg/ml-about 31 μg/ml; and/or ii) a mean AUC tau at steady state of about 314 mg*day/L-about 1256 mg*day/L.

In some embodiments, the maintenance regimen provides an average steady-state trough level of the IL-17 binding molecule of about 9.4 μg/ml-about 17.3 μg/ml. In some embodiments, the maintenance provides an average steady-state trough level of the IL-17 binding molecule of about 9.4 μg/ml or about 17.3 μg/ml. In some embodiments, the induction regimen comprises intravenous administration of the IL-17 binding molecule every other week. In some embodiments, the maintenance regimen comprises monthly subcutaneous administration of the IL-17 binding molecule.

Disclosed herein are IL-17 antagonists in preparation of a medicament for the treatment of RA, provided that the patient is selected for the treatment on the basis of: a) being RF+, ACPA+, or both RF+ and ACPA+; and b) having a high level of CRP, a high ESR, or both a high level of CRP and a high ESR.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated to comprise containers, each container having a sufficient amount of the IL-17 antagonist to allow delivery of at least about 75 mg-about 150 mg IL-17 antagonist per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated to comprise containers, each container having a sufficient amount of the IL-17 antagonist to allow delivery of at least about 10 mg/kg per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated at a dosage to allow intravenous delivery of about 10 mg/kg per unit dose.

Disclosed herein are IL-17 antagonists for the manufacture of a medicament for the treatment of RA in a patient characterized as: a) being RF+, ACPA+, or both RF+ and ACPA+; and b) having a high level of CRP, a high ESR, or both a high level of CRP and a high ESR, wherein the medicament is formulated at a dosage to allow subcutaneous delivery of about 75 mg-about 150 mg IL-17 antagonist per unit dose.

Disclosed herein are in vitro test methods for selecting a patient for treatment of RA, comprising determining if: i. the patient is RF+, ACPA+, or both RF+ and ACPA+; and ii. the patient has a high level of CRP, a high ESR, or both a high level of CRP and a high ESR. In some embodiments of the disclosed in vitro test methods, the patient has an improved therapeutic response to the following regimen: a) administering the patient three doses of about 10 mg/kg of an IL-17 antagonist, the first dose being delivered during week zero, the second dose being delivered during week two, and the third dose being delivered during week four; and a) thereafter administering the patient about 75 mg-about 150 mg of the IL-17 antagonist twice a month, monthly, every two months or every three months, beginning during week eight.

In some embodiments of the disclosed methods, kits, uses, pharmaceutical compositions, and regimens, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR. In some embodiments, the high level of CRP is ≥10 mg/L, as measured by hsCRP. In some embodiments, the high ESR is ≥28 mm/h.

In some embodiments of the disclosed methods, kits, uses, pharmaceutical compositions, and regimens, the step of administering comprises intravenously administering three doses of about 10 mg/kg of the IL-17 antagonist to said patient, each of said doses being administered every other week. In some embodiments, the step of administering comprises subcutaneously administering doses of about 75 mg-about 150 mg of the IL-17 antagonist to said patient, each of said doses being administered monthly. In some embodiments, the step of administering comprises: a) administering the IL-17 antagonist to the high risk RA patient during an induction regimen; and b) thereafter administering the IL-17 antagonist to the patient during a maintenance regimen.

In some embodiments of the disclosed methods, kits, uses, pharmaceutical compositions, and regimens, the induction regimen comprises administering the patient three doses of about 10 mg/kg of the IL-17 antagonist. In some embodiments, the first dose of about 10 mg/kg is delivered during week zero, the second dose of about 10 mg/kg is delivered during week two, and the third dose of about 10 mg/kg is delivered during week four.

In some embodiments of the disclosed methods, kits, uses, pharmaceutical compositions, and regimens, the maintenance regimen comprises administering the patient about 75 mg-about 300 mg of the IL-17 antagonist. In some embodiments, the maintenance regimen comprises subcutaneously administering the patient about 75 mg-about 300 mg of the IL-17 antagonist twice a month, monthly, every two months or every three months. In some embodiments, the maintenance regimen comprises subcutaneously administering the patient about 75 mg-about 150 mg of the IL-17 antagonist twice a month, monthly, every two months or every three months, beginning during week eight. In some embodiments, the maintenance regimen comprises subcutaneously administering the patient about 75 mg or about 150 mg of the IL-17 antagonist monthly, beginning during week eight.

In some embodiments of the disclosed methods, kits, uses, pharmaceutical compositions, and regimens, prior to administering the IL-17 antagonist the patient had a previous RA treatment comprising administering at least one anti-rheumatic agent selected from the group consisting of an immunosuppressive agent, a disease-modifying anti-rheumatic drug (DMARD), a pain-control drug, a steroid, a non-steroidal anti-inflammatory drug (NSAID), a cytokine antagonist, a bone anabolic, a bone anti-resorptive, and combinations thereof. In some embodiments, the prior to administering the IL-17 antagonist the patient had an inadequate response to, had failure to or was intolerant to treatment with a DMARD, a TNF alpha antagonist, or methotrexate.

In some embodiments of the disclosed methods, kits, uses, pharmaceutical compositions, and regimens, the patient is additionally administered a therapeutically effective amount of at least one anti-rheumatic agent selected from the group consisting of an immunosuppressive agent, a DMARD, a pain-control drug, a steroid, a NSAID, a cytokine antagonist, a bone anabolic, a bone anti-resorptive, and combinations thereof.

In some embodiments of the disclosed methods, kits, uses, pharmaceutical compositions, and regimens, the IL-17 antagonist is administered as three doses of about 10 mg/kg, each of said doses being administered every other week. In some embodiments, the IL-17 antagonist is administered as doses of about 75 mg-about 300 mg, each of said doses being administered monthly.

In some embodiments of the disclosed methods, kits, uses, pharmaceutical compositions, and regimens, the IL-17 antagonist is to be administered to the patient during an induction regimen and thereafter administered to the patient during a maintenance regimen. In some embodiments, the induction regimen comprises administering the patient three doses of about 10 mg/kg of the IL-17 antagonist. In some embodiments, the first dose of about 10 mg/kg is delivered during week zero, the second dose of about 10 mg/kg is delivered during week two, and the third dose of about 10 mg/kg is delivered during week four.

In some embodiments of the disclosed methods, kits, uses, pharmaceutical compositions, and regimens, the maintenance regimen comprises administering the patient about 75 mg-about 300 mg of the IL-17 antagonist. In some embodiments, the maintenance regimen comprises subcutaneously administering the patient about 75 mg-about 300 mg of the IL-17 antagonist twice a month, monthly, every two months or every three months. In some embodiments, the maintenance regimen comprises subcutaneously administering the patient about 75 mg-about 150 mg of the IL-17 antagonist twice a month, monthly, every two months or every three months, beginning during week eight. In some embodiments, the maintenance regimen comprises subcutaneously administering the patient about 75 mg or about 150 mg of the IL-17 antagonist monthly, beginning during week eight.

In some embodiments of the disclosed methods, kits, uses, pharmaceutical compositions, and regimens, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR.

In some embodiments of the disclosed methods, kits, uses, pharmaceutical compositions, and regimens, the induction regimen maintains the trough level of the IL-17 binding molecule above 80 μg/ml for a 10 week period. In some embodiments, the maintenance regimen provides an average steady-state trough level of the IL-17 binding molecule of about 8 μg/ml-about 17 μg/ml. In some embodiments, the maintenance provides an average steady-state trough level of the IL-17 binding molecule of about 8 μg/ml or about 17 μg/ml.

In some embodiments of the disclosed methods, kits, uses, pharmaceutical compositions, and regimens, the IL-17 antagonist is an IL-17 binding molecule or an IL-17 receptor binding molecule. In some embodiments, the IL-17 binding molecule or an IL-17 receptor binding molecule is an IL-17 binding molecule (e.g., IL-17 antibody) selected from the group consisting of: a) secukinumab; b) an IL-17 antibody that binds to an epitope of IL-17 comprising Leu74, Tyr85, His86, Met87, Asn88, Val124, Thr125, Pro126, Ile127, Val128, His129; c) an IL-17 antibody that binds to an epitope of IL-17 comprising Tyr43, Tyr44, Arg46, Ala79, Asp80; d) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain; e) an IL-17 antibody that binds to an epitope of an IL-17 homodimer having two mature IL-17 protein chains, said epitope comprising Leu74, Tyr85, His86, Met87, Asn88, Val124, Thr125, Pro126, Ile127, Val128, His129 on one chain and Tyr43, Tyr44, Arg46, Ala79, Asp80 on the other chain, wherein the IL-17 binding molecule has a $K_D$ of about 100-200 pM, and wherein the IL-17 binding molecule has an in vivo half-life of about 4 weeks; and f) an IL-17 antibody that comprises an antibody selected from the group consisting of: i) an immunoglobulin heavy chain variable domain ($V_H$) comprising the amino acid sequence set forth as SEQ ID NO:8; ii) an immunoglobulin light chain variable domain ($V_L$) comprising the amino acid sequence set forth as SEQ ID NO:10; iii) an immunoglobulin $V_H$ domain comprising the amino acid sequence set forth as SEQ ID NO:8 and an immunoglobulin $V_L$ domain comprising the amino acid sequence set forth as SEQ ID NO:10; iv) an immunoglobulin $V_H$ domain comprising the hypervariable regions set forth as SEQ ID NO:1, SEQ ID NO:2, and SEQ ID NO:3; v) an immunoglobulin $V_L$ domain comprising the hypervariable regions set forth as SEQ ID NO:4, SEQ ID NO:5 and SEQ ID NO:6; vi) an immunoglobulin $V_H$ domain comprising the hypervariable regions set forth as SEQ ID NO:11, SEQ ID NO:12 and SEQ ID NO:13; vii) an immunoglobulin $V_H$ domain comprising the hypervariable regions set forth as SEQ ID NO:1, SEQ ID NO:2, and SEQ ID NO:3 and an immunoglobulin $V_L$ domain comprising the hypervariable regions set forth as SEQ ID NO:4, SEQ ID NO:5 and SEQ ID NO:6; and viii) an immunoglobulin $V_H$ domain comprising the hypervariable regions set forth as SEQ ID NO: 11, SEQ ID NO:12 and SEQ ID NO:13 and an immunoglobulin $V_L$ domain comprising the hypervariable regions set forth as SEQ ID NO:4, SEQ ID NO:5 and SEQ ID NO:6.

In preferred embodiments of the disclosed methods, kits, uses, pharmaceutical compositions, and regimens, the IL-17 binding molecule is a human antibody. In even more preferred embodiments of the disclosed methods, kits, uses, pharmaceutical compositions, and regimens, the IL-17 binding molecule is secukinumab.

As used herein, the phrase "container having a sufficient amount of the IL-17 antagonist to allow delivery of [a designated dose]" is used to mean that a given container (e.g., vial, pen, syringe) has disposed therein a volume of an IL-17 antagonist (e.g., as part of a pharmaceutical composition) that can be used to provide a desired dose. As an example, if a desired dose is 75 mg, then a clinician may use 2 ml from a container that contains an IL-17 antibody formulation with a concentration of 37.5 mg/ml, 1 ml from a container that contains an IL-17 antibody formulation with a concentration of 75 mg/ml, 0.5 ml from a container contains an IL-17 antibody formulation with a concentration of 150 mg/ml, etc. In each such case, these containers have a sufficient amount of the IL-17 antagonist to allow delivery of the desired 75 mg dose.

As used herein, the phrase "formulated at a dosage to allow [route of administration] delivery of [a designated dose]" is used to mean that a given pharmaceutical composition can be used to provide a desired dose of an IL-17 antagonist, e.g., an IL-17 antibody, e.g., secukinumab, via a designated route of administration (e.g., s.c. or i.v.). As an example, if a desired subcutaneous dose is 75 mg, then a clinician may use 2 ml of an IL-17 antibody formulation having a concentration of 37.5 mg/ml, 1 ml of an IL-17 antibody formulation having a concentration of 75 mg/ml, 0.5 ml of an IL-17 antibody formulation having a concentration of 150 mg/ml, etc. In each such case, these IL-17 antibody formulations are at a concentration high enough to allow subcutaneous delivery of the IL-17 antibody. Subcutaneous delivery typically requires delivery of volumes of less than about 2 ml, preferably a volume of about 1 ml or less.

In some embodiments, the induction regimen comprises administration of 1, 2, 3, 4, 5, 6, or more i.v. doses of the IL-17 antagonist (e.g., secukinumab), e.g., secukinumab, preferably one, two or three (most preferably three) doses of secukinumab delivered every week, every other week, every three weeks or every four weeks (monthly). In some embodiments, the induction regimen comprises administration of 10 mg/kg i.v. of the IL-17 antagonist (e.g., secukinumab), e.g., secukinumab.

In some embodiments, induction doses of the IL-17 antagonist (e.g., secukinumab) may be administered as three i.v. infusions (e.g., 10 mg/kg) every other week, i.e., during week zero (e.g., day 1), during week two (e.g., about day 15), and during week four (e.g., about day 29). In some embodiments, induction doses may be administered as three i.v. infusions (e.g., 10 mg/kg) every three weeks, i.e., during week zero (e.g., about day 1), during week three (e.g., about day 22), and during week six (e.g., about day 43). In some embodiments, induction doses may be administered as three i.v. infusions (e.g., 10 mg/kg) every four weeks (monthly), i.e., during week zero (e.g., about day 1), during week four (e.g., about day 29), and during week eight (e.g., about day 57).

In some embodiments, induction doses of the IL-17 antagonist (e.g., secukinumab) may be administered as two i.v. infusions (e.g., 10 mg/kg) every other week, i.e., during week zero (about day 1), and during week two (e.g., about day 15). In some embodiments, induction doses may be administered as two i.v. infusions (e.g., 10 mg/kg) every three weeks, i.e., during week zero (e.g., about day 1) and during week three (e.g., about day 22). In some embodiments, induction doses may be administered as two i.v. infusions (e.g., 10 mg/kg) every four weeks (monthly), i.e., during week zero (e.g., about day 1) and during week four (e.g., about day 29).

In some embodiments, induction doses of the IL-17 antagonist (e.g., secukinumab) may be administered as a single high dose infusion, e.g., 30 mg/kg.

In further embodiments, the induction regimen comprises administration of 1, 2, 3, 4, 5, 6, or more daily or weekly s.c. doses of the IL-17 antagonist (e.g., secukinumab), preferably three to five (e.g., four) weekly doses of secukinumab. In some embodiments, the induction dosage that may be administered daily or weekly is about 75 mg-about 300 mg of the IL-17 antagonist (e.g., secukinumab) delivered s.c. (e.g, about 75 mg-about 150 mg, e.g., about 75 mg or about 150 mg).

In some embodiments, the induction regimen comprises administration of daily s.c. doses of the IL-17 antagonist (e.g., secukinumab), e.g., daily s.c. doses of secukinumab (e.g., about 75 mg-about 300 mg, e.g, about 75 mg-about 150 mg, e.g., about 75 mg or about 150 mg), delivered on days 1-7. In some embodiments, the induction regimen comprises administration of weekly s.c. doses of the IL-17 antagonist (e.g., secukinumab), e.g., weekly s.c. doses of secukinumab, delivered during week zero, one, two, and three.

In other embodiments, the dose(s) secukinumab administered to a subject may be higher and more frequent (i.e., weekly for the first month of treatment) during an induction regimen, and then the patient may be maintained at a lower dose.

In some embodiments, the maintenance regimen comprises subcutaneously administering the patient about 75 mg or about 150 mg of the IL-17 binding molecule if the patient weighs less than 90 kg. In some embodiments, the maintenance regimen comprises subcutaneously administering the patient about 150 mg or about 300 mg of the IL-17 binding molecule if the patient weighs more than or equal to 90 kg.

For a maintenance regimen, a dose of the IL-17 antagonist (e.g., secukinumab) may be provided twice a month (i.e., every two weeks, bimonthly or every other week, i.e., about every 14 days), every month (i.e., every 4 weeks, i.e., about every 28 days), every two months (i.e., every other month or every 8 weeks, i.e., about every 56 days), or every three months (i.e., every 12 weeks, i.e., about every 84 days). As used herein, the date of the first dose of a maintenance regimen will be measured from the final dose of the induction regimen. Thus, as an example, if the final dose of the induction regimen is provided during week four, then a first dose as part of a bimonthly maintenance regimen may be delivered during week six (about day 43), a first dose as part of a monthly maintenance regimen may be delivered during week eight (about day 57), a first dose as part of an every two month maintenance regimen may be delivered during week twelve (about 85 days), a first dose as part of an every three month maintenance regimen may be delivered during week sixteen (about 113 days), etc. In some embodiments, the first dose of the maintenance regimen is delivered every month (monthly, about every four weeks), beginning one month (i.e., about four weeks) from delivery of a final induction (e.g., s.c. or i.v. induction) dose. In some embodiments, the first dose of the maintenance regimen is delivered every month (monthly, about every four weeks), beginning one month (i.e., about four weeks) from delivery of a third i.v. induction dose.

In some embodiments, the maintenance regimen comprises administration of the IL-17 antagonist (e.g., secukinumab), e.g., about 75 mg-about 300 mg (e.g, about 75 mg-about 150 mg, e.g., about 75 mg or about 150 mg) delivered bimonthly, monthly, every two months or every three months. In some embodiments, the IL-17 antagonist (e.g., secukinumab) is delivered s.c. during the maintenance regimen. In a preferred embodiment, a maintenance dose is delivered monthly. In some embodiments, a first maintenance dose is delivered during week six (e.g., about day 43), seven (e.g., about day 50), eight (e.g., about day 57), nine (e.g., about day 64), ten (e.g., about day 71), eleven (e.g., about day 78), twelve (e.g., about day 85), or thirteen (e.g., about day 92) of the treatment regimen, and then monthly (e.g., about every 4 weeks or about every 28 days) thereafter. In some embodiments, the maintenance regimen comprises subcutaneously administering the patient about 75 mg-about 300 mg (e.g, about 75 mg-about 150 mg, e.g., about 75 mg or about 150 mg) of the IL-17 antagonist (e.g., secukinumab) twice a month, monthly, every two months or every three months, beginning during week four, five, six, seven, eight, nine, ten, eleven, or twelve, preferably during week eight.

Preferred treatment regimens for treating RA patients (e.g., high risk RA patients) and patients having other inflammatory arthritis, e.g., spondyloarthropathy, ankylosing spondylitis (AS), and psoriatic arthritis (PsA), are provided in Table 5:

TABLE 5

Preferred dosing regimens for treating RA patients (e.g., high risk RA patients) and patients having other inflammatory arthritis, e.g., spondyloarthropathy, ankylosing spondylitis, and psoriatic arthritis.

| | |
|---|---|
| i.v. induction regimen<br>(3 × 10 every other week)<br>first dose = during week 0<br>second dose = during week 2<br>third dose = during week 4 | maintenance regimen (150 or 300 mg)<br>first monthly dose = during week 8<br>every month (about 4 weeks) thereafter. |
| i.v. induction regimen<br>(3 × 10 every three weeks)<br>first dose = during week 0<br>second dose = during week 3<br>third dose = during week 6 | maintenance regimen<br>first monthly dose = during week 10<br>very month (about 4 weeks) thereafter |
| i.v. induction regimen (3 × 10 every month)<br>first dose = during week 0<br>second dose = during week 4<br>third dose = during week 8 | maintenance regimen<br>first monthly dose = during week 12<br>every month (about 4 weeks) thereafter |
| i.v. induction regimen<br>(2 × 10 every other week)<br>first dose = during week 0<br>Second dose = during week 2 | maintenance regimen<br>first monthly dose = during week 6<br>every month (about 4 weeks) thereafter |
| i.v. induction regimen<br>(2 × 10 every three week)<br>first dose = during week 0<br>second dose = during week 3 | maintenance regimen<br>first monthly dose = during week 7<br>every month (about 4 weeks) thereafter |
| i.v. induction regimen (2 × 10 every month)<br>first dose = during week 0 | maintenance regimen<br>first monthly dose = during week 8 |

TABLE 5-continued

Preferred dosing regimens for treating RA patients (e.g., high risk RA patients) and patients having other inflammatory arthritis, e.g., spondyloarthropathy, ankylosing spondylitis, and psoriatic arthritis.

| | |
|---|---|
| second dose = during week | every month (about 4 weeks) thereafter. |
| S.C. induction regimen (150 or 300 mg weekly for 4 doses)<br>first weekly dose = during week 0<br>second weekly dose = during week 1<br>third weekly dose = during week 2<br>fourth weekly dose = during week 3 | maintenance regimen<br>first monthly dose = during week 7<br>every month (about 4 weeks) thereafter |
| S.C. induction regimen (150 or 300 mg daily)<br>dose 1-7 = day 1-7 | maintenance regimen<br>first monthly dose = during week 4 or 5<br>every month (about 4 weeks) thereafter |
| S.C. induction regimen (150 or 300 mg weekly for 5 doses)<br>first weekly dose = during week 0<br>second weekly dose = during week 1<br>third weekly dose = during week 2<br>fourth weekly dose = during week 3<br>fifth weekly dose = during week 4 | maintenance regimen<br>first monthly dose = during week 8<br>every month (about 4 weeks) thereafter |

It will be understood that a dose need not be provided at an exact time point, e.g., a dose due on day 29 could be provided, e.g., on day 24 to day 34.

In some embodiments, the dosage of the IL-17 antagonist (e.g., secukinumab) used in the disclosed induction and/or maintenance regimens (as the case may be) is based on the patient's weight (e.g., whether a patient is under or over 75 kg, 80 kg, 85 kg, 90 kg, 95 kg, 100 kg, 105 kg, etc. can be used to define a dosage of the IL-17 antagonist, e.g., secukinumab, for delivery to the patient). In one embodiment, the patient is administered about 75 mg or about 150 mg (e.g., delivered s.c.). if the patient weighs less than or equal to about 80 kg. In one embodiment, the patient is administered about 75 mg or about 150 mg (e.g., delivered s.c.). if the patient weighs less than or equal to about 90 kg. In one embodiment, the patient is administered about 75 mg or about 150 mg (e.g., delivered s.c.) if the patient weighs less than or equal to about 100 kg. In another embodiment, the patient is administered about 150 mg or about 300 mg (e.g., delivered s.c.) if the patient weighs more than about 80 kg. In another embodiment, the patient is administered about 150 mg or about 300 mg (e.g., delivered s.c.) if the patient weighs more than about 90 kg. In another embodiment, the patient is administered about 150 mg or about 300 mg (e.g., delivered s.c.) if the patient weighs more than about 100 kg.

It will be understood that dose escalation may be required (e.g., during the induction and/or maintenance phase) for certain patients, e.g., patients that display inadequate response to treatment with the IL-17 antagonist (e.g., secukinumab). Thus, s.c. doses of the IL-17 antagonist (e.g., secukinumab) may be greater than about 75 mg to about 300 mg s.c., e.g., about 80 mg, about 100 mg, about 125 mg, about 175 mg, about 200 mg, about 250 mg, about 350 mg, about 400 mg, etc.; similarly, i.v. doses may be greater than about 10 mg/kg, e.g., about 11 mg/kg, 12 mg/kg, 15 mg/kg, 20 mg/kg, 25 mg/kg, 30 mg/kg, 35 mg/kg, etc. It will also be understood that dose reduction may also be required (e.g., during the induction and/or maintenance phase) for certain patients, e.g., patients that display adverse events or an adverse response to treatment with the IL-17 antagonist (e.g., secukinumab). Thus, doses of the IL-17 antagonist (e.g., secukinumab) may be less than about 75 mg to about 300 mg s.c., e.g., about 25 mg, about 50 mg, about 80 mg, about 100 mg, about 125 mg, about 175 mg, about 200 mg, 250 mg, etc.; similarly, i.v. doses may be less than about 10 mg/kg, e.g., about 9 mg/kg, 8 mg/kg, 5 mg/kg, 4 mg/kg, 3 mg/kg, 2 mg/kg, 1 mg/kg, etc.

In some embodiments of the above methods, uses, pharmaceutical compositions, kits and treatment regimens, a CRP level of ≥about 3 mg/L (e.g., 3 mg/L), ≥about 5 mg/L (e.g., 5 mg/L), ≥about 10 mg/L (e.g., 10 mg/L), ≥about 15 mg/L (e.g., 15 mg/L) is considered a high level of CRP. In some embodiments, a CRP level of ≥200 nmol/L or ≥240 nmol/L is considered a high CRP level. In a preferred embodiment, a CRP level of greater than or equal (≥) to about 10 mg/L (e.g., 10 mg/L), e.g., as measured by a high sensitivity CRP assay, is considered a high CRP level. In some embodiments, a high level of CRP is >about 10 mg/L, >about 20 mg/L or >about 30 mg/L.

In some embodiments of the above methods, uses, pharmaceutical compositions, kits and treatment regimens, "high ESR" may be determined based on the following rule: normal maximum ESR (mm/h)≤(Age (years)+10 (if female))/2. As a result, a "high ESR">(Age (years)+10 (if female))/2. In some embodiments, a "high ESR" may be determined based on the following rule: normal maximum ESR (mm/h)≤(Age (years)+5 (if female))/2. As a result, a "high ESR">(Age (years)+5 (if female))/2. In some embodiments, an ESR of ≥20 mm/h is a high ESR for females. In some embodiments, an ESR of ≥15 mm/h is a high ESR for males. In a preferred embodiment, an ESR of greater than or equal (≥) to 28 mm/h is a high ESR.

In some embodiments of the above methods, uses, pharmaceutical compositions, kits and treatment regimens, a patient is RF+ if the patient's RF value is greater than 20 IU/ml or greater than 30 IU/ml. In some embodiments, a patient is RF+ if the patient's RF value is greater than 40 units/ml or greater than 60 units/ml, as measured by a nephelometry test. In some embodiments, a patient is RF+ if the patient's RF titer is greater than 1:20 or greater than 1:80, as measured by a dilution test. In a preferred embodiment, a patient is RF+ if the patient's RF value is greater than or equal (≥) to 12 kU/L (kiloUnits/Liter), e.g., as measured by nephelometry.

In some embodiments of the above methods, uses, pharmaceutical compositions, kits and treatment regimens, a patient is ACPA+ if the patient's ACPA value is greater than 1 U/ml, greater than 3 U/ml, or greater than 5 U/ml, e.g., as determined by an anti-CCP ELISA test. In a preferred embodiment, a patient is ACPA+ if the patient's ACPA value is greater than 20 units/ml (20 U).

Disclosed herein are also methods of treating rheumatoid arthritis (RA), comprising: a) administering (e.g., subcutaneously administering) a high risk RA patient four or five doses of about 75 mg-about 300 mg (e.g, about 75 mg-about 150 mg, e.g., about 75 mg or about 150 mg) of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof), each of the four or five doses being delivered weekly; and b) thereafter administering about 75 mg-about 300 mg (e.g, about 75 mg-about 150 mg, e.g., about 75 mg or about 150 mg) of the IL-17 antagonist (e.g., secukinumab) to the patient twice a month, every month, every two months or every three months.

Disclosed herein are also therapeutic regimens for treating RA, comprising: a) selecting a patient having rheumatoid arthritis based on the following criteria; i.) the patient is RF+, ACPA+, or both RF+ and ACPA+; and ii.) the patient has a high level of CRP, a high ESR, or both a high level of CRP and a high ESR; and b) administering (e.g., subcutaneously administering) about 75 mg-about 300 mg (e.g, about 75 mg-about 150 mg, e.g., about 75 mg or about 150 mg) of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to the patient weekly for four or five weeks; and c) thereafter administering (e.g., subcutaneously administering) about 75 mg-about 300 mg (e.g, about 75 mg-about 150 mg, e.g., about 75 mg or about 150 mg) of the IL-17 binding molecule to the patient twice a month, every month, every two months or every three months.

Disclosed herein are methods of treating rheumatoid arthritis (RA), comprising administering a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to a RA patient displaying elevated baseline CRP levels (e.g., greater than about 10 mg/L, greater than about 20 mg/L, greater than about 30 mg/L).

Disclosed herein are also therapeutic regimens for treating RA, comprising: a) selecting a patient having rheumatoid arthritis based on the following criteria: i.) the patient has elevated baseline CRP levels (e.g., greater than about 10 mg/L, greater than about 20 mg/L, greater than about 30 mg/L); and b) either i) administering (e.g., subcutaneously administering) about 75 mg-about 300 mg (e.g, about 75 mg-about 150 mg, e.g., about 75 mg or about 150 mg) of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to the patient weekly for four or five doses or ii) administering (e.g., i.v. administering) about 10 mg/kg of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) to the patient every other week for three doses; and c) thereafter administering (e.g., subcutaneously administering) about 75 mg-about 300 mg (e.g, about 75 mg-about 150 mg, e.g., about 75 mg or about 150 mg) of the IL-17 antagonist (e.g., secukinumab) to the patient twice a month, every month, every two months or every three months, preferably monthly.

Herein are also provided methods of treating an inflammatory arthritis, comprising an induction regimen, e.g., administering (e.g., intravenously administering) two or three induction doses of about 10 mg/kg of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) (preferably three induction doses) to a patient having an arthritis, wherein the arthritis is selected from the group consisting of rheumatoid arthritis (RA), spondyloarthropathy, ankylosing spondylitis (AS), and psoriatic arthritis (PsA). In some embodiments, the first dose is delivered during week zero, the second dose is delivered during week two, and the third dose is delivered during week four. In some embodiments, the first dose is delivered during week zero, the second dose is delivered during week three, and the third dose is delivered during week six. In some embodiments, the method further comprises a maintenance regimen, e.g., administering (e.g., subcutaneously administering) about 75 mg-about 300 mg (e.g, about 75 mg-about 150 mg, e.g., about 75 mg or about 150 mg) of the IL-17 antagonist (e.g., secukinumab) to the patient, wherein the IL-17 binding molecule is administered to the patient twice a month, monthly, every two months or every three months. In some embodiments the patient is a high risk RA patient, e.g., seropositive for rheumatoid factor (RF+), anti-cyclic citrullinated protein antibody (ACPA+), or both RF+ and ACPA+; and has a high level of C-reactive protein (CRP), a high erythrocyte sedimentation rate (ESR), or both a high level of CRP and a high ESR). In some embodiments, the high level of CRP is ≥10 mg/dL. In some embodiments, the high ESR is ≥28 mm/h. In further embodiments, the inflammatory arthritis is selected from rheumatoid arthritis (RA), spondyloarthropathy, ankylosing spondylitis, and psoriatic arthritis. In some embodiment, the patient has RA. In further embodiments, the RA patient is a high risk RA patient. In further embodiments, the high risk RA patient: a) is seropositive for rheumatoid factor (RF+), anti-citrullinated protein antibody (ACPA+), or both RF+ and ACPA+; and b) has a high level of C-reactive protein (CRP), a high erythrocyte sedimentation rate (ESR), or both a high level of CRP and a high ESR.

In some embodiments, the IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is used in combination with methotrexate for the treatment of adult patients with moderately- to severely-active rheumatoid arthritis who have had an inadequate response to one or more TNF antagonist therapies. In some embodiments, the IL-17 antagonist (e.g., secukinumab) is used alone or in combination with methotrexate or other disease-modifying anti-rheumatic drugs (DMARDs) to reduce signs and symptoms (e.g., swelling, restricted movement), inducing major clinical response, inhibit the progression of structural damage, and improve physical function in adult patients with moderately to severely active disease. In some embodiments, the IL-17 antagonist (e.g., secukinumab) is used alone or in combination with methotrexate to reduce signs and symptoms, induce major clinical response, inhibit the progression of structural damage, and improve physical function in patients with moderately to severely active rheumatoid arthritis (RA). In some embodiments, the IL-17 antagonist (e.g., secukinumab) is used in combination with methotrexate, for reducing signs and symptoms, inhibiting the progression of structural damage, and improving physical function in patients with moderately to severely active rheumatoid arthritis. In some embodiments, the IL-17 antagonist (e.g., secukinumab) is used for the treatment of adults with moderately to severely active rheumatoid arthritis (RA). In some embodiments, the IL-17 antagonist (e.g., secukinumab) is used for treating moderately to severely active Rheumatoid Arthritis (RA) in adults, in combination with methotrexate. In some embodiments, the IL-17 antagonist (e.g., secukinumab) is used for reduction in signs and symptoms and slowing the progression of structural damage in moderately to severely active rheumatoid arthritis, in patients who have failed 1 or more disease modifying antirheumatic drugs (DMARDs). In some embodiments, the IL-17 antagonist (e.g., secukinumab) is used as a monotherapy or concomitantly with disease-modifying antirheumatic drugs (DMARDs) for reducing signs and symptoms, inducing major clinical response, inhibiting the progression of structural damage, and improving physical function in adult patients with moderately to severely active rheumatoid arthritis. In some embodiments, the IL-17 antagonist (e.g., secukinumab) is used alone or in combination with methotrexate or other DMARDs to treat adult patients with moderately to severely active rheumatoid arthritis who have had an inadequate response to one or more TNF antagonist therapies.

Combination Therapies for the Treatment of Arthritis

In practicing the methods of treatment or uses of the present disclosure, a therapeutically effective amount of an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) is administered to a subject, e.g., a mammal (e.g., a human). An IL-17 binding antagonist (e.g., secukinumab) may be administered in accordance with the method of the disclosure either alone or in combination with other agents and therapies for treating RA, e.g., in combination with at least one anti-rheumatic agent, such as an immunosuppressive agent, a disease-modifying anti-rheumatic drug (DMARD), a pain-control drug, a steroid, a non-steroidal anti-inflammatory drug (NSAID), a cytokine antagonist, a bone anabolic, a bone anti-resorptive, and combinations thereof (e.g., dual and triple therapies). When coadministered with one or more additional agents, an IL-17 antagonist (e.g., secukinumab) may be administered either simultaneously with the other agent, or sequentially. If administered sequentially, the attending physician will decide on the appropriate sequence of administering the IL-17 antagonist (e.g., secukinumab) in combination with other agents.

Non-steroidal anti inflammatory drugs and pain control agents useful in combination with the IL-17 antagonist (e.g., secukinumab) for the treatment of RA patients, e.g., high risk RA patients, include, propionic acid derivative, acetic acid derivative, enolic acid derivatives, fenamic acid derivatives, Cox inhibitors, e.g., lumiracoxib, ibuprophen, fenoprofen, ketoprofen, flurbiprofen, oxaprozin, indomethacin, sulindac, etodolac, ketorolac, nabumetone, aspirin, naproxen, valdecoxib, etoricoxib, MK0966; rofecoxib, acetominophen, Celecoxib, Diclofenac, tramadol, piroxicam, meloxicam, tenoxicam, droxicam, lornoxicam, isoxicam, mefanamic acid, meclofenamic acid, flufenamic acid, tolfenamic, valdecoxib, parecoxib, etodolac, indomethacin, aspirin, ibuprophen, firocoxib.

Disease-modifying antirheumatic drugs (DMARDs) useful in combination with the IL-17 antagonist (e.g., secukinumab) for the treatment of RA patients, e.g., high risk RA patients, include, methotrexate (MTX), antimalarial drugs (e.g., hydroxychloroquine and chloroquine), sulfasalazine, Leflunomide, azathioprine, cyclosporin, gold salts, minocycline, cyclophosphamide, D-penicillamine, minocycline, auranofin, tacrolimus, myocrisin, chlorambucil.

Biologic agents useful in combination with the IL-17 antagonist (e.g., secukinumab) for the treatment of RA patients, e.g., high risk RA patients, include, ADALIMUMAB (Humira®), ETANERCEPT (Enbrel®), INFLIXIMAB (Remicade®; TA-650), CERTOLIZUMAB PEGOL (Cimzia®; CDP870), GOLIMUMAB (Simponi®; CNTO148), ANAKINRA (Kineret®), RITUXIMAB (Rituxan®; MabThera®), ABATACEPT (Orencia®), TOCILIZUMAB (RoActemra/Actemra®).

Other biological agents useful in combination with the IL-17 antagonist (e.g., secukinumab) for the treatment of RA patients, e.g., high risk RA patients, include, e.g., integrin antagonist (TYSABRI® (natalizumab)), IL-1 antagonists (ACZ885 (Ilaris)), Anakinra (Kineret®)), CD4 antagonists, IL-17 antagonists (LY2439821, RG4934, AMG827, SCH900117, R05310074, MEDI-571, CAT-2200), IL-23 antagonists, IL-20 antagonists, IL-6 antagonists, TNF alpha antagonists (e.g., TNF alpha antagonists or TNF alpha receptor antagonists, e.g., pegsunercept, etc.), BLyS antagonists (e.g., Atacicept, Benlysta®/LymphoStat-B® (belimumab)), P38 Inhibitors, CD20 antagonists (Ocrelizumab, Ofatumumab (Arzerra®)), Interferon gamma antagonists (Fontolizumab).

Steroids (e.g., glucocorticoids) useful in combination with the IL-17 antagonist (e.g., secukinumab) for the treatment of RA patients, e.g., high risk RA patients, include, Prednisolone, Prednisone, dexamethasone, cortisol, cortisone, hydrocortisone, methylprednisolone, betamethasone, triamcinolone, beclometasome, fludrocottisone, deoxycorticosterone, aldosterone Other agents useful in combination with the IL-17 antagonist (e.g., secukinumab) for the treatment of RA patients, e.g., high risk RA patients, include, SB-681323, Rob 803, AZD5672, AD 452, SMP 114, HZT-501, CP-195,543, Doxycycline, vancomycin, CRx-102, AMG108, pioglitazone, SBI-087, SCIO-469, Cura-100, Oncoxin+Viusid, TwHF, PF-04171327, AZD5672, Methoxsalen, ARRY-438162, Vitamin D—ergocalciferol, Milnacipran, Paclitaxel, GW406381, rosiglitazone, SC12267 (4SC-101); LY2439821, BTT-1023, ERB-041, ERB-041, KB003, CF101, ADL5859, MP-435, ILV-094, GSK706769, GW856553, ASK8007, MOR103, HE3286, CP-690,550 (tasocitinib), REGN88 (SAR153191), TRU-015, BMS-582949, SBI-087, LY2127399, E-551S-551, H-551, GSK3152314A, RWJ-445380, Tacrolimus (Prograf®), RAD001, rapamune, rapamycin, fostamatinib, Fentanyl, XOMA 052, CNTO 136, JNJ 38518168, Imatinib, ATN-103, ISIS 104838, folic acid, folate, TNFa kinoid, MM-093, type II collagen, VX-509, AMG 827 70, masitinib (AB1010), LY2127399, cyclosporine, SB-681323, MK0663, NNC 0151-0000-0000, ATN-103, CCX 354-C, CAM3001, LX3305, Cetrorelix, MDX-1342, TMI-005, MK0873, CDP870, Tranilast, CF101, mycophenolic acid (and esters thereof), VX-702, GLPG0259, SB-681323, BG9924, ART621, LX3305, T-614, Fostamatinib disodium (R935788), CCI-779, ARRY-371797, CDP6038, AMG719, BMS-582949, GW856553, rosiglitazone, CH-4051, CE-224,535, GSK1827771, GW274150, BG9924, PLX3397, TAK-783, INCB028050, LY2127399, LY3009104, R788, Curcumin (Longvida™) Rosuvastatin, PRO283698, AMG 714, MTRX1011A, Maraviroc, MEDI-522, MK0663, STA 5326 mesylate, CE-224,535, AMG108, BG00012, ramipril, VX-702, CRx-102, LY2189102, SBI-087, SB-681323, CDP870, Milnacipran, PD 0360324, PH-797804, AK106-001616, PG-760564, PLA-695, MK0812, ALD518, Cobiprostone, somatropin, tgAAC94 gene therapy vector, MK0359, GW856553, esomeprazole, everolimus, trastuzumab, bone anabolics and bone anti-resorptives (e.g., PTH, bisphosphonates (e.g., zoledronic acid), JAK1 and JAK2 inhibitors, pan JAK inhibitors, e.g., tetracyclic pyridone 6 (P6), 325, PF-956980, sclerostin antagonists (e.g., disclosed in WO09047356, WO2000/32773, WO2006102070, US20080227138, US20100028335, US 20030229041, WO2005003158, WO2009039175 WO2009079471, WO03106657, WO2006119062, WO08115732, WO2005/014650, WO2005/003158, WO2006/119107, WO2008/061013, WO2008/133722, WO2008/115732, U.S. Pat. Nos. 7,592,429, 7,879,322, 7,744,874, the contents of which are incorporated by reference herein in their entirety [preferred anti-sclerostin antibodies and antigen binding fragments thereof for use in the disclosed methods, pharmaceutical compositions, kits and uses are found in WO09047356 (equivalent to U.S. Pat. No. 7,879,322), WO06119107 (equivalent to U.S. Pat. Nos. 7,872,106 and 7,592,429) and WO08115732 (equivalent to U.S. Pat. No. 7,744,874]), denosumab, IL-6 antagonists, CD20 antagonists, CTLA4 antagonists, IL-17 antagonists, IL-8 antagonists, IL-21 antagonists, IL-22 antagonist, integrin antagonists (Tysarbri® (natalizumab)), sclerostin antagonists, VGEF antagonists, CXCL antagonists, MMP antagonists, defensin antagonists, IL-1 antagonists (including IL-1 beta antagonists), and IL-23 antagonists (e.g., receptor decoys, antagonistic antibodies, etc.).

In some embodiments, the IL-17 antagonist (e.g., secukinumab) is administered in combination with at least one anti-rheumatic agent selected from the group consisting of an immunosuppressive agent, a DMARD, a pain-control drug, a steroid, a NSAID, a cytokine antagonist, a bone anabolic, a bone anti-resorptive, and combinations thereof. In some embodiments, the IL-17 antagonist (e.g., secukinumab) is administered in combination with a TNF antagonist, a DMARD (e.g., MTX, e.g., weekly doses of 7.5-30 mg)), a steroid, or combinations thereof.

A skilled artisan will be able to discern the appropriate dosages of the above agents for co-delivery with the IL-17 antagonist (e.g., secukinumab).

Kits and Articles of Manufacture

Disclosed herein are kits (i.e., an article of manufacture) useful for providing an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof), for the treatment of RA. Such kits may comprise an IL-17 antagonist (e.g., secukinumab) (e.g., in liquid or lyophilized form) or a pharmaceutical composition comprising the IL-17 antagonist (e.g., secukinumab). Additionally, such kits may comprise means for administering the IL-17 antagonist (e.g., secukinumab) (e.g., a syringe or a prefilled pen) and instructions for use. These kits may contain additional therapeutic agents (described supra) for treating RA, e.g., for delivery in combination with the enclosed IL-17 antagonist (e.g., secukinumab).

Disclosed herein are kits comprising: a) an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof); b) instructions for administering the IL-17 antagonist (e.g., secukinumab), to a high risk RA patient; c) means for administering the IL-17 antagonist (e.g., secukinumab) to the patient; and d) optionally, a therapeutically effective amount of at least one anti-rheumatic agent selected from the group consisting of an immunosuppressive agent, a disease-modifying anti-rheumatic drug (DMARD), a pain-control drug, a steroid, a non-steroidal anti-inflammatory drug (NSAID), a cytokine antagonist, a bone anabolic, a bone anti-resorptive, and combinations thereof. In some embodiments the high risk RA patient: a) is RF+, ACPA+, or both RF+ and ACPA+; and b) has a high level of CRP, a high ESR, or both a high level of CRP and a high ESR.

Disclosed herein are kits comprising: a) an IL-17 antagonist, e.g., IL-17 binding molecule (e.g., IL-17 antibody or antigen binding fragment thereof, e.g., secukinumab), or IL-17 receptor binding molecule (e.g., IL-17 antibody or antigen binding fragment thereof) or a pharmaceutical composition comprising an IL-17 antagonist, for use in the treatment of rheumatoid arthritis (RA) in a patient; and b) instructions describing how to administer said pharmaceutical composition to the patient, wherein the patient is characterized as: i) being RF+, ACPA+, or both RF+ and ACPA+; and ii) having a high level of CRP, a high ESR, or both a high level of CRP and a high ESR.

Also disclosed herein are in vitro test methods for selecting a patient for treatment of RA, comprising determining if: i. the patient is RF+, ACPA+, or both RF+ and ACPA+; and ii. the patient has a high level of CRP, a high ESR, or both a high level of CRP and a high ESR. In some embodiments of the test method, the patient is expected to have an improved therapeutic response to the following regimen: a) either i) administering the patient three doses of about 10 mg/kg of an IL-17 antagonist, e.g., IL-17 binding molecule (e.g., IL-17 antibody or antigen binding fragment thereof, e.g., secukinumab), or IL-17 receptor binding molecule (e.g., IL-17 antibody or antigen binding fragment thereof), the first dose being delivered during week zero, the second dose being delivered during week two, and the third dose being delivered during week four or ii) administering the patient weekly doses of about 75 mg or about 150 mg of an IL-17 antagonist, e.g., IL-17 binding molecule (e.g., IL-17 antibody or antigen binding fragment thereof, e.g., secukinumab), or IL-17 receptor binding molecule (e.g., IL-17 antibody or antigen binding fragment thereof) for four or five (preferably five) doses; and b) thereafter administering the patient about 75 mg-about 300 mg of the IL-17 antagonist twice a month, monthly, every two months or every three months (preferably monthly), beginning during week eight. These in vitro methods may be performed on biological samples (e.g., blood, cartilage, bone, serum, etc.) extracted from the patient and may be used in determining the mode or course of treatment for a particular patient, e.g., whether to administer the IL-17 antagonist to the patient (alone or in combination with another compound, e.g., such as methotrexate), or whether to choose alternative therapies (e.g., anti-TNF treatment).

Diagnostic Methods and Methods of Producing a Transmittable Form of Information

Disclosed herein are methods for determining (predicting) the likelihood that an RA patient will respond favorably (e.g., reduced sign and symptoms, reduced joint damage, increased quality of life, etc.) to treatment with an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof). Such methods will help physicians determine a course of treatment for a particular RA patient.

Disclosed herein are also methods of determining the likelihood that an RA patient will respond to treatment with an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof), comprising assaying a sample from the patient for: a) rheumatoid factor (RF), anti-citrullinated protein antibody (ACPA), or RF and ACPA; and b) C-reactive protein (CRP), an erythrocyte sedimentation rate (ESR), or both CRP and an ESR, wherein the patient is likely to respond to treatment of RA with the IL-17 antagonist (e.g., secukinumab) if the patient is RF+, ACPA+, or RF+ and ACPA+; and the patient has a high level of CRP, a high ESR, or a high level of CRP and a high ESR then the patient. In some embodiments, prior to the step of assaying, a sample is first obtained from the patient (e.g., by extracting blood or other biological tissue from the patient).

Disclosed herein are also methods of predicting the likelihood that an RA patient will respond to treatment with an IL-17 antagonist, e.g., IL-17 binding molecule (e.g., IL-17 antibody or antigen binding fragment thereof, e.g., secukinumab) or IL-17 receptor binding molecule (e.g., IL-17 antibody or antigen binding fragment thereof) comprising, determining whether a patient: a) is RF+ and/or ACPA; and 2) has a high level of CRP and/or a high ESR, wherein the patient has an increased likelihood or responding to treatment with the IL-17 antagonist if the patient is RF+, ACPA+, or RF+ and ACPA+; and has a high level of CRP, a high ESR, or a high level of CRP and a high ESR. In some embodiments, prior to the step of determining, a sample is first obtained from the patient (e.g., by extracting blood or other biological tissue from the patient).

Disclosed herein are also methods of determining the likelihood that an RA patient will respond to treatment with an IL-17 antagonist, e.g., IL-17 binding molecule (e.g., IL-17 antibody or antigen binding fragment thereof, e.g., secukinumab) or IL-17 receptor binding molecule (e.g., 11-17 antibody or antigen binding fragment thereof) comprising, assaying a sample from the patient for the baseline level of C-reactive protein (CRP), wherein the patient is likely to respond to treatment of RA with the IL-17 antagonist (e.g., secukinumab) if the patient has elevated baseline CRP. In some embodiments, prior to the step of assaying, a sample is first obtained from the patient (e.g., by extracting blood or other biological tissue from the patient).

For these diagnostic and prognostic methods, a sample from the patient may be assayed by any conventional means for detecting the factor (RF, ACPA, CRP, ESR) or level of factor, e.g., radial immunodiffusion, electroimmunoassay, immunoturbidimetry, Western blot, Norther blot, ELISA, turbidimetric methods, fluorescence polarization immunoassay, laser nephelometry, an agglutination test, a nephelometry test, measuring the distance that red blood cells precipitate in a tube over time (e.g., in the case of ESR), etc. The terms "assaying" and "determining" contemplate a transformation of matter, e.g., a transformation of a biological sample, e.g., a blood sample or other tissue sample, from one state to another by means of subjecting that sample to physical testing. Further, as used herein, the terms "assaying" and "determining" are used to mean testing and/or measuring. The phrase "assaying a sample from the patient for . . . " and the like is used to mean that a sample may be tested (either directly or indirectly) for either the presence or nonpresence of a given factor or for the level of a particular factor. It will be understood that, in a situation where the presence of a substance denotes one probability and the absence of a substance denotes a different probability, then either the presence or the absence of such substance may be used to guide a therapeutic decision. In some embodiments, prior to treatment with the IL-17 antagonist, a skilled clinician will determine whether a patient is a high risk RA patient.

Typically, once the presence or absence of a particular factor, or the level of a particular factor is identified, physicians or genetic counselors or patients or other researchers may be informed of the result. Specifically, the result can be cast in a transmittable form of information that can be communicated or transmitted to other researchers or physicians or genetic counselors or patients. Such a form can vary and can be tangible or intangible. The result with regard to the presence or absence of RF and/or ACPA, and/or the level of CRP and/or ESR in the individual tested can be embodied in descriptive statements, diagrams, photographs, charts, images or any other visual forms. For example, images of gel electrophoresis of PCR products can be used in explaining the results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of RF and/or ACPA, and/or the level of CRP and/or ESR in the individual tested can also be recorded in a sound form and transmitted through any suitable media, e.g., analog or digital cable lines, fiber optic cables, etc., via telephone, facsimile, wireless mobile phone, internet phone and the like. All such forms (tangible and intangible) would constitute a "transmittable form of information". Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present disclosure also encompasses a method for producing a transmittable form of information on the presence or absence of RF and/or ACPA, and/or the level of CRP and/or ESR in an individual.

Disclosed herein are methods for producing a transmittable form of information on a patient having RA, comprising: a) assaying a sample from the patient for: i) rheumatoid factor (RF), anti-citrullinated protein antibody (ACPA), or RF and ACPA; and ii) C-reactive protein (CRP), an erythrocyte sedimentation rate (ESR), or both CRP and an ESR; and b) embodying the result of the assaying step in a transmittable form of information. In some embodiments, following the step of embodying, a health care provider (e.g., physician) uses the transmittable form of information in making a decision to prescribe one of the treatment regimens disclosed herein, using the IL-17 antagonists disclosed herein. In some embodiments, following the step of embodying, a health care provider (e.g., physician) administers an IL-17 antagonist to the patient if the transmittable form of information identifies the patient as a high risk RA patient.

General

All patents, published patent applications, publications, references and other material referred to herein are incorporated by reference herein in their entirety. The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference. The following Examples are presented in order to more fully illustrate the preferred embodiments of the disclosure. These examples should in no way be construed as limiting the scope of the disclosed patient matter, which is defined by the appended claims.

EXAMPLES

Example 1: Use of Secukinumab to Treat Rheumatoid Arthritis (RA) (CAIN457F2201)

Example 1.1—Study Design

The study population consists of a representative group of patients (male or non-pregnant, nonlactatin females) of at least 18 years of age, fulfilling ACR 1987 revised classification criteria for RA for at least 3 months. Eligible patients were required to present active RA defined by ≥6 out of 28 tender joints and ≥6 out of 28 swollen joints, and hsCRP≥10 mg/L OR ESR≥28 mm/1st hour (mm/h) at the time of randomization to assure ability to detect response to treatment using ACR criteria. Eligible candidates were on MTX for at least 3 months and at selection were currently treated with a stable weekly dose of MTX (≥7.5 mg/week-≤25 mg/week) for at least 4 weeks.

Adult RA patients (n=237) on methotrexate were randomized equally to receive monthly s.c. injections of secukinumab 25 mg, 75 mg, 150 mg, 300 mg or placebo. Patients with previous exposure to biologics were included in all cohorts (18-22%). The primary end point was the proportion of patients achieving American College of Rheumatology (ACR) 20 at week 16. At Week 20 (Visit 8), patients who were randomized to placebo at Week 0 or who were randomized to secukinumab but did not achieve an ACR20 response at Week 16 were re-assigned to receive double blind treatment up to Week 48, with a final efficacy assessment performed at Week 52, and a follow up visit at Week 60, as follows starting at Week 20 (FIG. 1):

- Patients on active treatment who were responders continued on their dose regimen;
- All placebo patients were switched to active treatment 150 mg s.c. q4wk (monthly), independent of disease activity;
- All patients treated with 25 mg or 75 mg secukinumab q4wk who were non-responders were switched to 150 mg s.c. q4wk;
- Non-responders in the 150 mg group were switched to the next highest dose—300 mg s.c. q4wk;
- All patients on 300 mg group remained on their respective dose to assess if exposure longer than 16 weeks will induce a clinical response in these patients.

Efficacy assessments are ACR20, 50, 70 (Felson et al. (1995) Arthritis Rheum; 38(6):727-35) and DAS28 response/remission (Fransen et al (2003) Ann Rheum Dis; 62(Suppl 1): 10; Prevoo et al. (1995) Arthritis Rheum; 38(1):44-48). The primary efficacy variable is the clinical response to treatment according to ACR20 individual improvement in disease activity at Week 16. Results are assessed by the proportion of patients achieving the ACR20 response criteria at Week 16. A patient will be considered a responder according to ACR20 criteria if he/she has:

A) at least 20% improvement in the two following measures:
- tender 28-joint count
- swollen 28-joint count; and B) at least 20% improvement in at least 3 of the following 5 measures:
- Patient's assessment of RA pain (VAS 100 mm)
- Patient's global assessment of disease activity (VAS 100 mm)
- Physician's global assessment of disease activity (VAS 100 mm)
- Patient self-assessed disability (Health Assessment Questionnaire [HAQ©] score)
- Acute phase reactant (C-reactive protein [hsCRP] or erythrocyte sedimentation rate (ESR)) Additional measures include: ACR50 (50% improvement in item B (above) in at least 3 of the 5 measures and 50% improvement in the swollen and tender joint count) and ACR70 (70% improvement in item B (above) in at least 3 of the 5 measures and 70% improvement in the swollen and tender joint count).

The DAS28 (Disease Activity Score—28) is a well-established measure of disease activity in RA. The score is calculated by a complex mathematical formula, which includes the number of tender and swollen joints (out of a total of 28), the erythrocyte sedimentation rate (ESR) or hsCRP, and the patient's global assessment of global health (indicated by marking a 100 mm line between very good and very bad). A DAS28 score greater than 5.1 implies active disease, less than 3.2 well controlled disease, and less than 2.6 remission.

In order to calculate the DAS28, information about the following disease variables is needed:

- The number of swollen joints and tender joints should be assessed using 28-joint count (tender28 and swollen28).
- The erythrocyte sedimentation rate (ESR) should be measured in mm/hour.
- The patient's general health (GH) or global disease activity measured on a Visual Analogue Scale (VAS) of 100 mm (both are useable for this purpose) must be obtained.

Using this data, the DAS28 can be calculated using the following formula:

DAS28=0.56*sqrt(tender28)+0.28*sqrt(swollen28)+0.70*ln(ESR)+0.014*GH

C-reactive protein (CRP) may be used as an alternative to ESR in the calculation of the DAS or DAS28, using the formulas below. CRP is a more direct measure of inflammation than ESR, and it is more sensitive to short-term changes. CRP production is associated with radiological progression in RA, and is considered at least as valid as ESR to measure RA disease activity. Another advantage of determination of CRP is that waiting time for the laboratory result is shorter and that in case of multicenter studies a central laboratory can be used. The following formulas to calculate the DAS28 using CRP (mg/L) give good estimations of the original DAS28 values on a group level.

DAS28-4(crp)=0.56*sqrt(TJC28)+0.28*sqrt(SJC28)+0.36*ln(CRP+1)+0.014*GH+0.96

TJC28: 28 Tender joint count; SJC28: 28 Swollen joint count; CRP: C-reactive protein; GH: General Health on a 100 mm. Visual Analogue Scale.

The HAQ© is a validated measure of physical disability and functional status. It has four dimensions: disability, pain, drug side effects and dollar costs, although, the latter three are rarely used in clinical trials. In this trial only the disability dimension was used. The disability dimension consists of 20 multiple choice items concerning difficulty in performing eight common activities of daily living; dressing and grooming, arising, eating, walking, reaching, personal hygiene, gripping and activities. Subjects choose from four response categories, ranging from 'without any difficulty' to 'unable to do'. The ACR Rheumatology Committee on Outcome Measures in RA recommends the use of this questionnaire in clinical trials. The HAQ© is scored in accordance with the recommendation from the developers outlined in the "HAQ PACK" from Stanford University, California.

Example 1.2—Statistical Analysis

To test superiority of secukinumab treatment groups over placebo, the ACR20 responder rate (proportion) was compared against placebo for each of the secukinumab-treated groups based on a logistic regression model with treatment, center and baseline DAS28 as covariates. The DAS28-CRP change from baseline was analyzed using an analysis of covariance (ANCOVA, SAS PROC MIXED) fixed effects model with treatment as main effect and correcting for the covariates center and baseline value. All statistical tests for pairwise comparisons of secukinumab treatment groups vs placebo were performed at two-sided 5% significance level. The method of last observation carried forward (LOCF) was used for missing values for efficacy variables. Figures were produced presenting response over time or at specific time points up to Week 16 (or Week 52, as appropriate). Of note, for figures presenting results up to Week 52, only data from patients continuing at Week 24 were included.

The full analysis set (FAS) was used for the reporting of the efficacy results. The FAS comprised all patients to whom study drug had been assigned. Following the intent-to-treat (ITT) principle, patients were analyzed according to the treatment and stratum they were assigned to at randomization.

Example 1.3—Week 16 Results

Figure 2A:
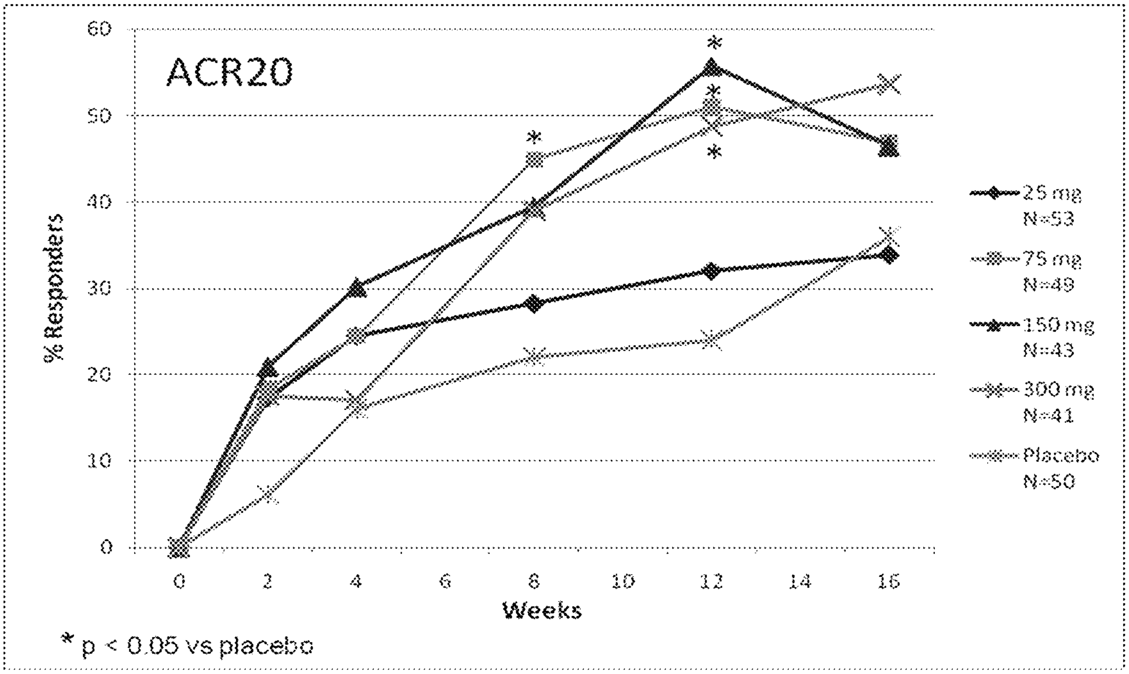
FIG. 2A shows ACR20 response last observation carried forward (LOCF) by treatment up to week 16 in study CAIN457F2201 in full analysis set (FAS).
Figure 3A:
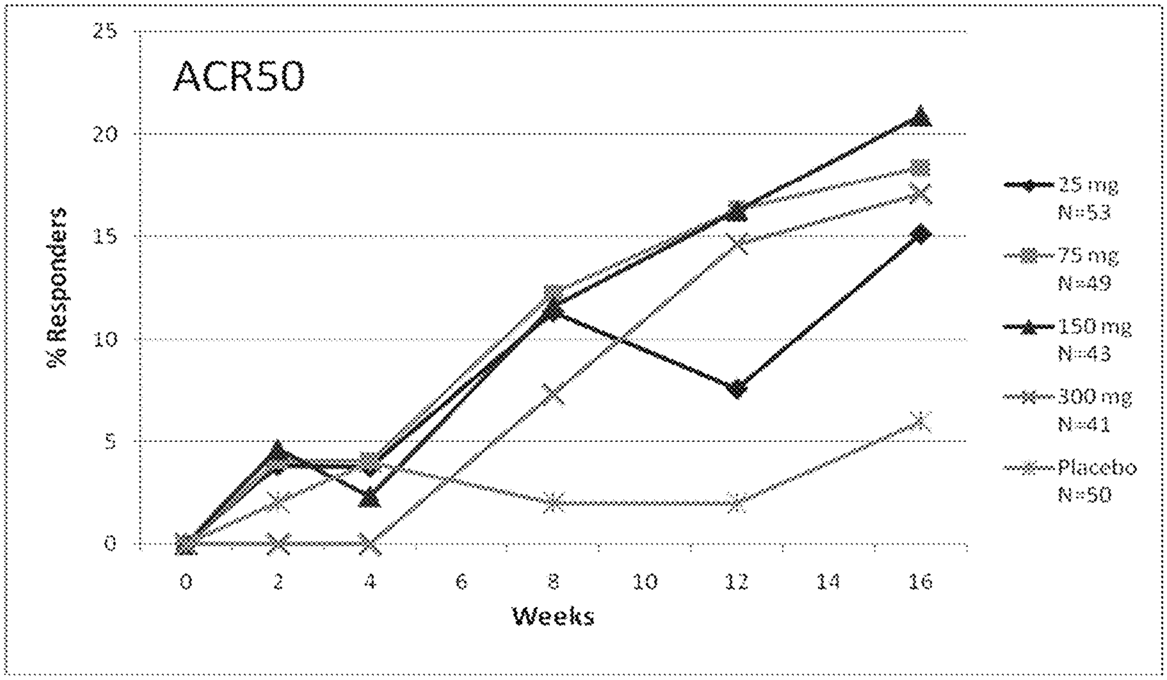
FIG. 3A shows ACR50 response (LOCF) by treatment up to week 16 in study CAIN457F2201 in full analysis set (FAS).
Figure 4A:
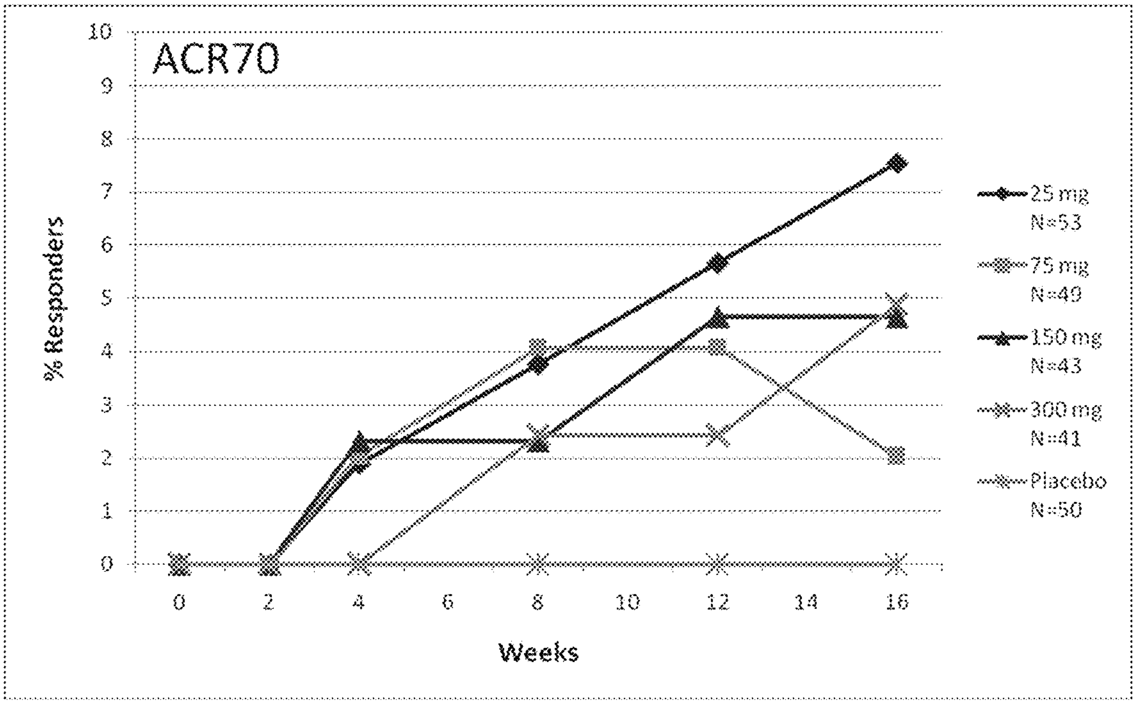
FIG. 4A shows ACR70 response (LOCF) by treatment up to week 16 in study CAIN457F2201 in full analysis set (FAS).
Figure 5A:
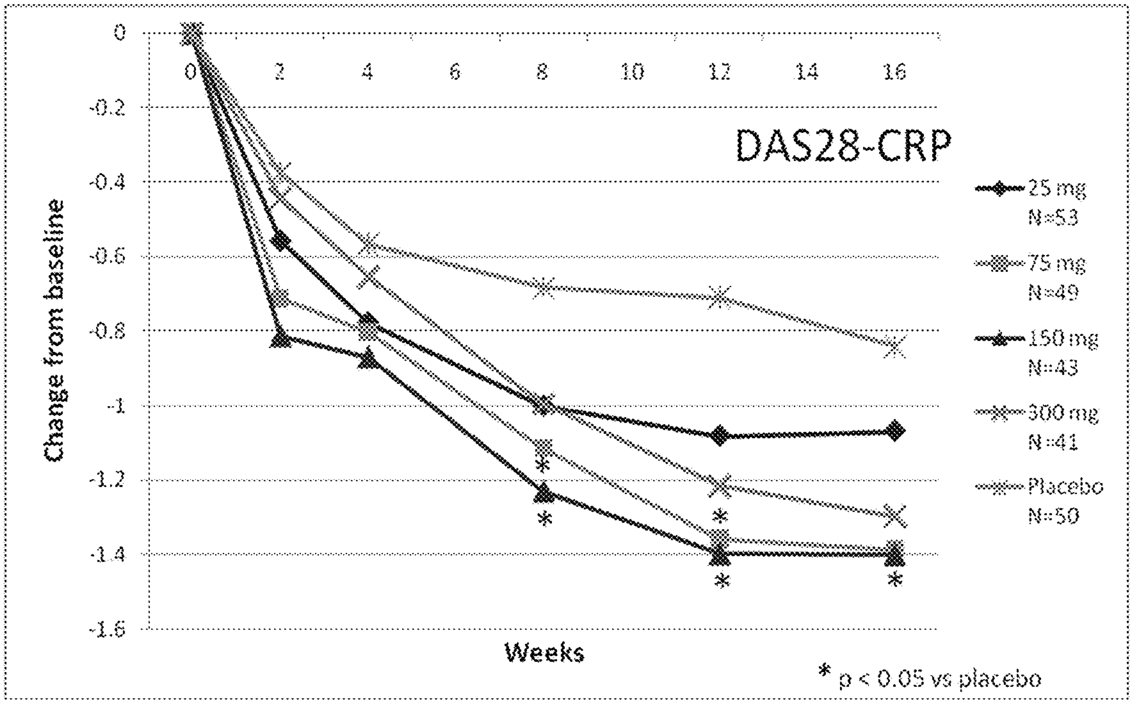
FIG. 5A shows DAS28-CRP change from baseline (LOCF) by treatment up to week 16 in study CAIN457F2201 FAS.
Figure 6A:
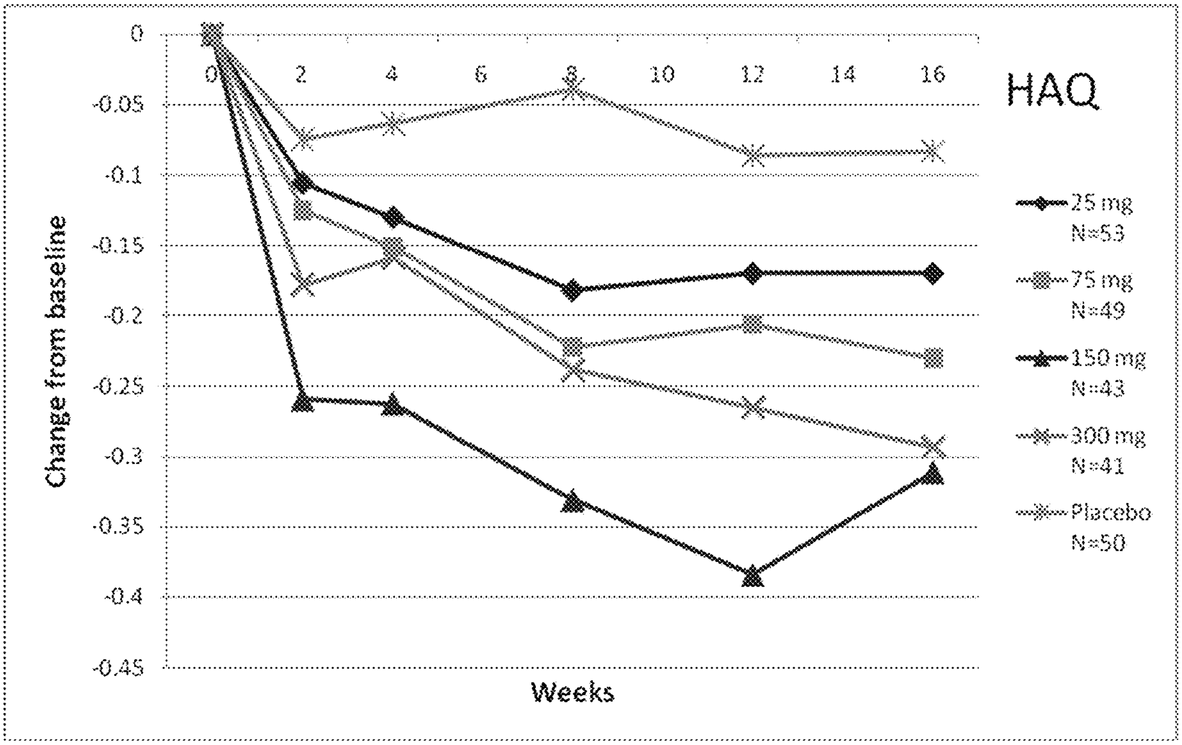
FIG. 6A shows HAQ© scores change from baseline (LOCF) by treatment up to week 16 in study CAIN457F2201 FAS.

Demographics and baseline characteristics were comparable across all groups. ACR20 responders at Week 16 were higher in the secukinumab 75 mg, 150 mg and 300 mg dose groups (46.9%, 46.5% and 53.7%, respectively) compared to placebo (36.0%) and compared to secukinumab 25 mg (34%) (FIG. 2A). However, these results did not achieve statistical significance due to a marked and unexplained increase in ACR20 in the placebo group between Week 12 (24%) and 16 (36%). Clinically relevant reductions in DAS28-CRP were observed in the secukinumab 75-300 mg treatment groups vs. placebo (FIG. 5A). Serum CRP levels at Week 16 were markedly reduced in secukinumab 75-300 mg groups vs. placebo ($p=0.0012$, 0.0081 and 0.0241) (data not shown). ACR50 and ACR70 showed consistent greater improvements with secukinumab 75-300 mg doses vs. placebo over 16 weeks (FIGS. 3A and 4A). There was about a 4-fold average reduction from baseline in the HAQ© score at week 16 in the 150-300 mg groups compared to placebo (FIG. 6A).

Example 1.4—Week 24 Results

By Week 24, ACR20 responses were maintained and DAS28 CRP responses further improved in the 75-300 mg groups with secukinumab treatment between week 16 and 24. HAQ© scores were either maintained or further reduced in the 75-300 mg groups with groups with secukinumab treatment between week 16 and 24. The 75-300 mg ACR20 responder treatment groups exhibited an early improvement in HAQ© scores over time through Week 24. ACR50 responses further improved from 19-24% (75 mg), 21-25% (150 mg) and 19-24% (300 mg) in patients originally randomized to the respective dose cohorts, part of whom had a dose escalation at Week 20; a similar improvement was seen in ACR70 responses in the 75 mg-150 mg groups. An increase in the ACR20/50/70 response in the patients randomized to placebo between Week 16 and 24 can also be noted. All patients on placebo up to Week 16 were switched to secukinumab 150 mg at Week 20.

Example 1.5—Week 52 Results

Figure 2C:
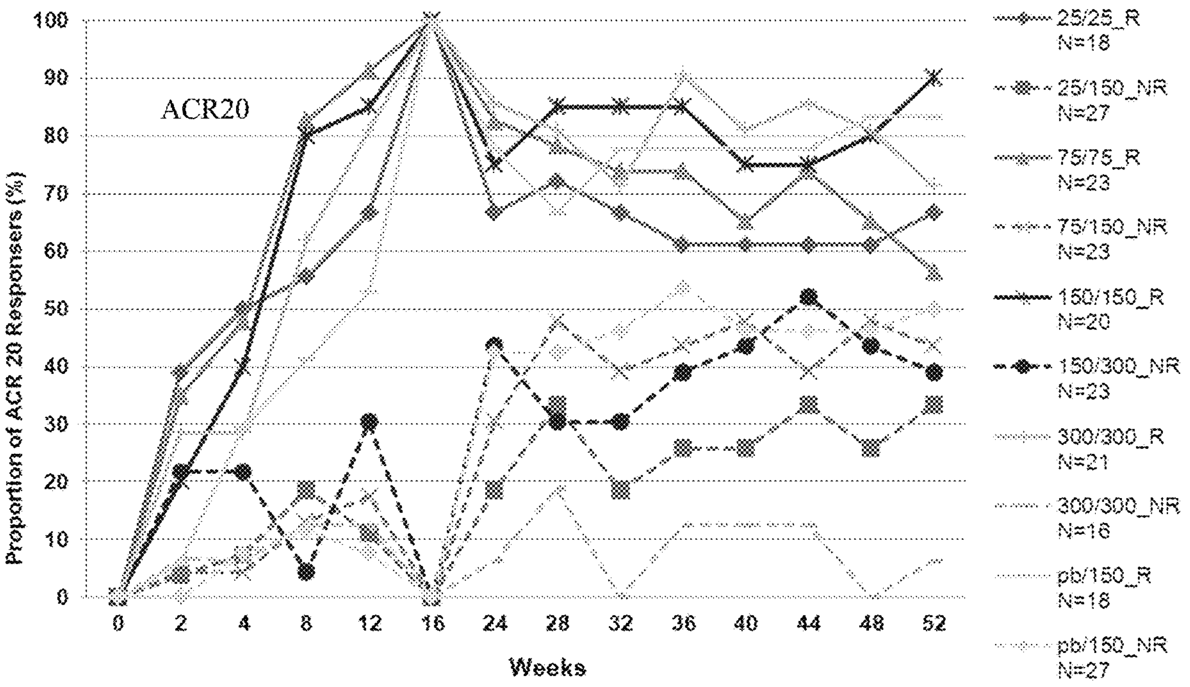
FIG. 2C shows the ACR20 response over time through week 52 by responders (R) and non-responders (NR) in the FAS.
Figure 3B:
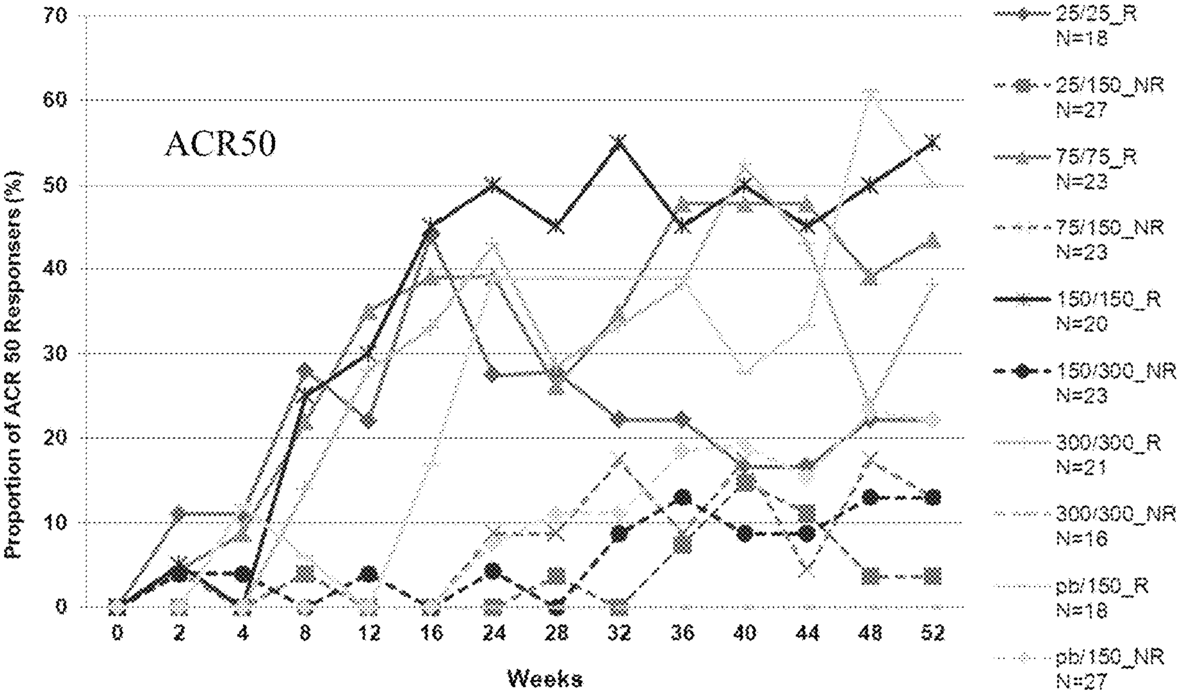
FIG. 3B shows the ACR50 response over time through week 52 by responders (R) and non-responders (NR) in the FAS.
Figure 4B:
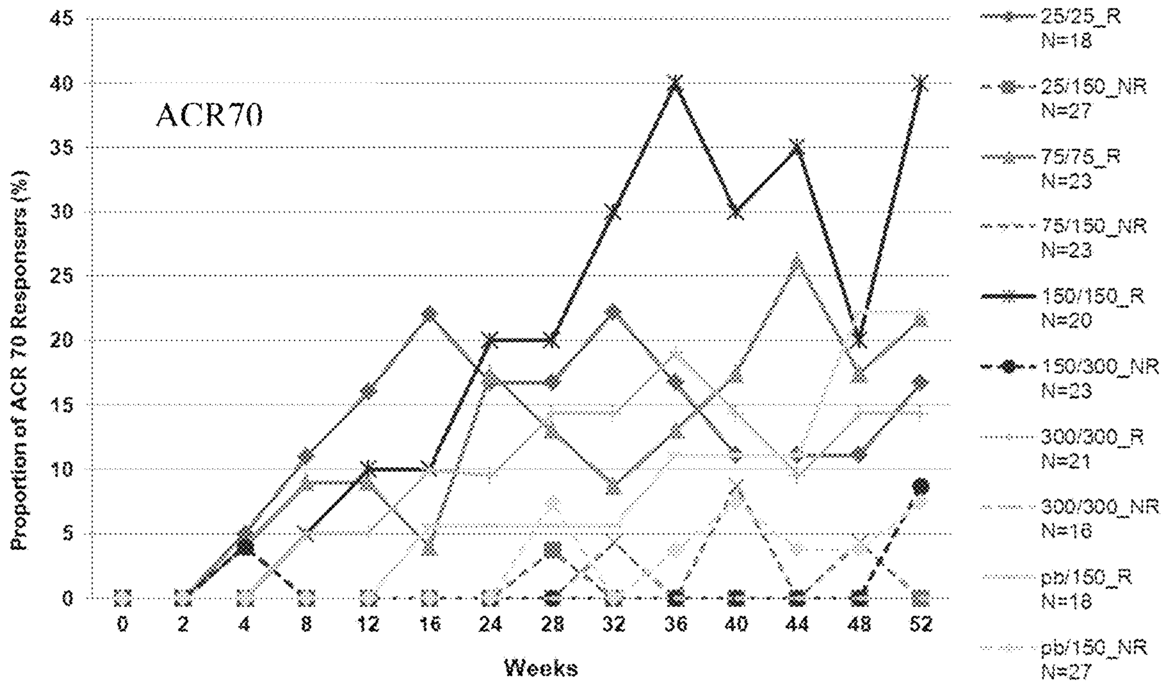
FIG. 4B shows the ACR70 response over time through week 52 by responders (R) and non-responders (NR) in the FAS.
Figure 5B:
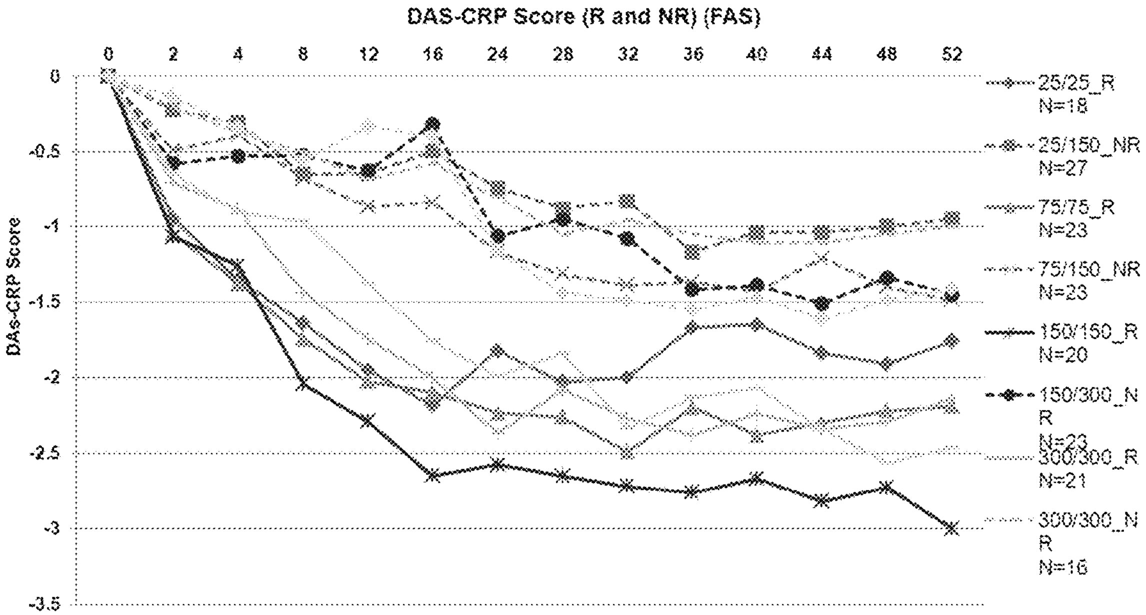
FIG. 5B shows the DAS28-CRP response over time through week 52 by responders (R) and non-responders (NR) in the FAS.
Figure 6B:
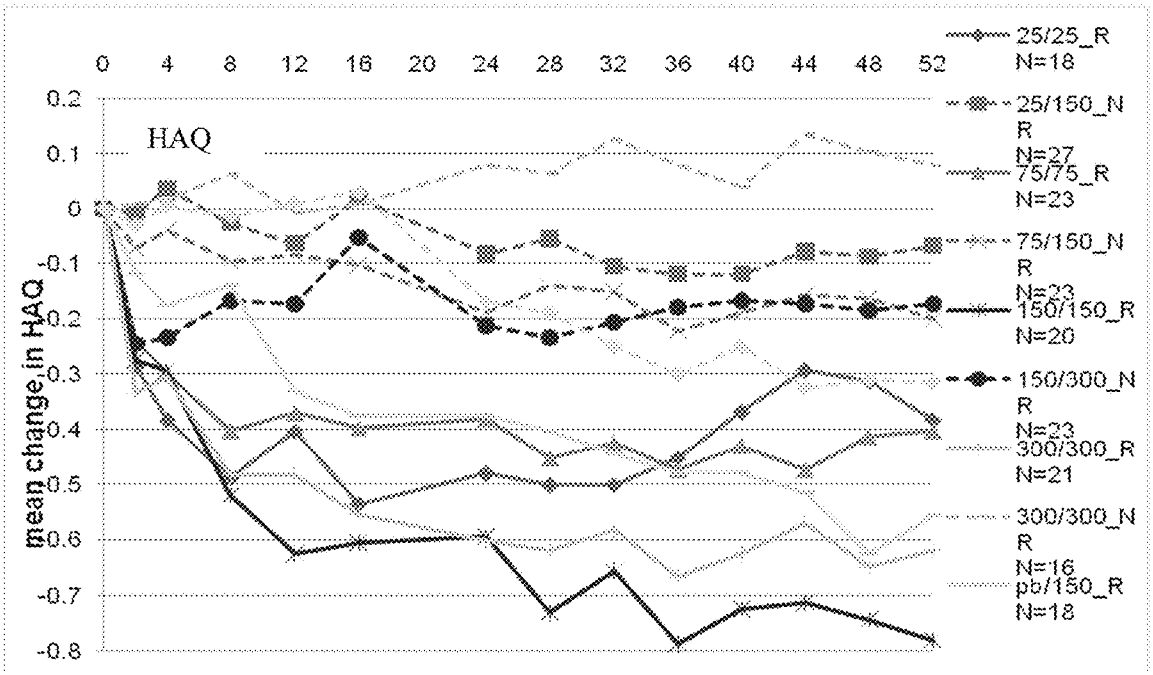
FIG. 6B shows the HAQ© response over time through week 52 by responders (R) and non-responders (NR) in the FAS.
Figure 7:
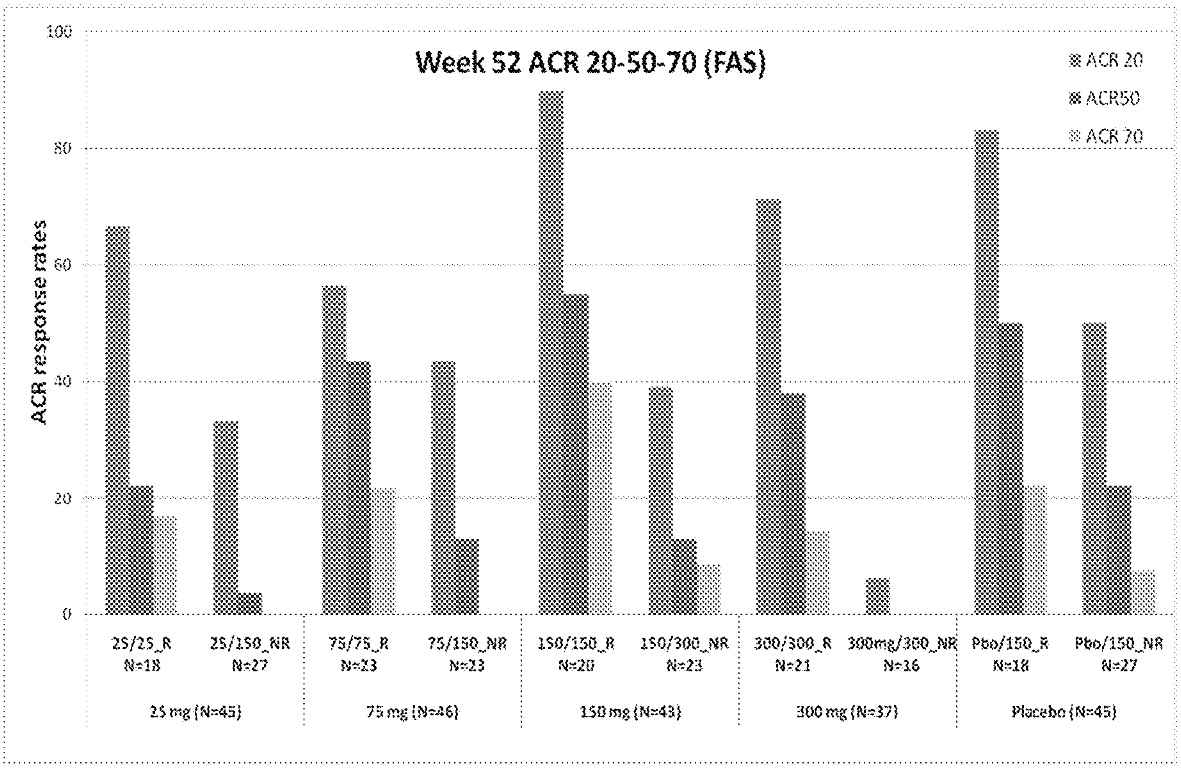
FIG. 7 shows the ACR20/50/70 response at week 52 by responders (R) and non-responders (NR) in the FAS.

With respect to efficacy of secukinumab over time patients who had been responders at week 16 generally maintained their responses in terms of ACR 20 (FIG. 2C), ACR50 (FIG. 3B) and ACR70 (FIG. 4B) with best responses seen in the 150 mg responder cohort. The same was also true for DAS28-CRP and HAQ scores Reponses which were maintained in responders at week 16 over time through week 52 again with best responses observed in the 150 mg responder cohort (FIG. 5B, 6B). ACR20, 50 and 70 responses at week 52 are shown in FIG. 7 again with highest responses for all these parameters in the 150 mg responder cohort.

Biological failure patients were 18-22% in each cohort at study start. Of patients previously exposed to biologics who were dosed with 150 mg secukinumab after Week 20, 62% (8 of 13) achieved an ACR20, 38% (5 of 13) achieved an ACR50 and 23% achieved an ACR 70 at Week 52. This provides evidence that secukinumab is capable of treating RA in patients who failed anti-TNF and other biological therapy.

Example 2: Analysis of High Risk RA Patient Subset in CAIN457F2201

Example 2.1—Statistical Analysis

In searching for indicators predictive of an RA patient's response to treatment with secukinumab, we analyzed two of the four 2010 ACR/EULAR scoreable criteria (see Table 1) to determine how (and whether) these criteria may influence response to treatment with secukinumab with data from the CAIN457F2201 trial database. First, we analyzed serology to determine whether the patient is RF+ and/or anti-CCP+ (i.e., ACPA+). Second, we analyzed the presence of acute-phase reactants to determine whether the patient has a high level of C-reactive protein (CRP) and/or a high erythrocyte sedimentation rate (ESR).

Analysis was mainly performed with summary statistics (proportions for binary response variables and average for continuous variables) produced over time to observe responses up to Week 16 (or 52, for patients who continued at Week 24). The method of last observation carried forward (LOCF) was used for missing values for efficacy variables. Data were produced presenting response over time or at specific time points up to Week 16 (or Week 52, as appropriate). Of note, for data showing results up to Week 52, only data from patients continuing at Week 24 were included.

Example 2.2—Analysis of Responses to Secukinumab in High Risk RA Patients

Figure 2B:
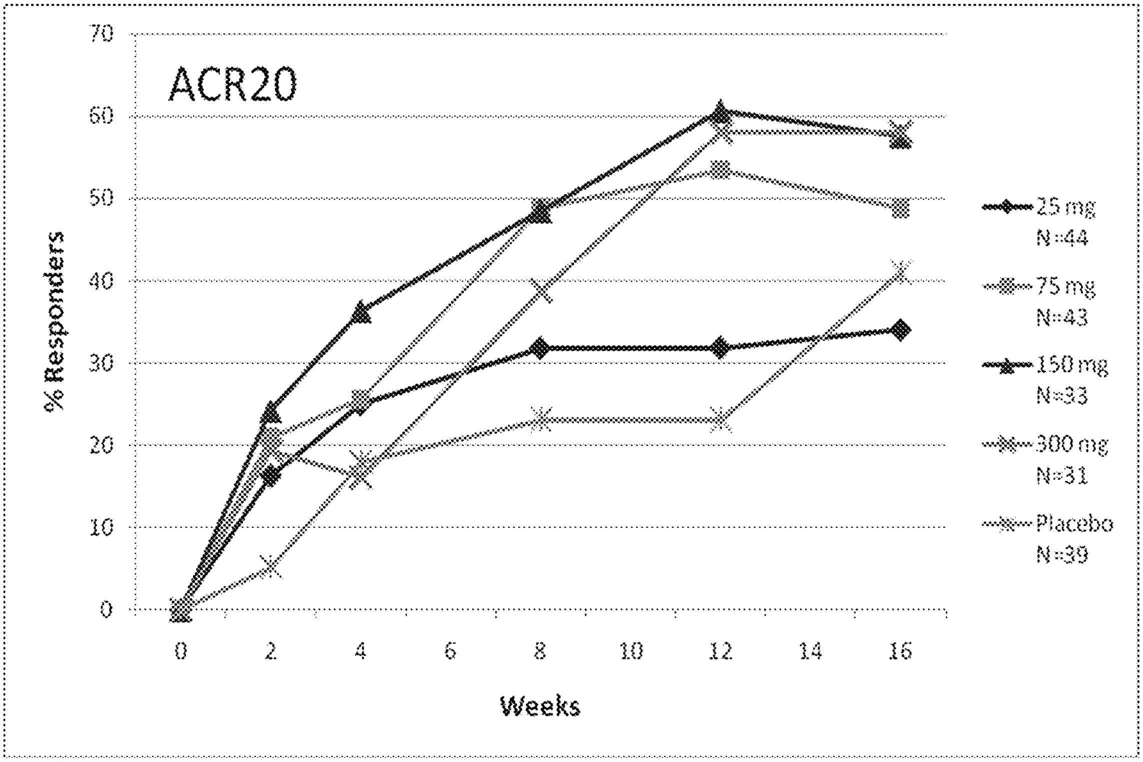
FIG. 2B shows ACR20 response (LOCF) by treatment up to week 16 in high risk RA patients.

The analysis of subgroup of patients with "high risk" (i.e., "high risk RA patients") for disease progression (based on high CRP and/or ESR, and positive RF and/or ACPA) showed promising results in the secukinumab treated patients compared to the CAIN457F2201 overall trial results, while the responses in the placebo group did not show similar increased trend. In terms of ACR20, in the FAS, 46.9, 46.5, 53.7 and 36% response was observed at Week 16 in the secukinumab 75, 150, 300 mg and placebo (FIG. 2A and Table 6), respectively, whereas 48.8, 57.6, 58.1 and 41.0% responses was observed at Week 16 in the high risk subgroup (FIG. 2B and Table 6). Similarly, increased response rates were observed at Weeks 16 and 52 in the high risk subgroup compared to the FAS, and in other variables such as ACR50/70 (Table 6), DAS28-CRP (Table 7), and HAQ© (data not shown).

Summaries of ACR20/50/70% and DAS28-CRP responses at weeks 16 and 52 in the FAS, the high risk RA patients, and the non-high risk RA patients are provided in Table 6 (ACR) and Table 7 (DAS28-CRP). Graphical depiction of the ACR20/50/70% and DAS28-CRP responses at week 16 in the high risk RA patients and the non-high risk RA patients are provided in FIGS. 8A and 8B.

TABLE 6

ACR responses (LOCF) at weeks 16 and 52 in FAS, high risk RA patients, and non high risk RA patients.

| | | Placebo | 25 mg | 75 mg | 150 mg | 300 mg |
|---|---|---|---|---|---|---|
| Week 16 | | | | | | |
| FAS | ACR20 | 18/50 (36.0%) | 18/53 (34.0%) | 23/49 (46.9%) | 20/43 (46.5%) | 22/41 (53.7%) |
| | ACR50 | 3/50 (6.0%) | 8/53 (15.1%) | 9/49 (18.4%) | 9/43 (20.9%) | 7/41 (17.1%) |
| | ACR70 | 0/50 (0.0%) | 4/53 (7.5%) | 1/49 (2.0%) | 2/43 (4.7%) | 2/41 (4.9%) |
| High risk RA | ACR20 | 16/39 (41.0%) | 15/44 (34.1%) | 21/43 (48.8%) | 19/33 (57.6%) | 18/31 (58.1%) |
| patient | ACR50 | 2/39 (5.1%) | 7/44 (15.9%) | 8/43 (18.6%) | 8/33 (24.2%) | 5/31 (16.1%) |
| subgroup | ACR70 | 0/39 (0.0%) | 3/44 (6.8%) | 1/43 (2.3%) | 2/33 (6.1%) | 1/31 (3.2%) |
| Non High risk | ACR20 | 2/11 (18.2%) | 3/9 (33.3%) | 2/6 (33.3%) | 1/10 (10.0%) | 4/10 (40.0%) |
| RA patient | ACR50 | 1/11 (9.1%) | 1/9 (11.1%) | 1/6 (16.7%) | 1/10 (10.0%) | 2/10 (20.0%) |
| subgroup | ACR70 | 0/11 (0.0%) | 1/9 (11.1%) | 0/6 (0.0%) | 0/10 (0.0%) | 1/10 (10.0%) |
| Week 52 | | | | | | |
| FAS | ACR20 | 27/44 (61.4%) | 18/45 (40.0%) | 26/46 (56.5%) | 26/43 (60.5%) | 17/31 (45.9%) |
| | ACR50 | 17/44 (38.6%) | 5/45 (11.1%) | 13/46 (28.3%) | 13/43 (30.2%) | 5/37 (13.5%) |
| | ACR70 | 5/44 (11.4%) | 2/45 (4.4%) | 5/46 (10/9%) | 4/43 (9.3%) | 3/37 (8.1%) |
| High risk RA | ACR20 | 22/33 (66.7%) | 18/38 (47.4%) | 20/40 (50.0%) | 24/33 (72.7%) | 12/28 (42.9%) |
| patient | ACR50 | 14/33 (42.4%) | 4/38 (10.5%) | 11/40 (27.5%) | 13/33 (39.4%) | 5/28 (17.9%) |
| subgroup | ACR70 | 5/33 (15.2%) | 2/38 (5.3%) | 4/40 (10.0%) | 10/33 (30.3%) | 2/28 (7.1%) |
| Non High risk | ACR20 | 5/11 (45.5%) | 3/7 (42.9%) | 3/6 (50.0%) | 3/10 (30.0%) | 4/9 (44.4%) |
| RA patient | ACR50 | 3/11 (27.3%) | 1/7 (14.3%) | 2/6 (33.3%) | 1/10 (10.0%) | 3/9 (33.3%) |
| subgroup | ACR70 | 0/11 (0.0%) | 1/7 (14.3%) | 1/6 (16.7%) | 0/10 (0.0%) | 1/9(11.1%) |

TABLE 7

DAS28-ESR median change from baseline at weeks 16 and 52 in FAS, high risk RA patients, and non high risk RA patients.
Median change from baseline in DAS28-ESR

| | Placebo | 25 mg | 75 mg | 150 mg | 300 mg |
|---|---|---|---|---|---|
| Week 16 | | | | | |
| FAS | −0.97 | −0.84 | −1.40 | −1.23 | −1.38 |
| High risk RA patient subgroup | −1.00 | −0.65 | −1.22 | −1.81 | −1.23 |
| Non High risk RA patient subgroup | −0.88 | −1.17 | −1.33 | −0.27 | −0.77 |
| Week 52 | | | | | |
| FAS | −1.68 | −1.31 | −1.51 | −2.19 | −1.33 |
| High risk RA patient subgroup | −2.00 | −1.33 | −1.51 | −2.87 | −1.36 |
| Non High risk RA patient subgroup | −1.07 | −1.11 | −1.40 | −1.43 | −1.29 |

Note, for Table 6 and 7, week 52 data is presented by the original assigned treatment. Titration was performed for ACR20 non-responders (and all placebo patients) starting at week 16. 18/45 'original' 25 mg patients remained on 25 mg while 27 patients were up-titrated to 150 mg. Likewise, 23/46 'original' 75 mg patients remained on 75 mg while 23 were up-titrated to 150 mg. 20/43 'original' 150 mg patients remained on 150 mg and 23 were up-titrated to 300 mg. All 44 'original' placebo patients were switched to 150 mg and all 'original' 300 mg patients remained on 300 mg.

Figure 8A:
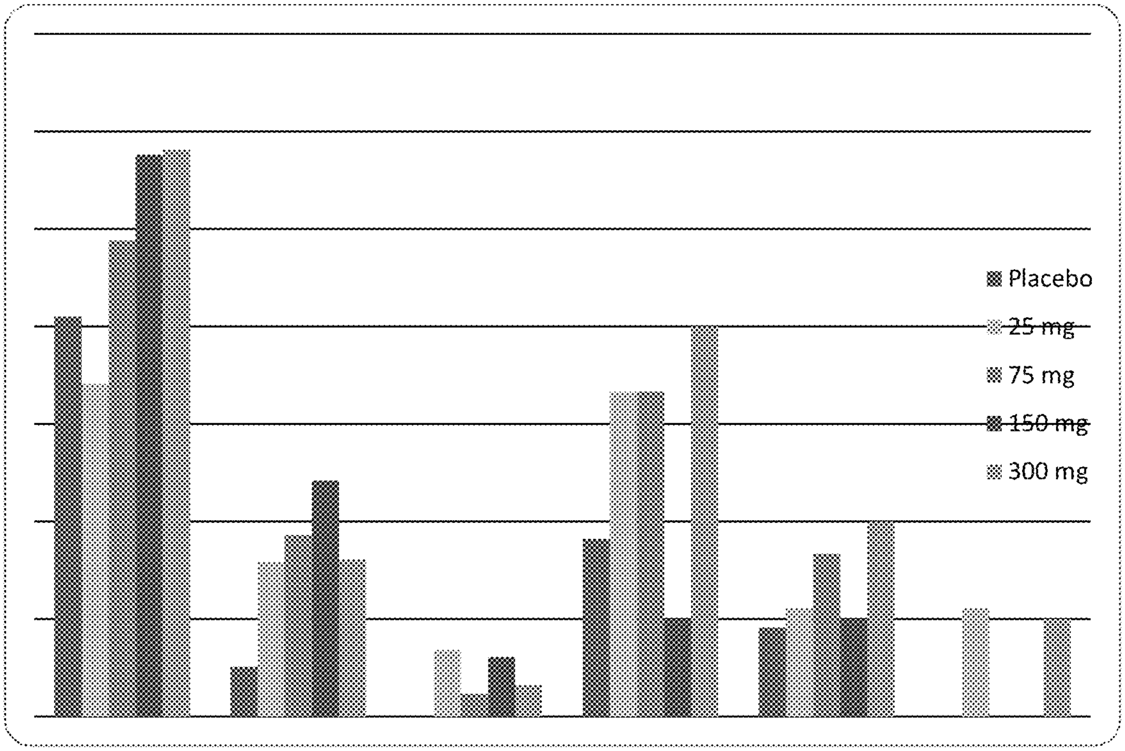
FIG. 8A shows the ACR20/50/70% response at week 16 in the high risk RA patients and non-high risk RA patients.
Figure 8B:
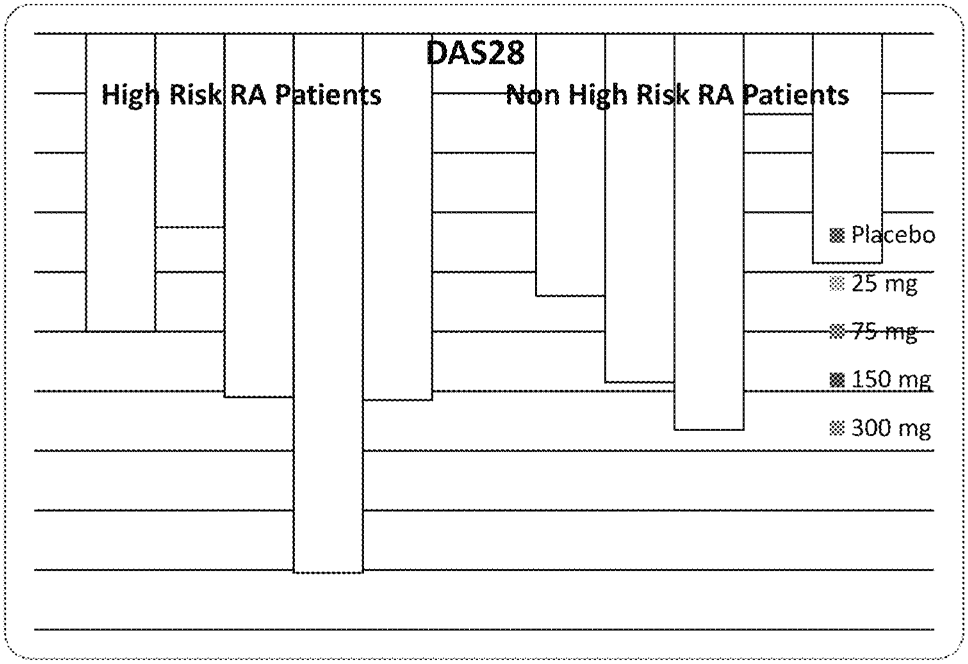
FIG. 8B shows the DAS28-CRP response at week 16 in the high risk RA patients and non high risk RA patients.

As can be seen from Tables 6 and 7, as well as FIGS. 8A and 8B, high risk RA patients generally display an improved response to IL-17 inhibition in comparison to non-high risk RA patients. Comparing the ACR20% and ACR50% response between the high risk RA patients and non-high risk RA patients at week 16 (Table 6 and FIG. 8A), a dose response can be seen in the high risk RA patients in response to IL-17 inhibition by secukinumab. A similar dose response is seen in the DAS28-CRP score in high risk RA patients at weeks 16 and 52 (Table 7 and FIG. 8B). Furthermore, ACR20% responses at week 16 in the high risk RA patient subset are improved at all doses of secukinumab above 25 mg in comparison to the ACR20% responses seen in non-high risk RA patients (Table 6 and FIG. 8A). In addition, the ACR50/70% response at weeks 16 and 52 in high risk RA patients treated with 150 mg secukinumab is higher than the ACR50/70% response in non-high risk RA patients treated with the same secukinumab dose. A similar result is seen in the DAS28-CRP score for 150 mg secukinumab at weeks 16 and for all doses of secukinumab at week 52 (Table 7 and FIG. 8B).

Example 3: Patients with Elevated Baseline CRP Benefit from Secukinumab

Example 3.1—Study Design

To evaluate the dose-response relationship of DAS28 and ACR responses at week 16 by baseline high sensitivity (hs) CRP levels in patients with RA treated with different doses of secukinumab compared to placebo.

As described previously, in study CAIN457F2201, adult RA patients (n=237) on methotrexate were randomized to receive monthly s.c. injections of secukinumab 25 mg, 75 mg, 150 mg, 300 mg, or placebo. We assessed dose relationship of DAS28 and ACR responses at week 16 by different baseline hsCRP levels (≥0 mg/L, ≥10 mg/L, ≥20 mg/L, and ≥30 mg/L).

Example 3.2—Results

Figure 9:
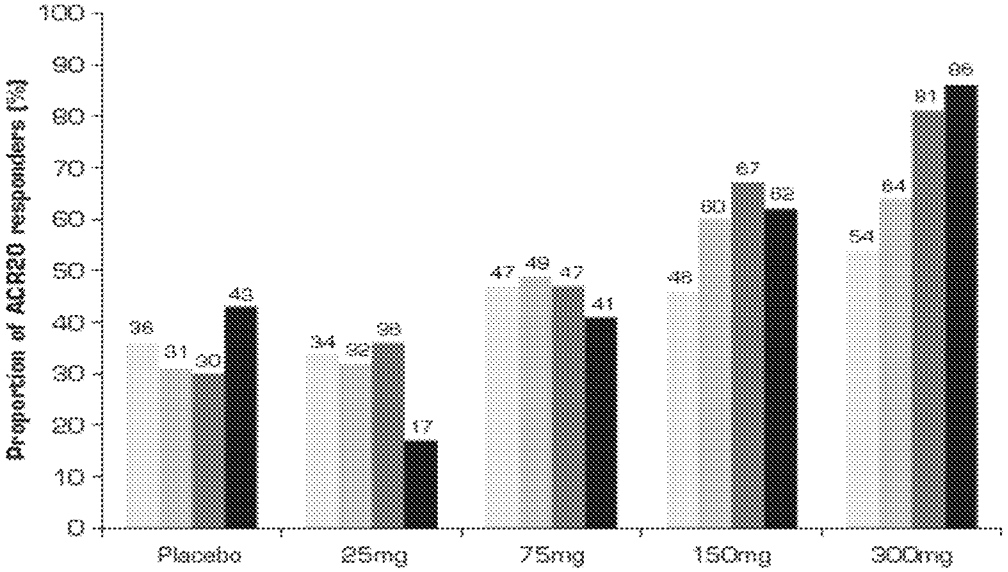
FIG. 9 shows ACR20 responder rates by dose group and CRP baseline levels in CAIN457F2201 study. Columns represent, from the left to the right, all patients, patients with a CRP baseline greater than 10 mg/L, greater than 20 mg/L, and greater than 30 mg/L, respectively.

Demographics and baseline characteristics were comparable across all groups. A rapid reduction in DAS28-CRP was observed as early as week 2 in patients on secukinumab 75 mg, 150 mg, 300 mg groups. By week 12, these patients achieved a clinically meaningful DAS28 reduction of >1.2 compared with those on placebo (P<0.05). These responses were sustained up to week 16 (Table 8). As seen in Table 8 and FIG. 9, there is a dose-dependent relationship in DAS28-CRP, ACR2, and ACR50 responses at week 16 based on baseline hsCRP levels for secukinumab 150 mg and 300 mg dose cohorts in comparison to placebo or secukinumab 25 mg and 75 mg groups. The safety profile of secukinumab up to week 20 was comparable to placebo. Most AEs were mild or moderate in severity and did not lead to study drug discontinuation.

TABLE 8

Dose-response relationship for DAS28-CRP, ACR20, and ACR50 at Week 16 by CRP levels at baseline. DAS28-CRP, ACR20, and ACR50 data are given in median; N: number of patients.

| Treatment | DAS28/ACR | CRP >= 0 | CRP >= 10 | CRP >= 20 | CRP >= 30 |
|---|---|---|---|---|---|
| | N | 53 | 25 | 11 | 6 |
| Secukinumab 25 mg | DAS28 | −1.08 | −1.24 | −1.46 | −1.03 |
| | ACR20, % | 34 | 32 | 36 | 17 |
| | ACR50, % | 15 | 17 | 19 | 17 |
| | N | 49 | 27 | 17 | 10 |
| Secukinumab 75 mg | DAS28 | −1.40 | −1.50 | −1.22 | −1.46 |
| | ACR20, % | 47 | 49 | 47 | 41 |
| | ACR50, % | 19 | 19 | 12 | 10 |
| | N | 43 | 20 | 15 | 11 |
| Secukinumab 150 mg | DAS28 | −1.38 | −2.05 | −2.13 | −2.09 |
| | ACR20, % | 46 | 60 | 67 | 62 |
| | ACR50, % | 20 | 28 | 31 | 17 |
| | N | 41 | 19 | 10 | 6 |
| Secukinumab 300 mg | DAS28 | −1.30 | −1.51 | −2.01 | −2.21 |
| | ACR20, % | 54 | 64 | 81 | 86 |
| | ACR50, % | 17 | 19 | 39 | 67 |

TABLE 8-continued

Dose-response relationship for DAS28-CRP, ACR20, and ACR50 at Week 16 by CRP levels at baseline. DAS28-CRP, ACR20, and ACR50 data are given in median; N: number of patients.

| Treatment | DAS28/ACR | CRP >= 0 | CRP >= 10 | CRP >= 20 | CRP >= 30 |
|---|---|---|---|---|---|
| | N | 50 | 26 | 16 | 12 |
| Placebo | DAS28 | −0.83 | −0.72 | −0.47 | −0.67 |
| | ACR20 | 0.36 | 0.31 | 0.30 | 0.43 |
| | ACR50 | 0.05 | 0.03 | 0.05 | 0.07 |

"0" = 0 mg/ml,
"10" = 10 mg/ml,
"20" = 20 mg/ml,
"30" = 30 mg/ml.

The results indicate that secukinumab provides a rapid reduction of disease activity with the greatest improvements seen in those patients on 150 mg or 300 mg who had evidence of high inflammatory burden as evidenced by baseline hsCRP levels. This suggests that secukinumab offers benefit to RA patients including those with factors rendering them at high risk for progressive disease.

Example 4: Modeling and Simulation: Rheumatoid Arthritis Induction Regimen Design The relationship between secukinumab dose/regimen, secukinumab plasma concentration and the ACR20 response was modeled using a PK/PD approach describing the longitudinal data. These models were used to facilitate design of Phase III trials for secukinumab in treating rheumatoid arthritis.

Example 4.1—Methods

Modeling of Secukinumab Pharmacokinetics

For the pharmacokinetic (PK) model (FIG. 10), data from various clinical studies (CAIN457A1101, CAIN457A2101, CAIN457A2102, CAIN457A2103, CAIN457A2104, CAIN457A2206, CAIN457A2208, CAIN457A2209 and CAIN457F2201) were pooled. A population approach with a two-compartmental model was used to describe secukinumab PK.

The population parameters were estimated together with their interindividual variances. The parameters were: distribution volumes V1=2.96 L and V2=2.52 L, first-order clearance from the first volume CL=0.169 L/day, intercompartmental exchange coefficient Q=0.784 L/day, and the absorption rate and absolute bioavailability for a subcutaneous administration were KA=0.192 1/day and F=76%, respectively. Body weight was identified as a covariate on secukinumab clearance and volumes.

Modeling of ACR20 Responder Rates in Placebo and Secukinumab Treatment Groups

For ACR20 modeling data on methotrexate inadequate responder patients (Table 9), data from two clinical studies (CAIN457A2101 and CAIN457F2201) were used. ACR20 responder rates were modeled using a concentration-responder probability approach for the placebo and treated groups. The assumption was that the ACR20 response rate increased monotonically until 16 weeks for placebo and treated groups. The monotonically increasing curve depended on the logarithm of time and the square root of secukinumab concentration. The observed ACR20 (LoCF) at weeks, 4 (day 29), 8 (day 57), 12 (day 86) and 16 (day 113) was modeled in two steps for placebo and the treated group.

ACR20 Time Profile Model for Placebo Group

The observed ACR20 at time $t_i$ (i=1, 2, 3, 4 denotes week 4, 8, 12 and 16) for j-th patient in placebo group was written as:

$$ACR20_{0j}(t_i)\sim\text{binomial}(1,p_0(t_i))$$

$$\text{Logit}(p_0(t_i))=\alpha+\beta\ \log(t_i)/\log(t_4).$$

Thus the logit of the ACR20 response rate in the placebo group at week 16 was α+β and at time 0 it was −∞ which corresponds to a probability to respond of 0 at time zero.

ACR20 Time Profile Model for Secukinumab Treated Group

The observed ACR20 at time $t_i$ for the j-th patients in secukinumab treated group was written as:

$$ACR20_j(t_i)\sim\text{binomial}(1,p(t_i))$$

$\text{Logit}(p(t_i))=\text{Logit}(p_0(t_i))+\gamma(t_i)h(\text{conc}_j(t_i))$, where h( ) was the square root of the individual model predicted concentration. Here γ was the change of sensitivity of ACR20 responder rate to the concentration at time $t_i$.

$$\gamma(t_i)=\gamma_0\ \log(t_i)/\log(t_4).$$

Hence the effect of secukinumab was described by $\gamma(t_i)h(\text{conc}_j(t_i))$. The functional form γ was chosen to be the log of study day, the same as placebo time effects, in other words a proportional odds in h(conc) was assumed.

The generalized estimating equation method was used for the evaluation and the within patient correlation of the ACR20 observed response were assumed to be compound symmetry.

Example 4.2—Results

Example 4.2.1—PK Modeling Results

Figure 10:
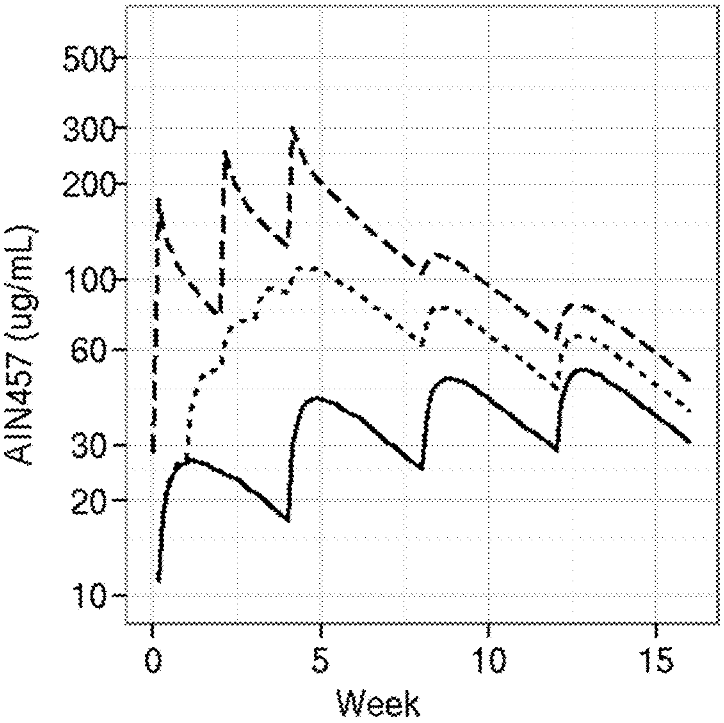
FIG. 10 shows simulated secukinumab pharmacokinetics (PK) in rheumatoid arthritis patients. The full line shows PK without an induction strategy (one dose of 300 mg s.c. at Week 0), dotted line shows PK with a subcutaneous induction strategy (300 mg s.c. at Weeks 0, 1, 2, 3 and 4) and dashed line shows PK with an intravenous induction strategy (10 mg/kg i.v. at Weeks 0, 2 and 4). Each of the three options is followed by 300 mg s.c. every 4 weeks for maintenance.
Figure 11:
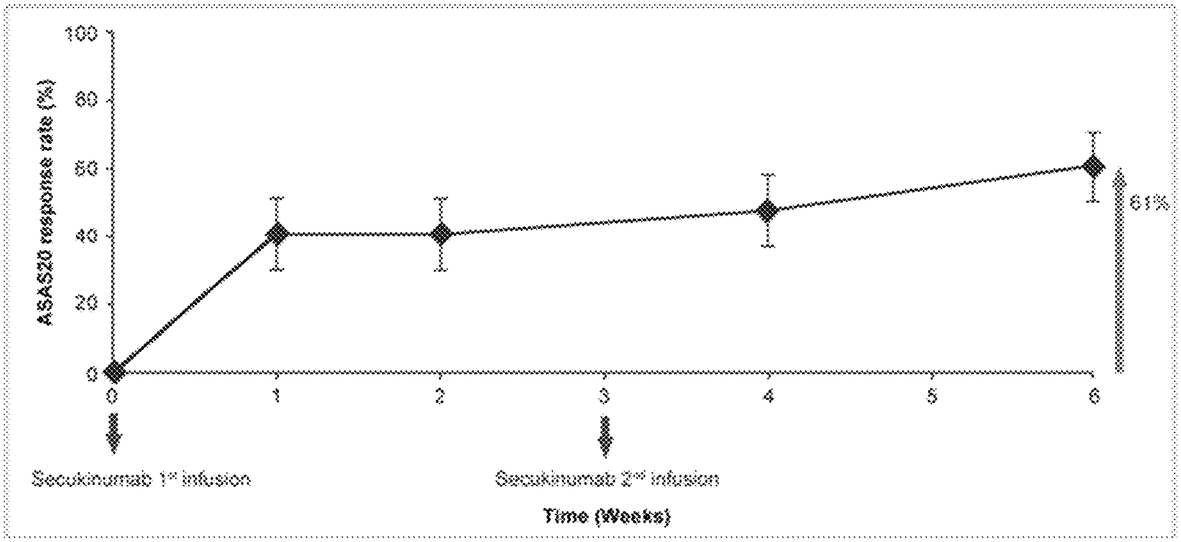
FIG. 11: Provides a Bayesian analysis of the Week 6 ASAS20 response rates of patients with moderate to severe AS treated with AIN457 i.v. given 3 weeks apart (trial CAIN457A2209, Example 5).

As can be seen in FIG. 10, the model predicts that a higher secukinumab plasma concentration can be achieved using either an i.v. or s.c. induction regimen in comparison to no induction regimen. Furthermore, the model further predicts that an induction regimen that uses 10 mg/kg secukinumab delivered i.v. at weeks 0, 2 and 4 can provide higher plasma concentration of secukinumab (and at a more rapid rate) than an induction regimen that uses 300 mg secukinumab delivered s.c. at weeks 0, 1, 2, 3 and 4. The s.c. and i.v. induction regimens modeled provided improved response in comparison to a dosing regimen lacking an induction regimen.

Example 4.2.4—ACR20 Simulation Results

The results from the ACR20 responder modeling are presented in Table 9. The ACR20 simulation predicts that a greater ACR20 response rate can be achieved using either an i.v. (63%) or s.c. (57%) induction regimen in comparison to no induction regimen (35%). Furthermore, the model further predicts that an induction regimen that uses 10 mg/kg secukinumab delivered i.v. at weeks 0, 2 and 4 can provide a greater ACR20 response rate than an induction regimen that uses 300 mg secukinumab delivered s.c. at weeks 0, 1, 2, 3 and 4. The s.c. and i.v. induction regimens modeled provided improved response in comparison to a dosing regimen lacking an induction regimen.

TABLE 9

Simulated ACR20 responder rates.

| Induction strategy | Induction dose-regimen | ACR20 response at week 4 with 95% confidence interval |
|---|---|---|
| No induction | 300 mg s.c. every 4 weeks | 35% (27-46) |
| Induction using s.c. dosing | 300 mg s.c. at Weeks 0, 1, 2, 3 and 4 followed by 300 mg s.c. every 4 weeks | 57% (41 -76) |
| Induction using i.v. dosing | 10 mg/kg i.v. at Weeks 0, 2 and 4 followed by 300 mg s.c. every 4 weeks | 63% (47 -81) |

Example 5: Secukinumab Shows Good Safety and Efficacy in the Treatment of Active Ankylosing Spondylitis

Example 5.1—Study Design CAIN457A2209

CAIN457A2209 is a pase II, multicenter, randomized, double-blind, parallel-group, placebo controlled proof-of-concept study in patients with moderate to severe AS. The study population is patients of age 18-65 years with AS diagnosed according to the modified New York criteria, back pain & nocturnal pain score ≥4 (0-10 point scale), a BASDAI score ≥4 (0-10 point scale), and inadequate response to current or previous use of at least one NSAID given over at least 3 months at maximum recommended dose. Patients with previous TNF-α blocker use were allowed to enroll after appropriate wash-out periods. Patients were allowed to continue concurrent treatment with NSAIDS, methotrexate (MTX), sulphasalazine, and prednisolone at stable doses during the study. However, patients with evidence of active tuberculosis were excluded.

Thirty (30) patients were randomised in a 4:1 ratio to receive two i.v infusions of either secukinumab (AIN457) 10 mg/kg i.v. or placebo i.v. given 3 weeks apart. Patients will be followed for safety up to week 28. A Bayesian analysis of the Week 6 ASAS20 response rates of AIN457 and placebo was performed. The prior distributions for the response rates were specified as Beta distributions and the binomial distribution was assumed for the observed number of responders in each group. The predictive distribution of the placebo response rate from a meta-analysis of 8 randomized, placebo-controlled trials of anti-TNFalpha treatment in AS was used as the prior distribution for the placebo response rate. This prior was equivalent to observing 11 out of 43 responders (i.e. a response rate of 26%). A weak prior was used for the active response rate (equivalent to observing 0.5 out of 1.5 responders).

Ther primary end point was the proportion of patients achieving the Assessment of Spondylo Arthritis international Society (ASAS) 20 response at week 6.

Example 5.2—Results

Demographics and baseline characteristics were comparable between groups. Mean (SD) BASDAI at baseline was 7.1 (1.4) for secukinumab-treated patients and 7.2 (1.8) for placebo-treated patients. Three patients on placebo and 2 patients on AIN457 discontinued the study prior to the primary endpoint, mostly due to unsatisfactory therapeutic effect. Efficacy data from 1 patient was not available due to a protocol violation after randomization. At week 6, 14/23 secukinumab-treated patients who entered efficacy analysis achieved ASAS20 responses versus 1/6 placebo treated patients (61% vs 17%, probability of positive-treatment difference=99.8%, credible interval 11.5%, 56.3%). ASAS40 and ASAS5/6 responses of secukinumab-treated patients were 30% and 35%, respectively, and mean (range) BASDAI change was −1.8 (−5.6 to 0.8). In a majority of the ASAS20 responders, secukinumab induced responses within a week of treatment. The pharmacokinetic profile was as expected for an IgG1 mAb and comparable to secukinumab given for other indications.

The primary endpoint of this study was met, as secukinumab induced significantly higher ASAS20 responses than placebo at week 6. No early safety signals were noted in this study population. Interim data presented here suggests that secukinumab has use in treating active ankylosing spondylitis.

Example 6—Secukinumab Reduces Signs and Symptoms of Psoriatic Arthritis in a 24-Week Multicenter, Double-Blind, Randomized, Placebo-Controlled Trial

Example 6.1—Study Design and Demographics

Fourty-two patients with active psoriatic arthritis (PsA) fulfilling CASPAR criteria were assigned 2:1 to receive two injections with secukinumab (10 mg/kg) or placebo, given three weeks apart. The primary efficacy endpoint was the proportion of ACR20 responders at Week 6 in active compared with placebo recipients (one-sided p-value <0.1). As per protocol, no imputation was made for missing data (drop-outs were treated as missing).

Twenty-five (89%) patients on secukinumab and 10 (71%) on placebo completed the study. Five patients (4 secukinumab and 1 placebo) were excluded from the efficacy analysis due to protocol violations. Three (11%) of patients on secukinumab and 4 (29%) on placebo discontinued prematurely for lack of efficacy or withdrawal of consent. Demographics and baseline characteristics were balanced between groups for age, sex and parameters including mean (SD) SJC (secukinumab vs. placebo): 8.3 (5.6) vs. 9.5 (5.4); TJC 23.5 (19.4) vs. 22.6 (11.0); DAS28 4.8 (1.2) vs. 4.8 (1.2); MASES 3.0 (4.1) vs. 3.4 (2.3). Co-existing psoriasis, prior TNFi exposure and co-medication with DMARDS were present in 23 (98%), 11 (46%) and 21

(88%) patients on secukinumab and in 11 (89%), 5 (38%) and 10 (70%) on placebo, respectively.

Example 6.2—Results

The ACR20 response rate at week 6 was 39% (9/23) on secukinumab vs. 23% (3/13) on placebo (P=0.27). ACR20 response rates were 39% (9/23) vs. 15% (2/13) at week 12, and 43% (10/23) vs. 18% (2/11) at week 28 with secukinumab versus placebo, respectively. ACR50 and ACR70 response rates at week 6 on secukinumab vs. placebo were 17% vs. 8% and 9% vs. 0%, respectively. CRP reductions at week 6 compared to baseline were observed on secukinumab (median [range] of 5.0 [0.3, 43.0] at baseline vs. 3.0 [0.2, 15.2] at week 6, but not on placebo (3.9 [1.3, 39.7] at baseline vs. 5.0 [0.8, 29.6] at week 6). Similar reductions were seen for ESR, and reductions in acute phase parameters were maintained up to week 28. The overall rate of adverse events (AEs) was comparable in secukinumab versus placebo: 26 (94%) vs. 11 (79%). One severe adverse event (cellulitis hand) occurred on secukinumab, and was not suspected by the investigator to be study drug-related. Seven serious AEs were reported in 4 secukinumab patients (tendon rupture/carpal tunnel syndrome/cellulitis, obesity, fall, breast cancer [diagnosed prior to dosing and inclusion constituting a protocol violation]) and 1 with placebo (polyarthritis). Infections were reported in 16 (57%) patients on secukinumab and 7 (50%) patients on placebo.

The safety profile of secukinumab was favorable overall. Although the primary endpoint was not met, a substantial proportion of patients showed rapid and sustained improvements of clinical scores and acute phase parameters up to week 28. Trends towards a beneficial clinical effect support the rationale for larger clinical trials designed to assess clinical effectiveness.

Example 7—Pharmokinetic (PK) Information for Secukinumab

Based on data obtained from various studies, including those discussed in the above Examples, the following PK information has been obtained for secukinumab (FIG. 12).

In addition, it has been determined that secukinumab has a $T_{max}$ of about 7-8 days, and an elimination half-life of about 30 days. This PK information can be used to design different dosing regimens for treatment of arthritis, e.g., RA, e.g., high risk RA. Using this PK information, one can deliver a different dosage of the IL-17 antagonist, e.g., an IL-17 binding molecule (e.g., an IL-17 antibody, such as secukinumab) or an IL-17 receptor binding molecule (e.g., an IL-17 receptor antibody) from the dosages used in the Examples or deliver the same dosage as used in the Examples, but which is provided at a different time point from the time points used in the Examples. By maintaining the same PK profile, even though a dosing regimen or a dosage may change, a skilled artisan is expected to be able to employ an the IL-17 antagonist, e.g., an IL-17 binding molecule (e.g., an IL-17 antibody, such as secukinumab) or an IL-17 receptor binding molecule (e.g., an IL-17 receptor antibody) for treatment of arthritis, including treatment of high risk RA patients.

Example 8: Pharmaceutical Compositions/Medicaments Comprising an IL-17 Antagonist A formulation study using secukinumab drug substance was initiated with the aim of developing a product of high strength, e.g., a vial having a unity dose of 150 mg secukinumab. Four sucrose-based formulations, in combination with different stabilizers (mannitol, glycine, arginine HCl), were included in the stability program at real, accelerated and stressed conditions for 12 months (Table 11).

TABLE 11

Formulations included in stability study

| Form | AIN457 Conc | Buffer | Stabilizer/ Bulking agent | Surfactant | pH |
|---|---|---|---|---|---|
| Before lyophilization | | | | | |
| 1 | 50 mg/mL | 10 mM Histidine | 90 mM Sucrose | 0.02% Polysorbate 80 | 5.8 |
| 2 | 50 mg/mL | 10 mM Histidine | 20 mM Sucrose, 60 mM Mannitol | 0.02% Polysorbate 80 | 5.8 |
| 3 | 50 mg/mL | 10 mM Histidine | 70 mM Sucrose, 20 mM Glycine | 0.02% Polysorbate 80 | 5.8 |
| 4 | 50 mg/mL | 10 mM Histidine | 65 mM Sucrose, 15 mM Arginine | 0.02% Polysorbate 80 | 5.8 |
| After reconstitution of the lyophilisate | | | | | |
| 1 | 150 mg/mL | 30 mM Histidine | 270 mM Sucrose | 0.06% Polysorbate 80 | 5.8 |
| 2 | 150 mg/mL | 30 mM Histidine | 60 mM Sucrose, 180 mM Mannitol | 0.02% Polysorbate 80 | 5.8 |
| 3 | 150 mg/mL | 30 mM Histidine | 210 mM Sucrose, 60 mM Glycine | 0.02% Polysorbate 80 | 5.8 |
| 4 | 150 mg/mL | 30 mM Histdine | 195 mM Sucrose, 46 mM Arginine | 0.02% Polysorbate 80 | 5.8 |

All formulations were filled at 3.6 mL (20% overfill) into 6 mL type I glass vials, capped with a Flurotec® B2 coated lyo configuration stopper and lyophilized using a conservative lyophilization cycle (Table 12).

TABLE 12

Lyophilization cycle conditions.

| Step | Operation | Time [hh:mm] | Shelf Temperature | Chamber Pressure |
|---|---|---|---|---|
| 1 | Vial Loading | As required | 20° C. | Ambient |
| 2 | Cooling down | 00:30 | 5° C. | Ambient |
| 3 | 5° C. hold | 03:00 | 5° C. | Ambient |
| 4 | Freeze ramp | 01:24 | 5° C. to −37° C. | Ambient |
| 5 | Freeze hold | 06:00 | −37° C. | Ambient |
| 6 | Chamber vacuum | 00:10 | −37° C. | 0.2 mbar |
| 7 | Primary drying ramp | 16:00 | −37° C. to 25° C. | 0.2 mbar |
| 8 | Secondary drying | 24:00 | 25° C. | 0.2 mbar |
| 9 | Vial stoppering | | 25° C. | 850 ± 59 mbar |

Secukinumab stability was monitored in the formulations through determination of cake appearance, pH, reconstitution time, residual moisture by Karl Fischer, aggregates and degradation products by SE-HPLC, impurities by SDS-PAGE under reducing conditions, average molecular weight by LLS, degradation products by RP-HPLC and theoretical activity by cystamine CEX. Osmolality and viscosity were determined after reconstitution 3:1 with water for injection at initial timepoint (Table 13).

TABLE 13

Osmolality and viscosity values for given formulations.

| Form | Formulation | Osmolality (mOsm/Kg) | Viscosity (mPa) |
|---|---|---|---|
| 1 | 270 mM Sucrose | 452 | 10.8 |
| 2 | 60 mM Sucrose, 180 mM Mannitol | 368 | 10.3 |
| 3 | 210 mM Sucrose, 60 mM Glycine | 440 | 10.5 |
| 4 | 195 mM Sucrose, 45 mM Arginine | 421 | 9.7 |

Osmolality values were well within the limit of PhEur acceptance criteria of higher than 240 mOsm/Kg and viscosity results in an acceptable range of 10 mPa*s. The 12 month stability data from samples stored at real temperature conditions indicated no differences in purity profile among the formulations with the different stabilizers. No significant difference among formulations was observed in appearance of lyophilisate cake and pH upon storage, however, the formulation containing mannitol showed a slightly longer reconstitution time when compared to the others (6 vs. 3 minutes). Moisture content increased from approximately 0.2% to 0.4% irrespective of formulation (data not shown). Aggregates by SEHPLC increased from approximately 0.9% to 1.4% whereas the degradation products were below the limit of quantification (data not shown). AIN457 average molecular weight remained unchanged after storage at approximately 155 kDa. Starting levels of total RP-HPLC species were approximately 8.5-10% with a significant increase up to 14.6% upon 12 months storage at 5° C. (data not shown). It should be highlighted that these levels reached a plateau from 1 month storage onwards. The AIN457 activity by Cystamine CEX was kept at 98-99% (data not shown). The 6 months stability data from samples stored at accelerated and stressed temperature conditions revealed that the formulation containing sucrose+mannitol was clearly differentiated from the others in terms of the longest reconstitution time (6 min vs. 3 min), highest aggregation product levels and generation of RP-HPLC degradation products upon storage. No significant difference among formulations was observed in appearance of lyophilisate cake and pH upon storage. Moisture content increased from approximately 0.2% to 0.6-0.7% irrespective of composition after 6 months storage at 40° C. (data not shown). The sucrose containing formulation showed a slightly lower aggregation level than the other formulations containing, additionally, mannitol, glycine and arginine HCl (5.2% vs. 5.8-6.8% by SE-HPLC). For all formulations, degradation products were below the limit of quantification (data not shown). AIN457 average molecular weight remained unchanged after 6 months storage at 40° C. at approximately 160 kDa. Total RP-HPLC degradation products were at slightly lower levels in the stand alone sucrose based formulation or with arginine HCl of up to 31.0% and 31.4% when compared to 32.8 and 35.6% in the other two formulations upon 6 months storage at 40° C. (data not shown). The AIN457 activity by cystamine CEX was kept at 94-95% (data not shown).

Results from the study showed that the 90 mM sucrose based formulation at 50 mg/mL in 10 mM histidine, 0.02% polysorbate 80, pH 5.8 prior to lyophilization was the most suitable candidate for market formulation containing 150 mg/mL AIN457, 30 mM L-histidine buffer pH 5.8, 270 mM sucrose and 0.06% polysorbate 80 after 3:1 reconstitution with 1.0 mL of water for injection.

What is claimed is:

1. A method of treating inflammatory arthritis in a patient in need thereof using secukinumab, wherein the method comprises subcutaneously administering every 2 weeks or every 4 weeks about 75 mg to about 300 mg of secukinumab to the patient, wherein the inflammatory arthritis is spondyloarthropathy or polymyalgia rheumatica.

2. The method according to claim 1, wherein the inflammatory arthritis is spondyloarthropathy.

3. The method according to claim 2, wherein the spondyloarthropathy is ankylosing spondylitis or psoriatic arthritis.

4. The method according to claim 2, wherein the spondyloarthropathy is psoriatic arthritis.

5. The method according to claim 4, comprising subcutaneously administering a dose of 75 mg, 150 mg, or 300 mg secukinumab.

6. The method according to claim 2, comprising subcutaneously administering a dose of 75 mg, 150 mg, or 300 mg secukinumab.

7. The method according to claim 1, wherein the inflammatory arthritis is polymyalgia rheumatica.

8. The method according to claim 1, wherein secukinumab is subcutaneously administered at a dose of about 75 mg to about 300 mg every 2 weeks to the patient.

9. The method according to claim 1, wherein secukinumab is subcutaneously administered at a dose of about 75 mg to about 300 mg every 4 weeks to the patient.

10. The method according to claim 9, wherein secukinumab is subcutaneously administered at a dose of about 75 mg every 4 weeks to the patient.

11. The method of claim 9, wherein secukinumab is administered at a dose of about 150 mg every 4 weeks to the patient.

12. The method of claim 11, wherein the patient was previously administered about 150 mg secukinumab by subcutaneous injection weekly for 4 weeks.

13. The method of claim 9, wherein secukinumab is administered at a dose of about 300 mg every 4 weeks to the patient.

14. The method of claim 13, wherein the patient was previously administered about 300 mg secukinumab by subcutaneous injection weekly for 4 weeks.

15. The method of claim 1, wherein the patient was previously administered about 75 mg secukinumab by subcutaneous injection weekly for 4 weeks.

16. The method according to claim 1, wherein the patient is an adult.

17. A method of treating inflammatory arthritis in a patient in need thereof using secukinumab, wherein the method comprises: a) administering three to five weekly doses of about 75 mg to about 300 mg secukinumab subcutaneously to the patient, and then b) subsequently administering a maintenance dose of about 75 mg to about 300 mg secukinumab subcutaneously every two weeks to every four weeks to the patient during a maintenance regimen.

18. The method according to claim 17, wherein the maintenance regimen comprises a subcutaneous administration every 4 weeks.

* * * * *